(12) United States Patent
Sastry-Dent et al.

(10) Patent No.: US 10,077,449 B2
(45) Date of Patent: Sep. 18, 2018

(54) UNIVERSAL DONOR SYSTEM FOR GENE TARGETING

(71) Applicant: Dow AgroSciences LLC, Indianapolis, IN (US)

(72) Inventors: Lakshmi Sastry-Dent, Avon, IN (US); Steven L. Evans, Zionsville, IN (US); Ryan C. Blue, Fishers, IN (US); Zehui Cao, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 831 days.

(21) Appl. No.: 14/531,710

(22) Filed: Nov. 3, 2014

(65) Prior Publication Data

US 2015/0143588 A1 May 21, 2015

Related U.S. Application Data

(60) Provisional application No. 61/899,543, filed on Nov. 4, 2013.

(51) Int. Cl.
C12N 15/82 (2006.01)

(52) U.S. Cl.
CPC ..... *C12N 15/8213* (2013.01); *C12N 15/8209* (2013.01); *C12N 15/8212* (2013.01); *C12N 15/8275* (2013.01)

(58) Field of Classification Search
None
See application file for complete search history.

(56) References Cited

U.S. PATENT DOCUMENTS

| | | | | |
|---|---|---|---|---|
| 2003/0049835 A1* | 3/2003 | Helliwell | ............... | C12N 15/10 435/320.1 |
| 2010/0199389 A1 | 8/2010 | Butler et al. | | |
| 2010/0257638 A1* | 10/2010 | Cai | ............... | C12N 15/8213 800/298 |
| 2011/0191899 A1 | 8/2011 | Ainley et al. | | |
| 2011/0296555 A1* | 12/2011 | Ivashuta | ............... | C12N 15/111 800/298 |
| 2012/0084882 A1* | 4/2012 | Wiig | ............... | C12N 15/8285 800/279 |

FOREIGN PATENT DOCUMENTS

| WO | WO 2003/080809 | 10/2003 |
|---|---|---|
| WO | WO 2008/148559 | 12/2008 |
| WO | WO 2010/077319 | 7/2010 |
| WO | WO 2011/091311 | 7/2011 |
| WO | WO 2011/091317 | 7/2011 |
| WO | WO 2011/154158 | 12/2011 |
| WO | WO 2013.009525 | 1/2013 |

OTHER PUBLICATIONS

Trotta (On the Normalization of the Minimum Free Energy of RNAs by Sequence Length. PLOS ONE vol. 9, 1-9, 2014).*
New England Biolabls, pUC19 Vector [online}, 2013.
GenBank AF177933.1 Cloning Vector pBS152v, 2003.
Database EMBL Accession No. AF177933 "Cloning vector pBS152v, complete sequence", Sep. 5, 2000.
GenBank FT202358.1 Rattus Norvegicus DNA, 2009.
Gordon, et al., "Specific expression of lacZ and cre recombinase in fetal thymic epithelial cells by multiplex gene targeting at the Foxn I locus," *BMC Developmental Biology*, 7:69, Jun. 18, 2007.
Huang et al. (1996) J. Protein Chem. 15:481-9.
Kim et al. (1994) Proc Natl. Acad. Sci. USA 91:883-7.
Kim et al. (1996) Proc. Natl. Acad. Sci. USA 93:1156-60.
Kim et al. (1997) Proc. Natl. Acad. Sci. USA 94:3616-20.
Kim et al. (1997b) Proc. Natl. Acad. Sci. USA 94:12875-9.
Kim et al. (1997c) Gene 2003:43-49.
Kim et al. (1998) Biol. Chem. 379:489-95.
Kumar, et al., "Controlling transgene integration in plants," *TRENDS in Plant Science*, vol. 6, No. 4, Apr. 2001.
Mani et al. (2005) Biochem. Biophys. Res. Commun. 334:1191-7.
Mann, et al., 2009, Nucl. Acids Res. vol. 37, No. 13, pp. E95 1-9.
Nahon and Raveh (1998) Nucleic Acids Res. 26:1233-9.
NCBI Reference NW 004675961.1, Setaria Italica Strain Yugul, 2013.
Paszkowski et at (1988) EMBO J. 7:4021-6.
Smith et al. (1999) Nucleic Acids Res. 27:674-81.
Smith et al. (2000) Nucleic Acids Res. 28:3361-9.
Zhang, et al., 2013, Plant Physiology Journal, vol. 161, No. 1, pp. 20-27.

* cited by examiner

*Primary Examiner* — Medina Ahmed Ibrahim
*Assistant Examiner* — Wayne Zhong
(74) *Attorney, Agent, or Firm* — Sean M. Russell; Barnes & Thornburg LLP

(57) ABSTRACT

A universal donor polynucleotide is described that can be inserted at targeted locations in plant genomes to facilitate rapid and high throughput integration of a donor molecule within a specific genomic location.

15 Claims, 10 Drawing Sheets

Specification includes a Sequence Listing.

FIG. 13A
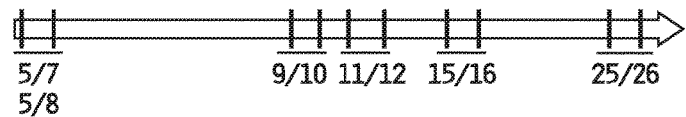
FIG. 13B
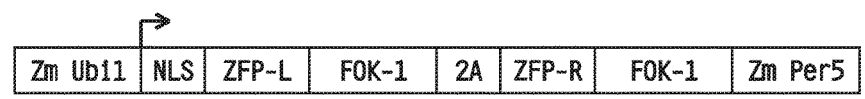
FIG. 13C
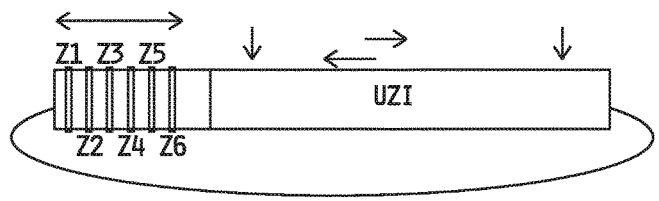
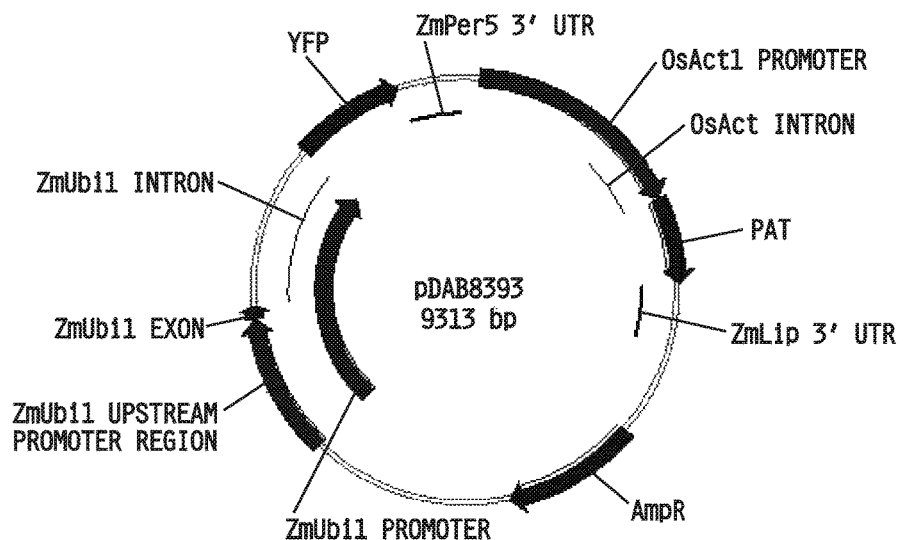
FIG. 14

| ID | Name | Treatment | # Indels/1M HQ reads |
|---|---|---|---|
| optimal_loci_204637 | OGL1 | C | 115.1827783 |
| | | ZFN 111879 | 2458.971273 |
| optimal_loci_204726 | OGL2 | C | 10.86457474 |
| | | ZFN 111885 | 102.9851891 |
| optimal_loci_31710 | OGL 11 | C | 1359.364352 |
| | | ZFN 117402 | 8209.320688 |
| optimal_loci_156393 | OGL 12 | C | 368.6331485 |
| | | ZFN 117404 | 7748.53473 |
| optimal_loci_157315 | OGL 13 | C | 79.11178495 |
| | | ZFN 117429 | 453.3253803 |
| optimal_loci_197372 | OGL 14 | C | 48.99318995 |
| | | ZFN 117406 | 277.1403482 |
| optimal_loci_198387 | OGL 15 | C | 45.49262935 |
| | | ZFN 117408 | 622.2166624 |
| optimal_loci_232228 | OGL 16 | C | 163.1649867 |
| | | ZFN 117411 | 5980.912998 |
| optimal_loci_285621 | OGL 17 | C | 0 |
| | | ZFN 117413 | 4.815941547 |

UNIVERSAL DONOR SYSTEM FOR GENE TARGETING

CROSS-REFERENCE TO RELATED APPLICATIONS

This application claims the benefit, under 35 U.S.C. § 119(e), to U.S. Provisional Patent Application No. 61/899,543, filed on Nov. 4, 2013, the contents of which are incorporated by reference in their entirety into the present application.

REFERENCE TO SEQUENCE LISTING SUBMITTED ELECTRONICALLY

The official copy of the sequence listing is submitted electronically via EFS-Web as an ASCII formatted sequence listing with a file named "74435_ST25.txt", created on Oct. 27, 2014, and having a size of 100 kilobytes and is filed concurrently with the specification. The sequence listing contained in this ASCII formatted document is part of the specification and is herein incorporated by reference in its entirety.

FIELD OF THE INVENTION

The disclosure relates to the field of plant precision transformation, gene targeting, targeted genomic integration and protein expression in plants. In an embodiment, the disclosure describes a universal donor polynucleotide molecule that can be inserted at targeted locations in plant genomes and assayed in a high throughput and efficient manner.

BACKGROUND OF THE INVENTION

The introduction of agronomically important traits into plants can be used to improve nutritional value quality, increase yield, provide pest or disease resistance, increase drought and stress tolerance, improve horticultural qualities (e.g., pigmentation and flowering), impart herbicide resistance, enable the production of industrially useful compounds and/or materials from the plant, and/or enabling the production of pharmaceuticals. Transgenic plants are typically generated by *Agrobacterium*-mediated transformation technology. Other transformation technologies such as PEG-mediated DNA uptake in protoplasts, microprojectile bombardment, and silicon whisker-mediated transformation can also be used to produce transgenic plants. The introduction of cloned genes into plant cells and recovery of stable fertile transgenic plants can be used to make such modifications of a plant and has allowed the genetic engineering of plants for crop improvement. Using these methods, foreign DNA is randomly integrated into the nuclear or plastid DNA of the eukaryotic plant cell, followed by isolation of cells containing the foreign DNA integrated into the cell's DNA, to produce stably transformed plant cells.

The plant transformation methods described above result in the integration of transgenes within random locations of the plant genome and in varying copy numbers. Frequently, the transgenes are integrated as repeats, either of the whole transgene or of parts thereof. Complex integration patterns may influence the expression level of the transgenes (e.g., by destruction of the transcribed RNA through posttranscriptional gene silencing mechanisms, or by inducing methylation of the introduced DNA), thereby downregulating transcription of the transgene. Furthermore, the expression level of the transgene can be influenced by the location of the integration (e.g., position effect) within the plant genome. The combination of these factors results in a wide variation in the level of expression of the transgenes or foreign DNA of interest among different transgenic plant cell and plant lines. Moreover, the integration of the foreign DNA of interest may have a disruptive effect on the region of the genome where the integration occurs and can influence or disturb the normal function of that target region, thereby leading to often undesirable side-effects.

The foregoing necessitate that, whenever the effect of introduction of a particular foreign DNA into a plant is investigated, a large number of transgenic plant lines are generated and analyzed in order to obtain significant results. Likewise, in the generation of transgenic crop plants, where a particular DNA of interest is introduced in plants to provide the transgenic plant with a desired phenotype, a large population of independently created transgenic plant lines is created to allow the selection of those plant lines with optimal expression of the transgenes, and with minimal or no side-effects on the overall phenotype of the transgenic plant. Particularly in this field, more directed transgenic approaches are desired, for example, in view of the burdensome regulatory requirements and high costs associated with the repeated filed trials required for the elimination of the unwanted transgenic events. Furthermore, it will be clear that the possibility of targeted DNA insertion would also be beneficial in the process of transgene stacking.

Several methods have been developed in an effort to control transgene insertion in plants. See, e.g., Kumar and Fladung (2001) Trends Plant Sci. 6:155-9. These methods rely on homologous recombination-based transgene integration. This strategy has been successfully applied in prokaryotes and lower eukaryotes. Paszkowski et al. (1988) EMBO J. 7:4021-6. However, for plants, until recently the predominant mechanism for transgene integration is based on illegitimate recombination which involves little homology between the recombining DNA strands. A major challenge in this area is therefore the detection of the rare homologous recombination events, which are masked by the far more efficient integration of the introduced foreign DNA via illegitimate recombination.

Custom-designed zinc finger nucleases (ZFNs) are proteins designed to deliver a targeted site-specific double-strand break in DNA, with subsequent recombination of the cleaved ends. ZFNs combine the non-specific cleavage domain of a restriction endonuclease, such as for example Fok1, with zinc finger DNA-binding proteins. See, e.g., Huang et al. (1996) J. Protein Chem. 15:481-9; Kim et al. (1997) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. Individual zinc finger motifs can be designed to target and bind to a large range of DNA sites. Canonical $Cys_2His_2$ as well as non-canonical $Cys_3His$ zinc finger proteins bind DNA by inserting an α-helix into the major groove of the double helix. Recognition of DNA by zinc fingers is modular: each finger contacts primarily three consecutive base pairs in the target, and a few key residues in the protein mediate recognition. It has been shown that FokI restriction endonuclease must dimerize via the nuclease domain in order to cleave DNA, inducing a double-strand break. Similarly, ZFNs also require dimerization of the nuclease domain in order to cut DNA. Mani et al. (2005) Biochem. Biophys. Res. Commun. 334:1191-7; Smith et al. (2000) Nucleic Acids Res. 28:3361-9. Dimerization of the ZFN is facilitated by two adjacent, oppositely oriented binding sites. id.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

In a preferred embodiment, the disclosure relates to a polynucleotide donor cassette comprising a site specific nuclease binding domain, an analytical domain, and a plasmid domain. In a further embodiment, the polynucleotide donor cassette comprises a length of less than 3 Kbp. Further embodiments include a transgenic cell comprising the polynucleotide donor cassette. In some aspects, the transgenic cell is a transgenic plant cell. In another embodiment, the disclosure relates to a transgenic plant comprising the transgenic plant cell. Further aspects include the transgenic plant, wherein the plant is a monocotyledonous plant or a dicotyledonous plant. In other embodiments the monocotyledonous plant is selected from the group consisting of a maize plant, a wheat plant, and a rice plant. In yet other embodiments the dicotyledonous plant is selected from the group consisting of a soybean plant, a cotton plant, and a canola plant. Still further the disclosure relates to a transgenic seed produced from the transgenic plant.

In yet another embodiment the subject disclosure relates to the polynucleotide donor cassette, wherein the polynucleotide donor cassette is selected from the group consisting of a polynucleotide sequence with at least 90% sequence identity to SEQ ID NO:132, a polynucleotide sequence with 90% sequence identity to SEQ ID NO:133, a polynucleotide sequence with at least 90% sequence identity to SEQ ID NO:134, a polynucleotide sequence with at least 90% sequence identity to SEQ ID NO:135, a polynucleotide sequence with at least 90% sequence identity to SEQ ID NO:136, a polynucleotide sequence with at least 90% sequence identity to SEQ ID NO:137, a polynucleotide sequence with at least 90% sequence identity to SEQ ID NO:138, a polynucleotide sequence with at least 90% sequence identity to SEQ ID NO:139, a polynucleotide sequence with at least 90% sequence identity to SEQ ID NO:140 and a polynucleotide sequence with at least 90% sequence identity to SEQ ID NO:141.

In further embodiments, the polynucleotide donor cassette is comprised of a site specific nuclease binding domain that is made up of one or more site specific nuclease binding sequences. In an aspect, the site specific nuclease binding domain comprising one or more site specific nuclease binding sequences is bound by a zinc finger binding protein, a meganuclease binding protein, a CRISPR binding protein, or a TALEN binding protein.

In other embodiments, the polynucleotide donor cassette comprises an analytical domain selected from the group consisting of a polynucleotide sequence with at least 90% sequence identity to SEQ ID NO: 142 and a polynucleotide sequence with at least 90% sequence identity to SEQ ID NO:143. In some aspects the analytical domain comprises one or more restriction enzyme sequences. In other aspects the analytical domain comprises a guanine and cytosine base pair percentage of 40 to 60%. In further aspects, the analytical domain comprises a polynucleotide that does not contain a plurality of repetitive sequences, wherein the repetitive sequence is at least 9 Bp in length. In additional aspects, the analytical domain comprises a polynucleotide that does not contain a series of identical base pair sequences greater than 9 Bp in length. In an aspect, the analytical domain comprises a polynucleotide with a secondary structure of more than −19 kcal/mol free energy (ΔG). In various other aspects, the analytical domain comprises one or more primer binding sequences.

In an embodiment, the polynucleotide donor cassette comprises one or more homology arm sequences. In other aspects the one or more homology arm sequences are between 50 and 100 base pairs in length. In another embodiment, the analytical domain does not encode a peptide. In yet another embodiment, the analytical domain does encode a peptide. In an aspect, the analytical domain comprises a gene expression cassette comprising a transgene. In a further aspect, the gene expression cassette comprises a promoter. In yet another aspect, the transgene comprises a reporter gene. In an additional aspect, the reporter gene is selected from the group consisting of a yfp gene, a gus gene, a rfp gene, a gfp gene, a kanamycin resistance gene, an aad-1 gene, an aad-12 gene, a pat gene, and a glyphosate tolerant gene. In an additional embodiment, the plasmid domain comprises a pUC19 plasmid. In an aspect, the plasmid domain comprises a high-copy number origin of replication. In a further aspect, the high-copy number origin of replication comprises a colel origin of replication. In an additional aspect, the plasmid domain comprises a selectable marker. In a further aspect, the selectable marker is selected from the group consisting of a kanamycin selectable marker, an ampicillin selectable marker, a spectinomycin selectable marker, a chloramphenicol selectable marker, and a rifampicin selectable marker.

In an embodiment the subject disclosure relates to a method for targeted integration of a polynucleotide donor cassette within the genome of a plant cell. In an aspect the, the method relates to expressing a site specific DNA binding nuclease, comprising at least one DNA-binding domain and at least one nuclease domain, wherein the at least one DNA-binding domain binds to a target site within the genome of the plant cell; contacting the plant cell with a polynucleotide donor cassette; cleaving the target site within the genome of the plant cell with the site specific DNA binding nuclease; and, integrating the polynucleotide donor cassette into the target site within the genome of the plant cell. In a further aspect, the at least one DNA-binding domain is selected from the group consisting of a zinc finger binding domain, a meganuclease binding domain, a TALEN binding domain, a meganuclease, and a CRISPR binding domain. In another aspect, the nuclease domain is from a Type IIS restriction endonuclease. In another aspect, the Type IIS restriction endonuclease is selected from the group consisting of FokI and StsI. In an additional aspect, the polynucleotide donor cassette expresses a polypeptide. In yet another aspect, the polynucleotide donor cassette comprises a non-coding nucleic acid sequence. In an aspect, the polynucleotide donor cassette comprises one or more zinc finger binding sequences. In another aspect, the polynucleotide donor cassette comprises one or more primer binding sequences. In an additional aspect, the integrating of the polynucleotide donor cassette occurs via a homology directed repair mechanism. In an additional aspect, the integrating of the polynucleotide donor cassette occurs via a non-homologous end joining directed repair mechanism. In one embodiment the plant cell selected for integration of the polynucleotide donor cassette is a monocotyledonous or dicotyledonous plant cell. In one embodiment, the plant cell is a monocotyledonous plant cell selected from the group consisting of a maize plant cell, a wheat plant cell, and a rice plant cell. In one embodiment, the plant cell is a dicotyledonous plant cell selected from the group consisting of a soybean plant cell, a cotton plant cell, and a canola plant cell.

In addition to the exemplary aspects and embodiments described above, further aspects and embodiments will become apparent by study of the following descriptions.

BRIEF DESCRIPTION OF THE FIGURES

FIG. 13A-13C Illustrates the constructs used for targeting and validation of the universal donor polynucleotide system integration within the *Zea mays* optimal genomic loci targeting and validation. FIG. 13A) ZFN design space with location of the ZFN pairs as previously shown in pDAB111845 of FIG. 5. The ZFN pairs are labeled numerically and correspond with specific ZFN binding sequences that are specifically recognized by ZFN proteins for binding and cleavage. FIG. 13B) Configuration of the ZFN protein expression construct. The ZFN expression construct contains a constitutive plant promoter (Zm Ubi1) which is used to drive expression of the ZFN protein. The ZFN protein contains the nuclear localization sequence (NLS), the zinc finger proteins (ZFP-L and ZFP-R, where L indicates left hand binding ZFN protein and R indicates right hand binding protein), Fok-1 endonuclease (Fok1) and the self-hydrolyzing 2A (2A). FIG. 13C) universal donor polynucleotide for NHEJ mediated targeting of *Zea mays* optimal genomic loci. Z1-Z6 represent ZFN binding sites specific for a *Zea mays* optimal genomic loci target. The number of ZFN sites can vary from 3-6. Vertical arrows show unique restriction sites and horizontal arrows represent potential PCR primer sites. The universal donor polynucleotide system is a short (110 bp) sequence that is common to donors used for integration within *Zea mays* optimal genomic loci.

FIG. 14 illustrates a plasmid map of pDAB8393.

DETAILED DESCRIPTION

I. Overview

Figure 1:
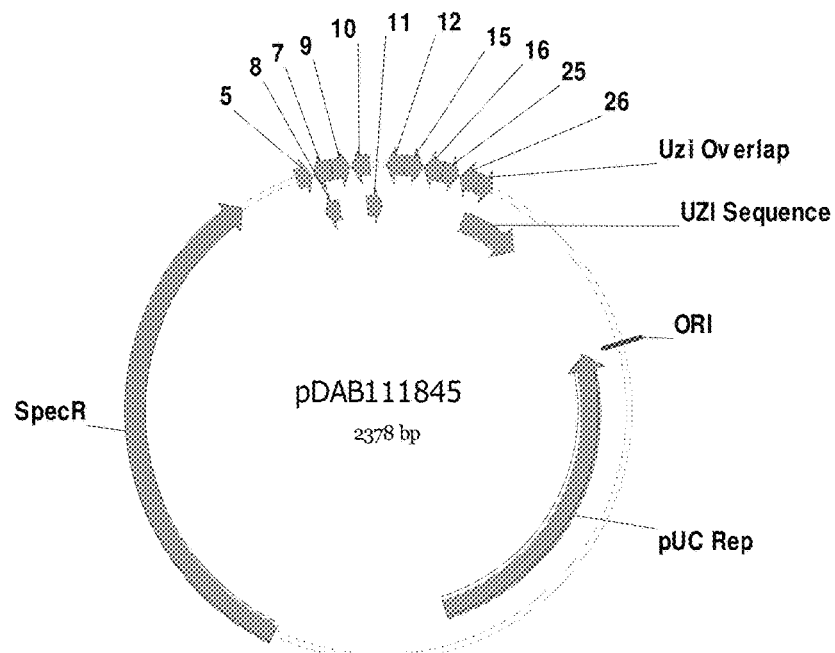
FIG. 1 illustrates a plasmid map of pDAB111845. The numbered elements (i.e., 5, 7, 8, 9, 10, 11, 12, 15, 16, 25, and 26) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette.

The present disclosure provides, in various aspects, polynucleotide donor cassettes comprising a zinc finger nuclease binding domain, an analytical domain, and a plasmid domain. In other aspects, the present disclosure provides methods that provide for the targeted integration of polynucleotide donor cassettes within the genome of a plant cell. According to the disclosed methods, a site specific DNA binding nuclease, comprising at least one DNA-binding domain and at least one nuclease domain, is expressed such that at least one DNA-binding domain binds to a target site within the genome of the plant cell. In addition, the plant cell is contacted with a polynucleotide donor cassette. Subsequently, the target site within the genome of the plant cell is cleaved with the site specific DNA binding nuclease, and the polynucleotide donor cassette is integrated into the target site within the genome of the plant cell.

II. Terms

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises", "comprising", "includes", "including", "has", "having", "contains", or "containing", or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "invention" or "present invention" as used herein is a non-limiting term and is not intended to refer to any single embodiment of the particular invention but encompasses all possible embodiments as disclosed in the application.

As used herein, the term "plant" includes a whole plant and any descendant, cell, tissue, or part of a plant. The term "plant parts" include any part(s) of a plant, including, for example and without limitation: seed (including mature seed, immature embryo without testa, and immature seed); a plant cutting; a plant cell; a plant cell culture; a plant organ (e.g., pollen, embryos, flowers, fruits, shoots, leaves, roots, stems, and related explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant. Plant cells, as used herein, includes protoplasts and protoplasts with a partial cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant part" in embodiments herein.

The term "protoplast", as used herein, refers to a plant cell that had its cell wall completely or partially removed, with the lipid bilayer membrane thereof naked. Typically, a protoplast is an isolated plant cell without cell walls which has the potency for regeneration into cell culture or a whole plant.

As used herein, "endogenous sequence" defines the native form of a polynucleotide, gene or polypeptide in its natural location in the organism or in the genome of an organism.

The term "isolated" as used herein means having been removed from its natural environment.

The term "purified", as used herein relates to the isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

As used herein, the terms "polynucleotide", "nucleic acid", and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single and double-stranded DNA; DNA that is a mixture of single- and double-stranded regions; single and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein the term "analytical domain" defines a nucleic acid sequence that contains functional elements that assist in the targeted insertion of nucleic acid sequences. For example, an analytical domain may contain specifically designed restriction enzyme sites, zinc finger binding sites, engineered landing pads or engineered transgene integration platforms and may or may not comprise gene regulatory elements or an open reading frame. See, for example, U.S. Patent Publication No 20110191899, incorporated herein by reference in its entirety.

As defined herein a "site specific nuclease binding domain" is a nucleic acid sequence that comprises one or more site specific binding sequences. As used herein a site specific binding sequence is a nucleic acid sequence that binds to a protein in sequence-specific interaction.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide", and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a heterologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another gene or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

As used herein, the term "modification" can refer to a change in a polynucleotide disclosed herein that results in reduced, substantially eliminated or eliminated activity of a polypeptide encoded by the polynucleotide, as well as a change in a polypeptide disclosed herein that results in reduced, substantially eliminated or eliminated activity of the polypeptide. Alternatively, the term "modification" can refer to a change in a polynucleotide disclosed herein that results in increased or enhanced activity of a polypeptide encoded by the polynucleotide, as well as a change in a polypeptide disclosed herein that results in increased or enhanced activity of the polypeptide. Such changes can be made by methods well known in the art, including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified, can be found by comparing the sequence of the particular polynucleotide or polypeptide with that of homologous polynucleotides or polypeptides, and maximizing the number of modifications made in regions of high homology (conserved regions) or consensus sequences.

The term "derivative", as used herein, refers to a modification of a sequence set forth in the present disclosure. Illustrative of such modifications would be the substitution, insertion, and/or deletion of one or more bases relating to a nucleic acid sequence of a coding sequence disclosed herein that preserve, slightly alter, or increase the function of a coding sequence disclosed herein in crop species. Such derivatives can be readily determined by one skilled in the art, for example, using computer modeling techniques for predicting and optimizing sequence structure. The term "derivative" thus also includes nucleic acid sequences having substantial sequence identity with the disclosed coding sequences herein such that they are able to have the disclosed functionalities for use in producing embodiments of the present disclosure.

The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise rationally designed DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

The term "expression", as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic", "recombinant", or "transformed" organisms. Known methods of transformation include, for example: *Agrobacterium tumefaciens*- or *A. rhizogenes*-mediated transformation; calcium phosphate transformation; polybrene transformation; protoplast fusion; electroporation; ultrasonic methods (e.g., sonoporation); liposome transformation; microinjection; transformation with naked DNA; transformation with plasmid vectors; transformation with viral vectors; biolistic transformation (microparticle bombardment); silicon carbide WHISKERS-mediated transformation; aerosol beaming; and PEG-mediated transformation.

As used herein, the term "introduced" (in the context of introducing a nucleic acid into a cell) includes transformation of a cell, as well as crossing a plant comprising the nucleic acid with a second plant, such that the second plant contains the nucleic acid, as may be performed utilizing conventional plant breeding techniques. Such breeding techniques are known in the art. For a discussion of plant breeding techniques, see Poehlman (1995) Breeding Field Crops, 4th Edition, AVI Publication Co., Westport Conn.

Backcrossing methods may be used to introduce a nucleic acid into a plant. This technique has been used for decades to introduce traits into plants. An example of a description of backcrossing (and other plant breeding methodologies) can be found in, for example, Poelman (1995), supra; and Jensen (1988) Plant Breeding Methodology, Wiley, New York, N.Y. In an exemplary backcross protocol, an original plant of interest (the "recurrent parent") is crossed to a second plant (the "non-recurrent parent") that carries the nucleic acid be introduced. The resulting progeny from this cross are then crossed again to the recurrent parent, and the process is repeated until a converted plant is obtained, wherein essentially all of the desired morphological and physiological characteristics of the recurrent parent are recovered in the converted plant, in addition to the nucleic acid from the non-recurrent parent.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least one region of homology to the genome ("homology arms") of least 50-100 base pairs in length. See, e.g., U.S. Patent Publication No. 20110281361.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

The terms "plasmid" and "vector", as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may carry DNA derived from essentially any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences for propagating in bacterial hosts.

Polypeptide and "protein" are used interchangeably herein and include a molecular chain of two or more amino acids linked through peptide bonds. The terms do not refer to a specific length of the product. Thus, "peptides", and "oligopeptides", are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be synthesized, or expressed recombinantly using known protein engineering techniques. In addition, inventive fusion proteins can be derivatized as described herein by well-known organic chemistry techniques.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

III. Embodiments of the Present Invention

In one embodiment of the present disclosure, a polynucleotide donor cassette comprising a zinc finger nuclease binding domain, an analytical domain, and a plasmid domain is provided.

In some embodiment the polynucleotide donor cassette of claim 1, the polynucleotide donor cassette comprises a length of less than 3 Kbp. Exemplary, lengths of polynucleotide donor cassettes may be about 3 Kbp, 2.9 Kbp, 2.8 Kbp, 2.7 Kbp, 2.6 Kbp, 2.5 Kbp, 2.4 Kbp, 2.3 Kbp, 2.2 Kbp, 2.1 Kbp, 2.0 Kbp, 1.9 Kbp, 1.8 Kbp, 1.7 Kbp, 1.6 Kbp, 1.5 Kbp, 1.4 Kbp, 1.3 Kbp, 1.2 Kbp, 1.1 Kbp, 1.0 Kbp, 0.9 Kbp, 0.8 Kbp, 0.7 Kbp, 0.6 Kbp, 0.5 Kbp, 0.4 Kbp, 0.3 Kbp, 0.2 Kbp, or 0.1 Kbp. The term "base pair" (also described as "bp") refers to a pair of nucleotide bases (nucleotides) each in a separate single stranded nucleic acid in which each base of the pair is non-covalently bonded to the other (e.g., via hydrogen bonds). For instance, a Watson-Crick base pair usually contains one purine and one pyrimidine. Guanosine can pair with cytosine (G-C), adenine can pair with thymine (A-T), and uracil can pair with adenine (U-A). The two bases in a base pair are said to be complementary to each other. Base pairs may be referenced as kilo base pairs (Kbp), mega base pairs (Mbp) of giga base pairs (Gbp), wherein "kilo" denotes an increment of one thousand, and "mega" denotes an increment of one million, and "giga" denotes an increment of one billion.

In other embodiments a cell is transformed with the polynucleotide donor cassette comprising a site specific nuclease binding domain, an analytical domain, and a plasmid domain and the polynucleotide donor cassette is integrated into the host cell's DNA. The term "cell" as referred to herein encompasses a living organism capable of self replication, and may be a eukaryotic or prokaryotic cell. In some embodiments the transformed cell is a plant cell. In some embodiments, the plant cell can be but is not limited to any higher plant, including both dicotyledonous and monocotyledonous plants, and consumable plants, including crop plants and plants used for their oils. Thus, any plant species or plant cell can be selected for transformation as described further below.

In some embodiments, a plant cell transformed in accordance with the present disclosure includes, but is not limited to, any higher plants, including both dicotyledonous and monocotyledonous plants, and particularly consumable plants, including crop plants. Such plants can include, but are not limited to, for example: alfalfa, soybeans, cotton, rapeseed (also described as canola), linseed, corn, rice, brachiaria, wheat, safflowers, sorghum, sugarbeet, sunflowers, tobacco and turf grasses. Thus, any plant species or plant cell can be selected. In some embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*; Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea* eurpaea); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* and *Triticum aestivum*); and duckweed (*Lemnaceae* sp.). In some embodiments, the genetic background within a plant species may vary.

With regard to the production of genetically modified plants, methods for the genetic engineering of plants are well known in the art. For instance, numerous methods for plant transformation have been developed, including biological and physical transformation protocols for dicotyledenous plants as well as monocotyledenous plants (e.g., Goto-Fumiyuki et al., *Nature Biotech* 17:282-286 (1999); Mild et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

A large number of techniques are available for inserting DNA into a plant host cell. Those techniques include transformation with disarmed T-DNA using *Agrobacterium tumefaciens* or *Agrobacterium rhizogenes* as the transformation agent, calcium phosphate transfection, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS mediated transformation, aerosol beaming, or PEG as well as other possible methods.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) Nature 327:70-73). Additional methods for plant cell transformation include microinjection via silicon carbide WHISKERS mediated DNA uptake (Kaeppler et al. (1990) Plant Cell Reporter 9:415-418). Alternatively, the DNA construct can be introduced into the plant cell via nanoparticle transformation (see, e.g., U.S. patent application Ser. No. 12/245, 685, which is incorporated herein by reference in its entirety).

Another known method of plant transformation is microprojectile-mediated transformation wherein DNA is carried on the surface of microprojectiles. In this method, the vector is introduced into plant tissues with a biolistic device that accelerates the microprojectiles to speeds sufficient to penetrate plant cell walls and membranes. Sanford et al., Part. Sci. Technol. 5:27 (1987), Sanford, J. C., Trends Biotech. 6:299 (1988), Sanford, J. C., Physiol. Plant 79:206 (1990), Klein et al., Biotechnology 10:268 (1992).

Alternatively, gene transfer and transformation methods include, but are not limited to, protoplast transformation through calcium chloride precipitation, polyethylene glycol (PEG)- or electroporation-mediated uptake of naked DNA (see Paszkowski et al. (1984) EMBO J 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of plant tissues (D'Halluin et al. (1992) Plant Cell 4:1495-1505).

A widely utilized method for introducing an expression vector into plants is based on the natural transformation system of *Agrobacterium*. Horsch et al., Science 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., Crit. Rev. Plant. Sci. 10:1 (1991). Descriptions of *Agrobacterium* vector systems and methods for *Agrobacterium*-mediated gene transfer are also available, for example, Gruber et al., supra, Mild et al., supra, Moloney et al., Plant Cell Reports 8:238 (1989), and U.S. Pat. Nos. 4,940,838 and 5,464,763.

If *Agrobacterium* is used for the transformation, the DNA to be inserted should be cloned into special plasmids, namely either into an intermediate vector or into a binary vector. Intermediate vectors cannot replicate themselves in *Agrobacterium*. The intermediate vector can be transferred into *Agrobacterium tumefaciens* bp use of a helper plasmid (conjugation). The Japan Tobacco Superbinary system is an example of such a system (reviewed by Komari et al., (2006) In: Methods in Molecular Biology (K. Wang, ed.) No. 343: *Agrobacterium* Protocols (2nd Edition, Vol. 1) Humana Press Inc., Totowa, N.J., pp. 15-41; and Komori et al., (2007) Plant Physiol. 145:1155-1160). Binary vectors can replicate themselves both in *E. coli* and in *Agrobacterium*. They comprise a selection marker gene and a linker or polylinker which are framed by the right and left T-DNA border regions. They can be transformed directly into *Agrobacterium* (Holsters, 1978). The *Agrobacterium* used as host cell is to comprise a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) Nuc. Acid Res. 12:8711-8721) or the co-cultivation procedure (Horsch et al. (1985) Science 227:1229-1231). Generally, the *Agrobacterium* transformation system is used to engineer dicotyledonous plants (Bevan et al. (1982) Ann. Rev. Genet 16:357-384; Rogers et al. (1986) Methods Enzymol. 118:627-641). The *Agrobacterium* transformation system may also be used to transform, as well as transfer, DNA to monocotyledonous plants and plant cells. See U.S. Pat. No. 5,591,616; Hernalsteen et al. (1984) EMBO J 3:3039-3041; Hooykass-Van Slogteren et al. (1984) Nature 311:763-764; Grimsley et al. (1987) Nature 325:1677-179; Boulton et al. (1989) Plant Mol. Biol. 12:31-40; and Gould et al. (1991) Plant Physiol. 95:426-434. Following the introduction of the genetic construct into particular plant cells, plant cells can be grown and upon emergence of differentiating tissue such as shoots and roots, mature plants can be generated. In some embodiments, a plurality of plants can be generated. Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). The genetically modified plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al. (1987) Ann. Rev. of Plant Phys. 38:467-486.

In other embodiments, the plant cells which are transformed are not capable of regeneration to produce a plant. Such cells are said to be transiently transformed. Transiently transformed cells may be produced to assay the expression and/or functionality of a specific transgene. Transient transformation techniques are known in the art, and comprise minor modifications to the transformation techniques described above. Those with skill in the art may elect to utilize transient transformation to quickly assay the expression and/or functionality of a specific transgenes, as transient transformation are completed quickly and do not require as many resources (e.g., culturing of plants for development of whole plants, self-fertilization or crossing of plants for the fixation of a transgene within the genome, etc.) as stable transformation techniques.

In an embodiment the universal donor polynucleotide can be introduced into essentially any plant. A wide variety of plants and plant cell systems may be engineered for site specific integration of the universal donor polynucleotide of the present disclosure and the various transformation methods mentioned above. In an embodiment, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea mays*.

In other embodiments the polynucleotide donor cassette comprises a specific polynucleotide sequence. Examples of specific polynucleotide sequences include, but are not limited to; SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140 and SEQ ID NO:141. In various embodiments, sequences with at least 90% sequence identity to the specific polynucleotide sequences SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140 and SEQ ID NO:141 are disclosed herein. In other embodiments, sequences with at least 95% sequence identity to the specific polynucleotide sequences SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140 and SEQ ID NO:141 are disclosed herein. In other embodiments, sequences with at least 97% sequence identity to the specific polynucleotide sequences SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140 and SEQ ID NO:141 are disclosed herein. In yet other embodiments, sequences with at least 99% sequence identity to the specific polynucleotide sequences SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140 and SEQ ID NO:141 are disclosed herein. In one embodiment the polynucleotide donor cassette comprises a sequence having at least 90, 93, 95, 97 or 99% sequence identity with a sequence selected from the group consisting of SEQ ID NO: 142 and 143.

The term "percent identity" (or "% identity"), as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) Computational Molecular Biology (Lesk, A. M., Ed.) Oxford University: NY (1988); 2.) Biocomputing: Informatics and Genome Projects (Smith, D. W., Ed.) Academic: NY (1993); 3.) Computer Analysis of Sequence Data, Part I (Griffin, A. M., and Griffin, H. G., Eds.) Humania: NJ (1994); 4.) Sequence Analysis in Molecular Biology (von Heinje, G., Ed.) Academic (1987); and 5.) Sequence Analysis Primer (Gribskov, M. and Devereux, J., Eds.) Stockton: NY (1991).

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. See Russell, R., and Barton, G., "Structural Features can be Unconserved in Proteins with Similar Folds," J. Mol. Biol. 244, 332-350 (1994), at p. 337, which is incorporated herein by reference in its entirety.

In addition, methods to determine identity and similarity are codified in publicly available computer programs. Sequence alignments and percent identity calculations can be performed, for example, using the AlignX program of the Vector NTI® suite (Invitrogen, Carlsbad, Calif.) or MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, CABIOS. 5:151-153 (1989); Higgins, D. G. et al., Comput. Appl. Biosci., 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, CABIOS. 5:151-153 (1989); Higgins, D. G. et al., Comput. Appl. Biosci. 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, plasmid DNA fragments, cDNA fragments, RNA fragments, PCR amplified DNA fragments, oligonucleotides, or other polynucleotides, and may be labeled with a detectable group such as $^{32}P$, or any other detectable marker. Thus, for example, probes for hybridization can be made by labeling synthetic oligonucleotides based on the DNA sequences of embodiments of the disclosure. Methods for preparation of probes for hybridization and for construction of cDNA and genomic libraries are generally known in the art and are disclosed (Sambrook et al., 1989).

The nucleic acid probes and primers of embodiments of the present disclosure hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if the two nucleic acid molecules exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe, it need only exhibit the minimal complementarity of sequence to be able to form a stable double-stranded structure under the particular solvent and salt concentrations employed.

Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Typically, stringent conditions will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 0.1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 0.1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C.

Specificity is typically a function of post-hybridization washes, the critical factors being the ionic strength and temperature of the final wash solution. For DNA-DNA hybrids, the $T_m$ can be approximated from the equation $T_m=81.5°$ C.$+16.6$ (log M)$+0.41$(% GC)$-0.61$(% form.)$-500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al, *Short Protocols in Molecular Biology*, pages 2-40, Third Edit. (1997) and Sambrook et al. (1989).

In an embodiment, the polynucleotide donor cassette comprises one or more zinc finger nuclease binding domain. As such, an embodiment of the polynucleotide donor cassette comprises 1 zinc finger nuclease binding domain, 2 zinc finger nuclease binding domains, 3 zinc finger nuclease binding domains, 4 zinc finger nuclease binding domains, 5 zinc finger nuclease binding domains, 6 zinc finger nuclease binding domains, 7 zinc finger nuclease binding domains, 8 zinc finger nuclease binding domains, 9 zinc finger nuclease binding domains, 10 zinc finger nuclease binding domains, or more zinc finger binding domains.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In subsequent embodiments, the zinc finger nuclease binding domain comprising one or more zinc finger binding sequences is bound by a zinc finger binding protein, a meganuclease binding protein, a CRIPSR, or a TALEN binding protein.

In certain embodiments, the composition and methods described herein employ a meganuclease (homing endonuclease) binding protein or meganuclease DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) Science 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria *Ralstonia solanacearum* two genes, designated brg1 1 and hpx17 have been found that are homologous to the AvrBs3 family of *Xanthomonas* in the *R. solanacearum* biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication Nos. 20110239315, 20110145940 and 20110301073, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable di-residues at positions 12 and 13 with the identity of the contiguous nucleotides in the TAL-effector's target sequence (see Moscou and Bogdanove, (2009) Science 326:1501 and Boch et al (2009) Science 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Patent Publication No. 20110301073; Christian et al ((2010)<Genetics epub 10.1534/genetics.110.120717).

In other embodiments, the nuclease is a system comprising the CRISPR (Clustered Regularly Interspaced Short Palindromic Repeats)/Cas (CRISPR Associated) nuclease system. The CRISPR/Cas is a recently engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA next to a protospacer adjacent motif (PAM) NGG. Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence adjacent to a PAM (see Jinek et al (2012) *Science* 337, p. 816-821, Jinek et al, (2013), *eLife* 2:e00471, and David Segal, (2013) *eLife* 2:e00563). Thus, the CRISPR/Cas system can be engineered to create a DSB at a desired target in a genome, and repair of the DSB can be influenced by the use of repair inhibitors to cause an increase in error prone repair.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of five or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from a particular endonuclease or exonuclease. Exemplary endonucleases from which a cleavage domain can be derived include, but are not limited to, certain restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of DNA sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey'" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

In an embodiment the polynucleotide donor cassette comprises an analytical domain. In other embodiments the analytical domain comprises a specific polynucleotide sequence. Examples of specific polynucleotide sequences include, but are not limited to SEQ ID NO:142 and SEQ ID NO:143. In various embodiments, sequences with at least 90% sequence identity to the specific polynucleotide sequences of SEQ ID NO:142 and SEQ ID NO:143 are disclosed herein. In other embodiments, sequences with at least 95% sequence identity to the specific polynucleotide sequences of SEQ ID NO:142 and SEQ ID NO:143 are disclosed herein. In other embodiments, sequences with at least 97% sequence identity to the specific polynucleotide sequences of SEQ ID NO:142 and SEQ ID NO:143 are disclosed herein. In yet other embodiments, sequences with at least 99% sequence identity to the specific polynucleotide sequences of SEQ ID NO:142 and SEQ ID NO:143 are disclosed herein.

In an embodiment the analytical domain comprises a guanine and cytosine ratio of 40 to 60%. In other embodiments the analytical domain comprises a guanine and cytosine ratio of 42.25 to 57.5%. In other embodiments the analytical domain comprises a guanine and cytosine ratio of 45 to 55%. In another embodiment the analytical domain comprises a guanine and cytosine ratio of 47.75 to 52.25%. The ratio of guanine and cytosine content over a region comprising a polynucleotide sequence can be calculated by counting the number of guanine and cytosine residues in the polynucleotide sequence and dividing this number by the total number of base pairs in the stretch of the polynucleotide sequence and then multiplying the result by 100 to determine the percentage of guanine and cytosine for the polynucleotide sequence. Primers that comprise a ratio of guanine to cytosine of 40-60% result in more stable binding with template DNA during PCR amplifications. However, DNA molecules with a ratio of guanine to cytosine of greater than 60% are difficult to amplify via PCR, as such sequences may form stem loop, dimer, and other secondary structures.

Melting temperature (Tm) is defined as the temperature at which half of the DNA strands are in the double-helical state and half are in the random coil states. The melting temperature can depend on variables including the length of the molecule, the specific nucleotide sequence composition of that molecule and the molarity of the salt and the nucleic acid in the solution. Duplex stability and melting temperature are important in nucleic acid amplification where thermocycling may be involved. During such thermocycling steps, the temperature is raised high enough above the melting temperature so that duplexes of the target nucleic acid and its complement are dissociated. In subsequent steps of reannealing the temperature is brought to below the melting temperature such that duplexes of the target nucleic acid and primer(s) and/or probe(s) are able to form, while still remaining high enough to avoid non-specific hybridization. Melting temperature and how to measure it is thoroughly described in the art. See for example, Nucleic Acids Research (1990) 18, 6409-6412 and Bioinformatics, V. 12(12), pp. 1226-1227. Theoretical or empirical models that relate duplex stability to nucleotide sequence can be used to predict melting temperatures for nucleic acids. For example, Proc. Natl. Acad. Sci: U.S.A. 1986, 83:3746-3750, Biochemistry 1996, 35:3555-3562; and Proc. Natl. Acad Sci. U.S.A. 1998, 95:1460-1465 describe a model for predicting melting temperature that is widely used in the art and is known as the "nearest neighbour model". This model takes account of both the length of the oligonucleotide and the sequence of the bases within it.

The predicted melting temperature refers to the theoretically calculated melting temperature of an oligonucleotide that has not been conjugated with any moieties. It is usually an estimate of the actual melting temperature of an oligonucleotide and is based on the sequence of the oligonucleotide typically without considering the effect of any labels and any associated linkers and the like. Given the exact sequence of an oligonucleotide, the melting temperature of the oligonucleotide can be predicted as discussed above. The predicted melting temperature according to the present invention is calculated, in one embodiment, using the nearest neighbour model. In a further embodiment, the predicted melting temperature according to the present invention is calculated using the nearest neighbour thermodynamic theory using SantaLucia values (SantaLucia, J., Jr. (1998) Proc. Natl. Acad. Sci. U.S.A. (1998) 95, 1460-1465). The SantaLucia values are contained in various computer programs that can be used to predict melting temperatures. In one embodiment, the "Beacon Designer" software package is used. In one embodiment, the SantaLucia values are used with the following reaction conditions; nucleic acid concentration of 0.25 nM; monovalent ion concentration of 50 mM; free magnesium ion concentration of 5 mM; total $Na^+$ equivalent of 332.84 mM; and temperature for free energy calculations of 25° C. Regardless of the choice of the particular software programs or methodologies used, the same software program or methodology is desirably used, suitably, with its default settings, to ascertain the predicted melting temperatures of the primer(s) and the probe(s) used in the present invention.

The terms "minimum free energy" (MFE), "free energy," and "Gibbs free energy" are used herein interchangeably. The Gibbs free energy is a thermodynamic quantity that is the difference between the enthalpy and the product of the absolute temperature and the entropy of a system. Gibbs free energy is the capacity of a system to do non-mechanical work and ΔG measures the non-mechanical work done on it. (Perrot, Pierre. *A to Z of Thermodynamics*. Oxford University Press (1998)). The Gibbs free energy is defined as G=H−TS, where H is the enthalpy, T is temperature and S is the entropy (H=U+pV, where p is the pressure and V is the volume).

It is generally considered that all systems strive to achieve a minimum free energy. Thus, when the change in Gibbs free energy, ΔG, is negative then a reaction is favored and energy is released. The amount of energy released is equal to the maximum amount of work that can be performed as a result of that particular chemical reaction. When conditions result in a change in Gibbs free energy, ΔG, that is positive then energy must be added to the system to make the reaction proceed. In isothermal, isobaric systems, Gibbs free energy is a representative measure of the competing effects of enthalpy and entropy that are involved in a thermodynamic process. Thus, Gibb free energy can be consider to be a dynamic quantity.

It is noted that the measurement of free energy can be biased by nucleotide sequence length. Longer nucleotide sequences have a greater range of free energies than short nucleotide sequences. Thus, nucleotide sequences of variable length can be compared by normalizing the free energy calculation (kcal/mol) by dividing the free energy by the sequence length (i.e., the mean free energy=ΔG/length of nucleotide sequence (kcal/mol/base pair)).

Accordingly, as used herein, minimum free energy (i.e., free energy, Gibbs free energy) identifies the value for the structure found by thermodynamic optimization (i.e., an implementation of the Zuker algorithm (M. Zuker and P. Stiegler, *Nucleic Acids Research* 9:133-148 (1981)) that has the lowest free energy value (i.e., Gibb's free energy; AG (kcal/mol); AG/length of nucleotide sequence (kcal/mol/base pair)). The Gibb's free energy of a sequence can be calculated using, for example, the RNAfold™ or PRIMER EXPRESS™ (Version 1.0, Applied Biosystems, Foster City, Calif.) or mFOLD™ software (now UNIFold™) (IDT, San Jose, Calif.) program as known by those of skill in the art. (See, e.g., Id., Hofacker et al. *Monatshefte f Chemie* 125: 167-188 (1994); McCaskill J S. Biopolymers 29 (6-7):1105-19. (1990); and Hofacker et al. *Bioinformatics* 22 (10): 1172-6 (2006)).

In an embodiment the analytical domain comprises a polynucleotide that does not contain a plurality of repetitive sequences, wherein the repetitive sequence is at least 9 Bp in length. In some embodiments a plurality or repetitive sequences comprises 2, 3, 4, 5, 6, 7, 8, 9, 10, or more polynucleotide fragments of at least 9 Bp in length. In an embodiment a first polynucleotide sequence constitutes a repetitive sequence when a second polynucleotide sequence comprising the same sequence is located directly downstream of the first polynucleotide sequence (e.g. a first polynucleotide sequence comprises 5'-gaaaaataacaa-3', this polynucleotide sequence constitutes a repetitive sequence when a second polynucleotide sequence (underlined) comprising the same sequence is located directly downstream of the first polynucleotide sequence 5'-gaaaaataacaa gaaaaataacaa-3'). In an embodiment, the analytical domain comprises a polynucleotide that does not contain a plurality of such repetitive sequences.

In an embodiment an analytical domain comprises a polynucleotide that does not contain a series of identical base pair sequences greater than 9 Bp in length. Identical base pairs are any number of base pairs, greater than 9 Bp, of the same purine (adenine or guanine) or pyrimidine (cytosine or thymine) base pair that come one after another in spatial or temporal succession. Accordingly, a stretch of nucleotides such as; 5'-AAAAAAAAA-3', 5'-GGGGGGGGG-3', 5'-CCCCCCCCC-3', or 5'-TTTTTTTTT-3' would comprise a series of nine identical base pairs. In an embodiment, a series of identical base pair sequences may be greater than 9 Bp, 10 Bp, 11 Bp, 12 Bp, 13 Bp, 14 Bp, 15 Bp or more Bp in length.

In other embodiments the analytical domain of the polynucleotide donor cassette comprises one or more restriction enzyme sequences. A restriction enzyme is an enzyme capable of cleaving DNA into fragments. Cleavage of large molecular weight genomic DNA by a restriction enzyme into fragments of lower molecular weight fragments allows for more efficient isolation and manipulation of the DNA fragments for subsequent analysis.

Restriction enzyme digestions, also referenced as restriction endonuclease digestions, are performed when a nuclease enzyme is used to cleave the polynucleotide sequences. There are numerous restriction enzymes available to those skilled in the art. As described at www.neb.com/nebecomm/tech_reference/restriction_enzymes/overview.asp, four classifications are used to characterize restriction enzymes. These classifications are made on the basis of subunit composition, cleavage position, sequence specificity and cofactor requirements.

Type I enzymes randomly cut DNA at locations which are a distance from the recognition/binding sequence (>1,000 bp away). The recognition sites which are bound by a Type I enzyme are asymmetrical. As a result these enzymes are not used for gene cloning because these enzymes do not produce discrete restriction fragments or distinct gel-banding patterns. Type I enzymes are multifunctional and the different subunits which comprise a Type I restriction enzyme are responsible for different activities (i.e. subunit HsdR encodes restriction, subunit HsdM encodes methylation of DNA, and subunit HsdS encodes specificity of the recognition sequence).

Type II enzymes digest DNA at positions located within close proximity of the recognition sequences. These enzymes function as a dimer, wherein a subunit binds to the sense strand and a second copy of the subunit binds to the antisense strand at a palindromic sequence which is typically between 4-8 nucleotides in length. The Type II dimer that binds to the DNA can be either a homodimer which bind to symmetric DNA sequences, or a heterodimer which binds to asymmetric DNA sequences. The enzymes can recognize either continuous sequences or discontinuous sequences. Type II enzymes are commercially available and commonly used for DNA analysis and gene cloning. Widespread usage of these enzymes is a result of distinct restriction fragments which are produced and can be resolved on an agarose gel.

Type II enzymes are a collection of unrelated proteins which are highly divergent in amino acid sequence similarity. Type II enzymes have been divided into subcategories which are labeled using a letter suffix. Type IIB restriction enzymes are multimers that contain more than one subunit. These enzymes cut both sides of the recognition sequence, thereby resulting in removal of the recognition sequence. Type IIE and Type IIF restriction enzymes cleave DNA following interaction with two copies of their recognition sequence. Type IIG restriction enzymes are comprised of a single subunit. The N-terminal portion of the enzyme possesses a DNA cleavage domain and DNA modification domain. The C-terminal portion of the enzyme possesses a DNA sequence binding domain. These enzymes cleave outside of their recognition sequence. Type IIM restriction enzymes recognize and cut methylated DNA. Type IIS restriction enzymes function as a dimer and cleave DNA at a location which is outside of the non-palindromic asymmetric recognition sites. These enzymes are comprised of two distinct domains, one for DNA binding and the other for DNA cleavage.

Type III enzymes are combination restriction-and-modification enzymes. These enzymes recognize two separate non-palindromic sequences and cleave outside of their recognition sequences. Type III enzymes require two recognition sequences in opposite orientations within the same DNA molecule to accomplish cleavage.

Type IV enzymes recognize methylated DNA. Examples include the McrBC and Mrr systems of *E. coli*.

In an embodiment, the analytical domain of the polynucleotide donor cassette comprises one or more primer binding sequences. The term "primer binding sequence" refers to a region of the analytical domain or any other polynucleotide sequence, typically a sequence flanking a target region and/or an amplicon that can serve directly, or by virtue of its complement, as the template upon which a primer can anneal for any suitable primer extension reaction or amplification reaction known in the art, for example but not limited to, PCR. It will be appreciated by those of skill in the art that when two primer-binding sites are present on a single polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

A primer can be designed to bind to an analytical domain comprising secondary structure that is calculated with a free energy (ΔG) of −1 to −18 kcal/mole. In an embodiment, a primer can be designed with a melting temperature (Tm) of at least 10° C. greater than the region of an analytical domain comprising secondary structure with a free energy (ΔG) of −1 to −18 kcal/mole as calculated using Markham, N. R. & Zuker, M. (2008) UNAFold: software for nucleic acid folding and hybridization. In Keith, J. M., editor, *Bioinformatics, Volume II. Structure, Function and Applications*, number 453 in *Methods in Molecular Biology*, chapter 1, pages 3-31. Humana Press, Totowa, N.J. ISBN 978-1-60327-428-9.

In an embodiment the analytical domain of the polynucleotide donor cassette of comprises one or more homology arm sequences. Subsequent embodiments of the one or more homology arm sequences are comprised of lengths of 50 to 100 base pairs. Homology arms comprised of random stretches of nucleotides can be readily designed and synthesize for various applications. The universal polynucleotide donor sequences may comprise one or more homology arms that are employed for homologous integration of a polynucleotide within the host genome. In some embodiments, the homology arm is targeted by introducing a double strand break within or next to the homology arm and integrating a second polynucleotide that may comprise a gene expression cassette comprising a transgene within the homology arm region. Typically, the integration of the second polynucleotide occurs via homologous recombination directed repair.

In one embodiment the homology arm region shares at least 80, 90, 93, 95, 99 or 100% sequence identity with an optimal genomic loci. In one embodiment the embodiment the homology arm region shares at least 80, 90, 93, 95, 99, or 100% sequence identity with an optimal genomic loci of a plant cell. In one embodiment the optimal genomic loci is a nongenic monocot or dicot sequence that is hypomethylated, expressable, exemplifies evidence of recombination and is located in proximal location to a genic region in the genome of a plant.

In one embodiment the optimal genomic loci is a hypomethylated nongenic sequence having the following properties or characteristics:
 a) the level of methylation of said nongenic sequence is 1% or less;
 b) the nongenic sequence shares less than 40% sequence identity with any other sequence contained in the genome;
 c) the nongenic sequence shares less than 40% sequence identity with any other sequence contained in the genome;
 d) the nongenic sequence is located within a 40 Kb region of a known or predicted expressive coding sequence; and,
 e) the nongenic sequence exhibits a recombination frequency within the genome of greater than 0.00041 cM/Mb.

In one embodiment the optimal genomic loci is a hypomethylated nongenic sequence having 1, 2, 3, 4 or 5 of the following properties or characteristics:
 a) has a known or predicted gene coding sequence within 40 Kb of said nongenic sequence;
 b) has a sequence comprising a 2 Kb upstream and/or 1 Kb downstream of a known gene within 40 Kb of one end of said nongenic sequence;
 c) does not contain greater than 1% DNA methylation within the nongenic sequence;
 d) does not contain a 1 Kb sequence having greater than 40% sequence identity to any other sequence within the genome; and
 e) exemplifies evidence of recombination at a recombination frequency of greater than 0.00041 cM/Mb.

In accordance with one embodiment the selected nongenic sequence comprises 2, 3, 4, 5, 6, 7 or 8 of the following characteristics:
 a) the nongenic sequence does not contain a methylated polynucleotide;
 b) the nongenic sequence exhibits a 0.00041 to 62.42 cM/Mb rate of recombination within the genome;
 c) the nongenic sequence exhibits a 0 to 0.962 level of nucleosome occupancy of the genome;
 d) the nongenic sequence shares less than 40% sequence identity with any other 1 Kb sequence contained in the genome;
 e) the nongenic sequence has a relative location value from 0.00373 to 0.99908, representing the ratio of genomic distance from a chromosomal centromere;
 f) the nongenic sequence has a guanine/cytosine percent content range of 25.17 to 68.3%;
 g) the nongenic sequence is located proximally to a genic sequence; and,
 h) a 1 Mb region of genomic sequence comprising said nongenic sequence, comprises one or more nongenic sequences.

In an embodiment the analytical domain of the polynucleotide donor cassette comprises a sequence that does not encode a peptide.

In an embodiment the analytical domain of the polynucleotide donor cassette comprises a sequence that does encode a peptide. To express a peptide, nucleotide sequences encoding the peptide sequence are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; 3$^{rd}$ ed., 2001); Kriegler, *Gene Transfer and Expression: A Laboratory Manual* (1990); and *Current Protocols in Molecular Biology* (Ausubel et al., supra.). Bacterial expression systems for expressing a peptide are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

In an embodiment the polynucleotide donor cassette comprises a gene expression cassette comprising a transgene. The gene expression cassette typically contains a transcription unit or expression cassette that contains all the additional elements required for the expression of the nucleic acid in host cells, either prokaryotic or eukaryotic. A typical gene expression cassette thus contains a promoter operably linked, e.g., to a nucleic acid sequence encoding the protein, and signals required, e.g., for efficient polyadenylation of the transcript, transcriptional termination, ribosome binding sites, or translation termination. Additional elements of the cassette may include, e.g., enhancers and heterologous splicing signals.

In an embodiment the gene expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp 7831-7846(nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al. Nucleic Acids Res. 17:7891-7903 (1989); Joshi et al. Nucleic Acid Res. 15:9627-9639 (1987).

In other embodiments, the gene expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154: 9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987). The construct can also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In an embodiment the gene expression cassette of the polynucleotide donor sequence comprises a promoter. The promoter used to direct expression of a peptide encoding nucleic acid depends on the particular application. For example, a strong constitutive promoter suited to the host cell is typically used for expression and purification of proteins. Non-limiting examples of preferred plant promoters include promoter sequences derived from *A. thaliana* ubiquitin-10 (ubi-10) (Callis, et al., 1990, *J. Biol. Chem.*, 265:12486-12493); *A. tumefaciens* mannopine synthase (Amas) (Petolino et al., U.S. Pat. No. 6,730,824); and/or Cassava Vein Mosaic Virus (CsVMV) (Verdaguer et al., 1996, Plant Molecular Biology 31:1129-1139).

In methods disclosed herein, a number of promoters that direct expression of a gene in a plant can be employed. Such promoters can be selected from constitutive, chemically-regulated, inducible, tissue-specific, and seed-preferred promoters.

Constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) Plant Mol. Biol. 18:675-689); pEMU promoter (Last et al. (1991) Theor. Appl. Genet. 81:581-588); ALS promoter (U.S. Pat. No. 5,659,026); Maize Histone promoter (Chabouté et al. Plant Molecular Biology, 8:179-191 (1987)); and the like.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in embodiments of the instant disclosure. See Ward et al. Plant Mol. Biol. 22: 361-366 (1993). Exemplary inducible promoters include ecdysone receptor promoters (U.S. Pat. No. 6,504,082); promoters from the ACE1 system which respond to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); or promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-la promoter, which is activated by salicylic acid (see Ono S, Kusama M, Ogura R, Hiratsuka K., "Evaluation of the Use of the Tobacco PR-la Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol.

Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as P5CS (Zang et al. (1997) Plant Sciences 129:81-89); cold-inducible promoters, such as, cor15a (Hajela et al. (1990) Plant Physiol. 93:1246-1252), cor15b (Wilhelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), ci21A (Schneider et al. (1997) Plant Physiol. 113:335-45); drought-inducible promoters, such as Trg-31 (Chaudhary et al (1996) Plant Mol. Biol. 30:1247-57), rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); and heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the *Agrobacterium* pMAS promoter (Guevara-Garcia et al. (1993) Plant J. 4(3):495-505) and the *Agrobacterium* ORF13 promoter (Hansen et al., (1997) Mol. Gen. Genet. 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al. 1989. *The Plant Cell Vol.* 1, 839-853), and the maize globulin-1 gene, Belanger, et al. 1991 *Genetics* 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al. 1994. T-DNA tagging of a seed coat-specific cryptic promoter in tobacco. Plant J. 4: 567-577), the P-gene promoter from corn (Chopra et al. 1996. Alleles of the maize P gene with distinct tissue specificities encode Myb-homologous proteins with C-terminal replacements. Plant Cell 7:1149-1158, Erratum in Plant Cell. 1997, 1:109), the globulin-1 promoter from corn (Belenger and Kriz. 1991. Molecular basis for Allelic Polymorphism of the maize Globulin-1 gene. Genetics 129: 863-972), and promoters that direct expression to the seed coat or hull of corn kernels, for example the pericarp-specific glutamine synthetase promoter (Muhitch et al., 2002. Isolation of a Promoter Sequence From the Glutamine Synthetase$_{1-2}$ Gene Capable of Conferring Tissue-Specific Gene Expression in Transgenic Maize. Plant Science 163: 865-872).

A gene expression cassette may contain a 5' leader sequence. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987).

The construct may also contain sequences that enhance translation and/or mRNA stability such as introns. An example of one such intron is the first intron of gene II of the histone H3.III variant of *Arabidopsis thaliana*. Chaubet et al. Journal of Molecular Biology, 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (see Lebrun et al. U.S. Pat. No. 5,510,417), *Zea mays* Brittle-1 chloroplast transit peptide (Nelson et al. Plant Physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267(26):18999-9004) and the like. In addition, chimeric chloroplast transit peptides are known in the art, such as the Optimized Transit Peptide (see, U.S. Pat. No. 5,510, 471). Additional chloroplast transit peptides have been described previously in U.S. Pat. Nos. 5,717,084; 5,728,925. One skilled in the art will readily appreciate the many options available in expressing a product to a particular organelle. For example, the barley alpha amylase sequence is often used to direct expression to the endoplasmic reticulum. Rogers, J. Biol. Chem. 260:3731-3738 (1985).

In an embodiment the polynucleotide donor cassette comprises a transgene. Some embodiments herein provide a transgene encoding a polypeptide comprising a gene expression cassette. Such a transgene may be useful in any of a wide variety of applications to produce transgenic plants. Particular examples of a transgene comprising a gene expression cassette are provided for illustrative purposes herein and include a gene expression comprising a trait gene, an RNAi gene, or a reporter/selectable marker gene.

In engineering a gene for expression in plants, the codon bias of the prospective host plant(s) may be determined, for example, through use of publicly available DNA sequence databases to find information about the codon distribution of plant genomes or the protein coding regions of various plant genes. Once an optimized (e.g., a plant-optimized) DNA sequence has been designed on paper, or in silico, actual DNA molecules may be synthesized in the laboratory to correspond in sequence precisely to the designed sequence. Such synthetic nucleic acid molecule molecules can be cloned and otherwise manipulated exactly as if they were derived from natural or native sources.

In an embodiment, a transgene to be expressed is disclosed in the subject application. The gene expression cassette may comprise a reporter/selectable marker gene, a trait gene, or an RNAi gene. Examples of a selectable marker gene, a trait gene, and an RNAi gene are further provided below. The methods disclosed in the present application are advantageous in that they provide a method for selecting germline transformants that is not dependent on the specific function of the protein product, or other function, of the transgene.

Transgenes or Coding Sequence that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al. U.S. Pat. No. 6,573,099.

Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., 1988 EMBO J. 7:1241), which is also known as AHAS enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform Chlamydomonas. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

Genes that Confer or Contribute to a Value-Added Trait (A) Modified fatty acid metabolism, for example, by transforming maize or Brassica with an antisense gene or stearoyl-ACP desaturase to increase stearic acid content of the plant (Knultzon et al., 1992) Proc. Nat. Acad. Sci. USA 89:2624.

(B) Decreased phytate content
(1) Introduction of a phytase-encoding gene, such as the Aspergillus niger phytase gene (Van Hartingsveldt et al., 1993 Gene 127:87), enhances breakdown of phytate, adding more free phosphate to the transformed plant.
(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, Streptococcus mucus fructosyltransferase gene (Shiroza et al., 1988) J. Bacteriol. 170:810, Bacillus subtilis levansucrase gene (Steinmetz et al., 1985 Mol. Gen. Genel. 200:220), Bacillus licheniformis α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

In a subsequent embodiment, the transgene comprises a reporter gene. In various embodiments the reporter gene is selected from the group consisting of a yfp gene, a gus gene, a rfp gene, a gfp gene, a kanamycin resistance gene, an aad-1 gene, an aad-12 gene, a pat gene, and a glyphosate tolerant gene. Reporter or marker genes for selection of transformed cells or tissues or plant parts or plants may be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, 1983; Meijer et al., Plant Mol. Biol. 16:807-820, 1991); neomycin phosphotransferase, which confers resistance to the aminoglycosides neomycin, kanamycin and paromycin (Herrera-Estrella, EMBO J. 2:987-995, 1983 and Fraley et al. Proc. Natl. Acad. Sci USA 80:4803 (1983)); hygromycin phosphotransferase, which confers resistance to hygromycin (Marsh, Gene 32:481-485, 1984; see also Waldron et al., Plant Mol. Biol. 5:103-108, 1985; Zhijian et al., Plant Science 108:219-227, 1995); trpB, which allows cells to utilize indole in place of tryptophan; hisD, which allows cells to utilize histinol in place of histidine (Hartman, Proc. Natl. Acad. Sci., USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from Aspergillus terreus, which confers resistance to Blasticidin S (Tamura, Biosci. Biotechnol. Biochem. 59:2336-2338, 1995).

Additional selectable markers include, for example, a mutant acetolactate synthase, which confers imidazolinone or sulfonylurea resistance (Lee et al., EMBO J. 7:1241-1248, 1988), a mutant psbA, which confers resistance to atrazine (Smeda et al., Plant Physiol. 103:911-917, 1993), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, 1983); streptomycin (Jones et al., Mol. Gen. Genet. 210:86-91, 1987); spectinomycin (Bretagne-Sagnard et al., Transgenic Res. 5:131-137, 1996); bleomycin (Hille et al., Plant Mol. Biol. 7:171-176, 1990); sulfonamide (Guerineau et al., Plant Mol. Biol. 15:127-136, 1990); bromoxynil (Stalker et al., Science 242:419-423, 1988); glyphosate (Shaw et al., Science 233:478-481, 1986); phosphinothricin (DeBlock et al., EMBO J. 6:2513-2518, 1987), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) Gene 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al, Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Scheffler et al. Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al, Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PHI-YFP™ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al. (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

In a subsequent embodiment, the analytical domain of the polynucleotide donor comprises SEQ ID NO:142 or SEQ ID NO:143. Modifications and derivatives of SEQ ID NO:142 or SEQ ID NO:143 are considered in purview of the subject disclosure. Such modifications and derivatives of SEQ ID NO:142 or SEQ ID NO:143 can result in sequences that share specific levels of sequence identity. In various embodiments, sequences with 1, 2, 3, 4, 5, 6, 7, 8, 9 or 10 Bp modifications to SEQ ID NO:142 are disclosed herein. In other embodiments, sequences with 1, 2, 3, 4, 5, 6, 7, 8, 9 or 10 Bp modifications to SEQ ID NO:143 are disclosed herein.

In other embodiments the plasmid domain of the universal polynucleotide donor cassette comprises plasmid sequences. A plasmid or vector can be described or referred to as prokaryotic vectors, shuttle vectors, insect vectors, or eukaryotic vectors. Typically, plasmids are extra-chromosomal elements, often circular DNA, that are comprised of an origin of replication and a selectable marker gene. At times, it may be preferable to have a plasmid that is functional in *E. coli* (e.g., DNA sequence analysis, construction of inserts, obtaining quantities of nucleic acids). The particular plasmid used for the universal polynucleotide donor can be selected with regard to the intended use (e.g., expression in plants, animals, bacteria, fungus, and protozoa). Standard bacterial and animal expression plasmids are known in the art and are described in detail, for example, U.S. Patent Publication 20050064474A1 and International Patent Publications WO 05/084190, WO05/014791 and WO03/080809.

In other embodiments the plasmid domain of the polynucleotide donor cassette comprises pUC19 plasmid sequences. pUC19 is a small double stranded DNA circle. The plasmid contains high copy number origin of replication that is capable of bacterial replication and contains a multiple cloning site. See Yanisch-Perron, C., Vieira, J. and Messing, J. (1985). Gene. 33, 103-119. Other plasmids are known and commonly used in the art. For example, pUC18, pBR322, pBR325, pBR328, pACYC184, pAT153, pUC118, and pUC119 are plasmids commonly known in the art.

In other embodiments the plasmid domain of the polynucleotide donor cassette comprises a high-copy number origin of replication. Subsequent embodiments of high-copy number origins of replication include a ColE1 origin of replication. The term "origin of replication" or "ORI" as used herein is intended to encompass regions of nucleotides that are necessary for replication of a plasmid. Some of examples of origins of replications: nucleotides 1766-3148 of pBR322; nucleotides 1667-2892 of ColE1; and nucleotides 580-1407 of pACC184. In an embodiment the plasmid domain of the polynucleotide donor cassette may comprise two or more different origins of replication.

In embodiments the plasmid domain comprises a selectable marker. Subsequent embodiments of plasmid domain selectable markers are selected from the group consisting of a kanamycin selectable marker, an ampicillin selectable marker, a spectinomycin selectable marker, a chloramphenicol selectable marker, and a rifampicin selectable marker. Suitable selectable markers are antibiotic resistance genes. Other selectable markers can include scorable marker genes for example beta-glucuronidase (GUS) (Kononov, et al., *Plant J.* 11, 945-957, 1997), can provide a means to detect the presence of backbone DNA, but do not provide a means to select against the cells that contain them and the assay is tissue destructive. Negative selectable marker genes that are conditional lethal can also be used in the backbone DNA. Representative examples of other conditional lethal gene products include: *E. coli* guanine phosphoribosyl transferase that converts thioxanthine into toxic thioxanthine monophosphate (Besnard et al., Mol. Cell. Biol. 7:4139-4141, 1987); alkaline phosphatase, which will convert inactive phosphorylated compounds such as mitomycin phosphate and doxorubicin-phosphate to toxic dephosphorylated compounds; fungal (e.g. *Fusarium oxysporum*) or bacterial cytosine deaminase (codA) that will convert 5-fluorocytosine to the toxic compound 5-fluorouracil (Mullen, PNAS 89:33, 1992); carboxypeptidase G2 which will cleave the glutamic acid from para-N-bis(2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds (see generally, Vrudhula et al., J. of Med. Chem. 36(7):919-923, 1993; Kern et al., Canc. Immun. Immunother. 31(4):202-206, 1990); and phosphonate monoester hydrolase, pehA (U.S. Pat. No. 5,254,801). However, exogenous substrates must be added in order to provide the toxic product that is lethal to the cell containing the backbone DNA. The present invention does not require adding additional substrates to the culture media or exogenously treating the plant culture cells with a substrate as needed for the conditional lethal gene product.

In another embodiment of the present disclosure, a method for targeted integration of the universal polynucleotide donor cassette within the genome of a plant cell is disclosed. In certain embodiments, a site specific DNA binding nuclease comprising at least one DNA-binding domain and at least one nuclease domain, wherein the at least one DNA-binding domain binds to a target site within the genome of the plant cell is expressed. In other embodiments the plant cell is contacted with the universal polynucleotide donor cassette. In further embodiments the target site within the genome of the plant cell is cleaved with the site specific DNA binding nuclease. In yet another embodiment the universal polynucleotide donor cassette is integrated into the target site within the genome of the plant cell.

In an embodiment the targeted integration of the universal polynucleotide donor cassette within the genome of a plant cell via a homology directed repair mechanism is disclosed. In another embodiment the targeted integration of the universal polynucleotide donor cassette within the genome of a plant cell via a non-homologous end joining directed repair mechanism is disclosed.

The donor molecules disclosed herein are integrated into a genome of a cell via targeted, homology-independent methods. For such targeted integration, the genome is cleaved at a desired location (or locations) using a nuclease, for example, a fusion between a DNA-binding domain (e.g., zinc finger binding domain or TAL effector domain is engineered to bind a target site at or near the predetermined cleavage site) and nuclease domain (e.g., cleavage domain or cleavage half-domain). In certain embodiments, two fusion proteins, each comprising a DNA-binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two DNA-binding domains. One or both of the DNA-binding domains can be engineered. See, also, U.S. Pat. No. 7,888,121; U.S. Patent Publication 20050064474 and International Patent Publications WO05/084190, WO05/014791 and WO 03/080809.

The nucleases as described herein can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

Following the introduction of a double-stranded break in the region of interest, the transgene is integrated into the region of interest in a targeted manner via non-homology dependent methods (e.g., non-homologous end joining (NHEJ)) following linearization of a double-stranded donor molecule as described herein. The double-stranded donor is preferably linearized in vivo with a nuclease, for example one or more of the same or different nucleases that are used to introduce the double-stranded break in the genome. Synchronized cleavage of the chromosome and the donor in the cell may limit donor DNA degradation (as compared to linearization of the donor molecule prior to introduction into the cell). The nuclease target sites used for linearization of the donor preferably do not disrupt the transgene(s) sequence(s).

The transgene may be integrated into the genome in the direction expected by simple ligation of the nuclease overhangs (designated "forward" or "AB" orientation) or in the alternate direction (designated "reverse" or "BA" orientation). In certain embodiments, the transgene is integrated following accurate ligation of the donor and chromosome overhangs. In other embodiments, integration of the transgene in either the BA or AB orientation results in deletion of several nucleotides.

IV. Assays for Detection of the Universal Donor Polynucleotide

Various assays can be employed to detect the universal donor polynucleotide described in certain embodiments of the disclosure. The following techniques are useful in a variety of situations, and in one embodiment, are useful in detecting the presence of a nucleic acid molecule and/or the polypeptide encoding a transgene in a plant cell. For example, the presence of the molecule can be determined in a variety of ways, including using a primer or probe of the sequence, ELISA assay to detect the encoded protein, a Western blot to detect the protein, or a Northern or Southern blot to detect RNA or DNA. Enzymatic assays for detecting the universal donor polynucleotide can be employed. Further, an antibody which can detect the presence of the universal donor polynucleotide protein can be generated using art recognized procedures. Additional techniques, such as in situ hybridization, enzyme staining, and immunostaining, also may be used to detect the presence or expression of the recombinant construct in specific plant organs and tissues. The transgene contained in the universal donor polynucleotide may be selectively expressed in some tissues of the plant or at some developmental stages, or the transgene contained in the universal donor polynucleotide may be expressed in substantially all plant tissues, substantially along its entire life cycle. However, any combinatorial expression mode is also applicable.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with $^{32}$P (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with $^{32}$P (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

In the Western analysis, instead of isolating DNA/RNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" Molecular Breeding 3:291-306 (1997); Towbin et al, (1979) "Electrophoretic transfer of proteins from polyacrylamide gels to nitrocellulose sheets: procedure and some applications" Proc Natl Acad Sci USA 76(9): 4350-4354; Renart et al. "Transfer of proteins from gels to diazobenzyloxymethyl-paper and detection with antisera: a method for studying antibody specificity and antigen structure" Proc Natl Acad Sci USA 76(7): 3116-3120.

The universal donor polynucleotide, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject disclosure. Mutations, insertions, and deletions can be produced in a given primer by methods known to an ordinarily skilled artisan.

Another example of method detection is the pyro sequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension. (This technique is used for initial sequencing, not for detection of a specific gene when it is known.)

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

The ELISA or enzyme linked immunoassay has been known since 1971. In general, antigens solubilized in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

Embodiments of the subject disclosure are further exemplified in the following Examples. It should be understood that these Examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1

Design of Zinc Fingers to Bind Genomic Loci in *Zea mays*

Zinc finger proteins directed against identified DNA sequences of the targetable *Zea mays* genomic loci were designed as previously described. See, e.g., Urnov et al., (2005) Nature 435:646-551. Exemplary target sequence and recognition helices are shown in Table 1 (recognition helix regions designs) and Table 2 (target sites). In Table 2, nucleotides in the target site that are contacted by the ZFP recognition helices are indicated in uppercase letters and non-contacted nucleotides are indicated in lowercase. Zinc Finger Nuclease (ZFN) target sites were designed for all of the 72 selected genomic loci in *Zea mays*. Numerous ZFP designs were developed and tested to identify the fingers which bound with the highest level of efficiency in a yeast proxy system with 72 different representative genomic loci target sites which were identified and selected in *Zea mays*. The specific ZFP recognition helices (Table 1) which bound with the highest level of efficiency to the zinc finger recognition sequences were used for targeting and integration of a donor sequence within the *Zea mays* genome.

TABLE 1

Zinc finger designs for the *Zea mays* selected genomic loci (N/A indicates "not applicable").

| pDAB Number | ZFP Number | F1 | F2 | F3 | F4 | F5 | F6 |
|---|---|---|---|---|---|---|---|
| 111879 | 111879 ZFN5 | SEQ ID NO: 1 QSGDLTR | SEQ ID NO: 2 RKDQLVA | SEQ ID NO: 3 RSDDLTR | SEQ ID NO: 4 TSSNRKT | SEQ ID NO: 5 RSDTLSE | SEQ ID NO: 6 ARSTRTN |
|  | 111879 ZFN7 | SEQ ID NO: 7 RSDSLSV | SEQ ID NO: 8 DRSNRKT | SEQ ID NO: 9 QSSHLTR | SEQ ID NO: 10 RSDALAR | SEQ ID NO: 11 RSDDLTR | SEQ ID NO: 12 DPSALRK |
| 111885 | 111885 ZFN1 | SEQ ID NO: 13 RSDNLSQ | SEQ ID NO: 14 ASNDRKK | SEQ ID NO: 15 ERGTLAR | SEQ ID NO: 16 RSDHLSR | SEQ ID NO: 17 ERGTLAR | SEQ ID NO: 18 QSGHLSR |
|  | 111885 ZFN2 | SEQ ID NO: 19 RSANLAR | SEQ ID NO: 20 DRSDLSR | SEQ ID NO: 21 RSDTLSQ | SEQ ID NO: 22 RSADLSR | SEQ ID NO: 23 DRSNLSR | SEQ ID NO: 24 NSRNLRN |
| 117404 | SIG115737_3 1v1 | SEQ ID NO: 25 RSDSLSV | SEQ ID NO: 26 DRSHLAR | SEQ ID NO: 27 DRSNLSR | SEQ ID NO: 28 RRSDLKR | SEQ ID NO: 29 RSDTLSE | SEQ ID NO: 30 QNATRIN |
|  | SIG115737_3 2v1 | SEQ ID NO: 31 QSGSLTR | SEQ ID NO: 32 QSGDLTR | SEQ ID NO: 33 RSDVLSE | SEQ ID NO: 34 TRNGLKY | N/A | N/A |

TABLE 1-continued

Zinc finger designs for the *Zea mays* selected genomic loci (N/A indicates "not applicable").

| pDAB Number | ZFP Number | F1 | F2 | F3 | F4 | F5 | F6 |
|---|---|---|---|---|---|---|---|
| 117408 | SIG120523_1 1v1 | SEQ ID NO: 35 RSDNLSR | SEQ ID NO: 36 DNSNRKT | SEQ ID NO: 37 QNAHRKT | SEQ ID NO: 38 QKATRIT | SEQ ID NO: 39 DRSHLTR | SEQ ID NO: 40 RSDDRKK |
|  | SIG120523_1 2v1 | SEQ ID NO: 41 ASKTRTN | SEQ ID NO: 42 QSGSLTR | SEQ ID NO: 43 LRHHLTR | SEQ ID NO: 44 QSAHLKA | N/A | N/A |
| 117400 | SIG115246_5 | SEQ ID NO: 45 QSGDLTR | SEQ ID NO: 46 ASHNLRT | SEQ ID NO: 47 DRSNLTR | SEQ ID NO: 48 QSSDLSR | SEQ ID NO: 49 DAGNRNK | N/A |
|  | SIG115246_6 | SEQ ID NO: 50 DRSDLSR | SEQ ID NO: 51 RSDNLTR | SEQ ID NO: 52 DRSHLSR | SEQ ID NO: 53 TSGNLTR | SEQ ID NO: 54 QSSDLSR | N/A |
| 117402 | SIG115636_1 v1 | SEQ ID NO: 55 QSSDLSR | SEQ ID NO: 56 HRSTRNR | SEQ ID NO: 57 RSDDLTR | SEQ ID NO: 58 DRSNLKA | SEQ ID NO: 59 DRSHLTR | SEQ ID NO: 60 QRSTLKS |
|  | SIG115636_2 v1 | SEQ ID NO: 61 RSDALSR | SEQ ID NO: 62 RSDDLTR | SEQ ID NO: 63 DRSHLTR | SEQ ID NO: 64 TSSNRKT | SEQ ID NO: 65 RSDTLSE | SEQ ID NO: 66 DRSHLAR |
| 117406 | SIG120417_1 1v1 | SEQ ID NO: 67 DRSARTR | SEQ ID NO: 68 QSGHLSR | SEQ ID NO: 69 QSGNLAR | SEQ ID NO: 70 RSDVLST | SEQ ID NO: 71 RYAYLTS | SEQ ID NO: 72 RRWTLVG |
|  | SIG120417_2 2v1 | SEQ ID NO: 73 RSDNLSQ | SEQ ID NO: 74 ASNDRKK | SEQ ID NO: 75 QSGDLTR | SEQ ID NO: 76 LKDTLRR | SEQ ID NO: 77 QSGNLAR | N/A |
| 117411 | SIG120621_1 5v1 | SEQ ID NO: 78 QSGDLTR | SEQ ID NO: 79 MQNYLSR | SEQ ID NO: 80 RSDHLSE | SEQ ID NO: 81 QNANRKT | SEQ ID NO: 82 RSADLTR | N/A |
|  | SIG120621_1 6v1 | SEQ ID NO: 83 RSDNLSE | SEQ ID NO: 84 QSANRTK | SEQ ID NO: 85 RSDALSR | SEQ ID NO: 86 DRSALAR | SEQ ID NO: 87 RSDHLSE | SEQ ID NO: 88 DSQNRIK |
| 117413 | SIG12078_11 v1 | SEQ ID NO: 89 QSGDLTR | SEQ ID NO: 90 DKGNLTK | SEQ ID NO: 91 RSADLTR | SEQ ID NO: 92 DRSHLAR | SEQ ID NO: 93 RSDTLSE | SEQ ID NO: 94 DRSNRKT |
|  | SIG12078_12 v1 | SEQ ID NO: 95 DRSNLSR | SEQ ID NO: 96 LRQDLKR | SEQ ID NO: 97 RSDHLSE | SEQ ID NO: 98 DRSALAR | SEQ ID NO: 99 DRSALSR | SEQ ID NO: 100 NRRGRWS |
| 117429 | SIG157315_1 v1 | SEQ ID NO: 101 RPYTLRL | SEQ ID NO: 102 HRSSLRR | SEQ ID NO: 103 RSDSLLR | SEQ ID NO: 104 WLSSLSA | SEQ ID NO: 105 QSGDLTR | SEQ ID NO: 106 DRSHLAR |
|  | SIG157315_2 v1 | SEQ ID NO: 107 DRSNLSR | SEQ ID NO: 108 LKQHLNE | SEQ ID NO: 109 LRHHLTR | SEQ ID NO: 110 QSGNLHV | SEQ ID NO: 111 TSGHLSR | N/A |

TABLE 2

Target site of *Zea mays* selected genomic loci.

| Locus ID | pDAB Name | ZFP Number and Binding Number Site (5'→3') | Target Site SEQ ID NO: | Optimal Genomic Loci SEQ ID NO: |
|---|---|---|---|---|
| optimal_loci_ 204637 | OGL1 | pDAB111879111879ZFN5: ctACTCCGT ATGCGAAGGCAcg | 112 | 210 |
| | | 111879ZFN7: taTTCGCGGTGGGACAC TTGat | 113 | |
| optimal_loci_2 04726 | OGL2 | pDAB111885111885ZFN1: ccGGAGCCGGGGCCTCC CAGgc | 114 | 211 |
| | | 111885ZFN2: atCGCGACGCGACGcGA CGAGac | 115 | |
| optimal_loci_1 56393 | OGL 12 | pDAB117404SIG115737_31v1: TGCATGCGCAGTA | 116 | 212 |
| | | SIG115737_32v1: ACACCGGCGCACGGCA CG | 117 | |
| optimal_loci_1 98387 | OGL 15 | pDAB117408SIG120523_11v1: AGAGGTGTAACC | 118 | 213 |
| | | SIG120523_12v1: TCGGGCACAAGAAACG AG | 119 | |
| optimal_loci_3 1710 | OGL 08 | pDAB117400SIG115246_5: TACGCTGACAATGCA | 120 | 214 |
| | | SIG115246_6: CCAGCTGATGGAGAGG AC | 121 | |
| optimal_loci_6 4542 | OGL 11 | pDAB117402SIG115636_1v1: AGAGCAGGCGAG | 122 | 215 |
| | | SIG115636_2v1: AGCAAAGTGAGTAGTT | 123 | |
| optimal_loci_1 97372 | OGL1 4 | pDAB117406SIG120417_11v1: TGGATGGAAGGAATC | 124 | 216 |
| | | SIG120417_12v1: GAAGCTACATCCCAG | 125 | |
| optimal_loci_2 32228 | OGL 16 | pDAB117411SIG120621_15v1: TACGCGCAACGGAACG CA | 126 | 217 |
| | | SIG120621_16v1: CACCGGTGTCGTGTAA CAG | 127 | |
| optimal_loci_2 85621 | OGL1 7 | pDAB117413SIG12078_11v1: CCCGGACGACGCCGAG | 128 | 218 |
| | | SIG12078_12v1: GACATGGCACGCGCAT CGAG | 129 | |
| optimal_loci_1 57315 | OGL 13 | pDAB117429SIG157315_1v1: GCATGTGTGGTTTTG | 130 | 219 |
| | | SIG157315_2v1: GGTCAAGGTAGTGAC | 131 | |

The *Zea mays* representative genomic loci zinc finger designs were incorporated into zinc finger expression vectors encoding a protein having at least one finger with a CCHC structure. See, U.S. Patent Publication No. 2008/

0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid linker and an opaque-2 nuclear localization signal derived from *Zea mays* to form zinc-finger nucleases (ZFNs). See, U.S. Pat. No. 7,888,121. Zinc fingers for the various functional domains were selected for in vivo use. Of the numerous ZFNs that were designed, produced and tested to bind to the putative genomic target site, the ZFNs described in Table 2 above were identified as having in vivo activity and were characterized as being capable of efficiently binding and cleaving the unique *Zea mays* genomic polynucleotide target sites in planta.

ZFN Construct Assembly

Plasmid vectors containing ZFN gene expression constructs, which were identified as previously described, were designed and completed using skills and techniques commonly known in the art (see, for example, Ausubel or Maniatis). Each ZFN-encoding sequence was fused to a sequence encoding an opaque-2 nuclear localization signal (Maddaloni et al., (1989) Nuc. Acids Res. 17:7532), that was positioned upstream of the zinc finger nuclease. The non-canonical zinc finger-encoding sequences were fused to the nuclease domain of the type IIS restriction enzyme FokI (amino acids 384-579 of the sequence of Wah et al. (1998) Proc. Natl. Acad. Sci. USA 95:10564-10569). Expression of the fusion proteins was driven by the strong constitutive promoter from the *Zea mays* Ubiquitin gene, (which includes the 5' untranslated region (UTR) (Toki et al., (1992) Plant Physiology 100; 1503-07). The expression cassette also included the 3' UTR (comprising the transcriptional terminator and polyadenylation site) from the *Zea mays* peroxidase 5 gene (Per5) gene (US Patent Publication No. 2004/0158887). The self-hydrolyzing 2A encoding the nucleotide sequence from Thosea asigna virus (Szymczak et al., (2004) Nat Biotechnol. 22:760-760) was added between the two Zinc Finger Nuclease fusion proteins that were cloned into the construct.

The plasmid vectors were assembled using the IN-FUSION™ Advantage Technology (Clontech, Mountain View, Calif.). Restriction endonucleases were obtained from New England BioLabs (Ipswich, Mass.) and T4 DNA Ligase (Invitrogen, Carlsbad, Calif.) was used for DNA ligation. Plasmid preparations were performed using NUCLEO-SPIN® Plasmid Kit (Macherey-Nagel Inc., Bethlehem, Pa.) or the Plasmid Midi Kit (Qiagen) following the instructions of the suppliers. DNA fragments were isolated using QIA-QUICK GEL EXTRACTION KIT™ (Qiagen) after agarose tris-acetate gel electrophoresis. Colonies of all ligation reactions were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Plasmids were constructed and confirmed via restriction enzyme digestion and via DNA sequencing.

Universal Donor Construct Assembly

To support rapid testing of a large number of target loci, a novel, flexible universal donor system sequence was designed and constructed. The universal donor polynucleotide sequence was compatible with high throughput vector construction methodologies and analysis. The universal donor system was composed of at least three modular domains: a non-variable ZFN binding domain, an analytical and user defined features domain, and a simple plasmid backbone for vector scale up. The non-variable universal donor polynucleotide sequence was common to all donors and permits design of a finite set of assays that can be used across all of the *Zea mays* target sites thus providing uniformity in targeting assessment and reducing analytical cycle times. The modular nature of these domains allowed for high throughput donor assembly. Additionally, the universal donor polynucleotide sequence has other unique features aimed at simplifying downstream analysis and enhancing the interpretation of results. It contained an asymmetric restriction site sequence that allowed the digestion of PCR products into diagnostically predicted sizes. Sequences comprising secondary structures that were expected to be problematic in PCR amplification were removed. The universal donor polynucleotide sequence was small in size (less than 3.0 Kb). Finally, the universal donor polynucleotide sequence was built upon the high copy pUC19 backbone that allows a large amount of test DNA to be bulked in a timely fashion.

Figure 2:
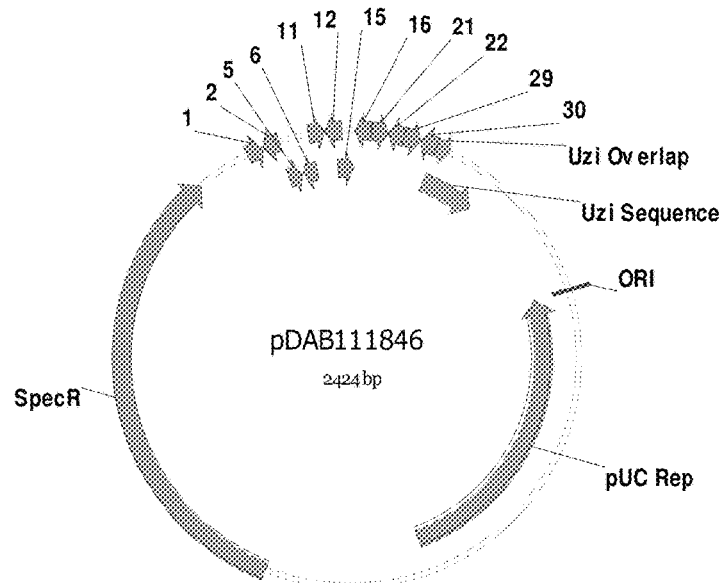
FIG. 2 illustrates a plasmid map of pDAB111846. The numbered elements (i.e., 1, 2, 5, 6, 11, 12, 15, 16, 21, 22, 29 and 30) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette.
Figure 3:
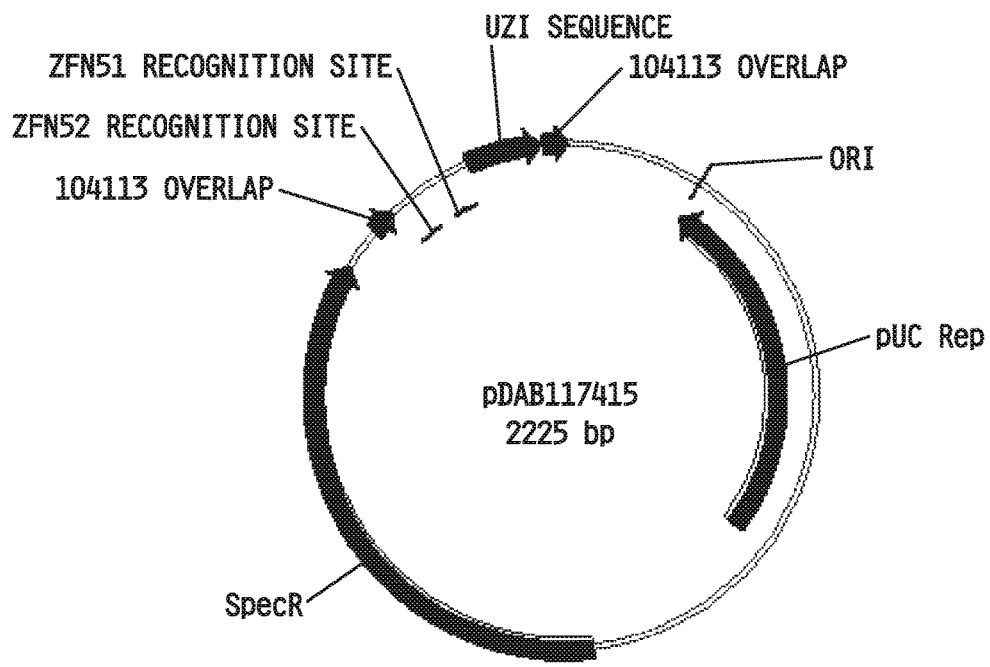
FIG. 3 illustrates a plasmid map of pDAB117415. The numbered elements (i.e., ZFN51 and ZFN52) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 4:
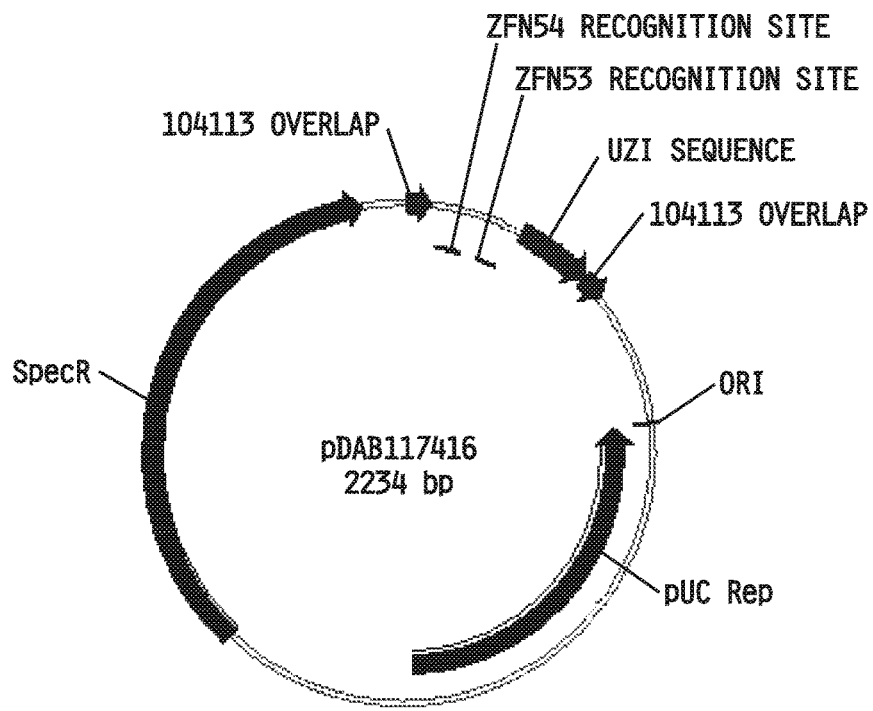
FIG. 4 illustrates a plasmid map of pDAB117416. The numbered elements (i.e., ZFN54 and ZFN53) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 5:
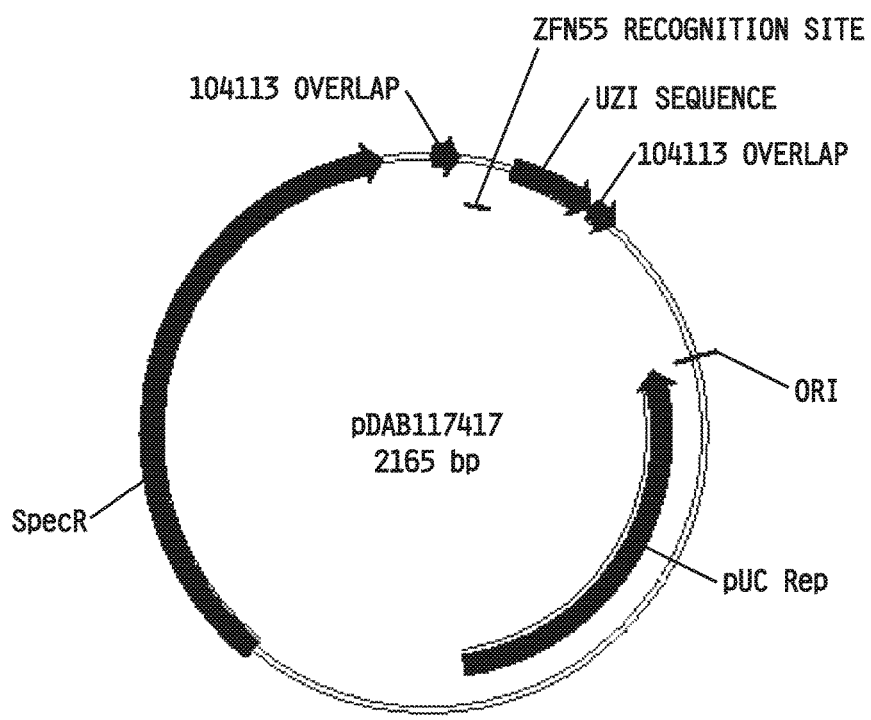
FIG. 5 illustrates a plasmid map of pDAB117417. The numbered element (i.e., ZFN55) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 6:
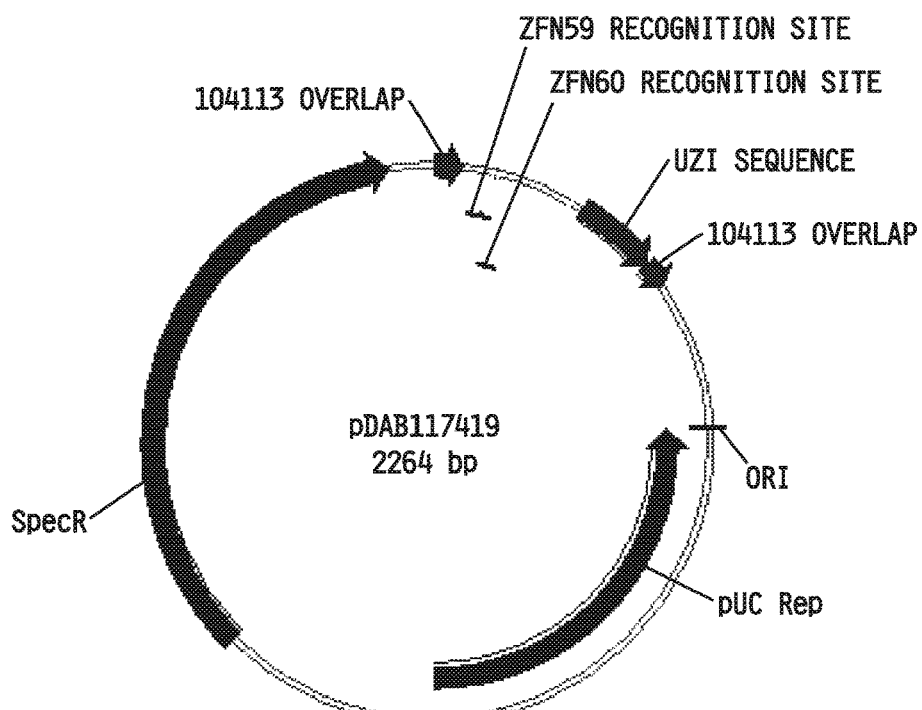
FIG. 6 illustrates a plasmid map of pDAB117419. The numbered elements (i.e., ZFN59 and ZFN60) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 7:
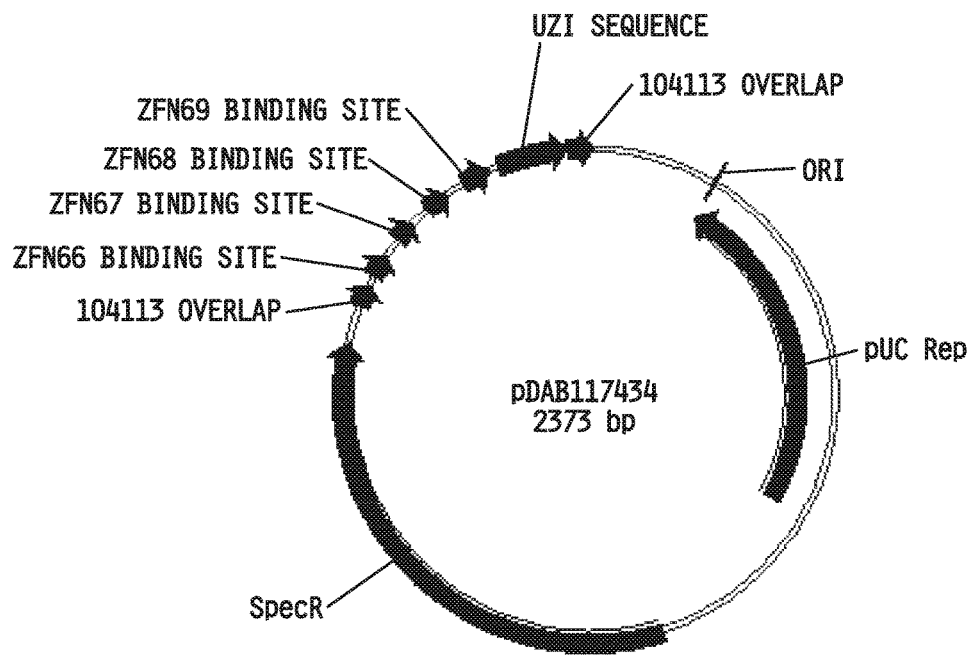
FIG. 7 illustrates a plasmid map of pDAB117434. The numbered elements (i.e., ZFN66, ZFN67, ZFN68 and ZFN69) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 8:
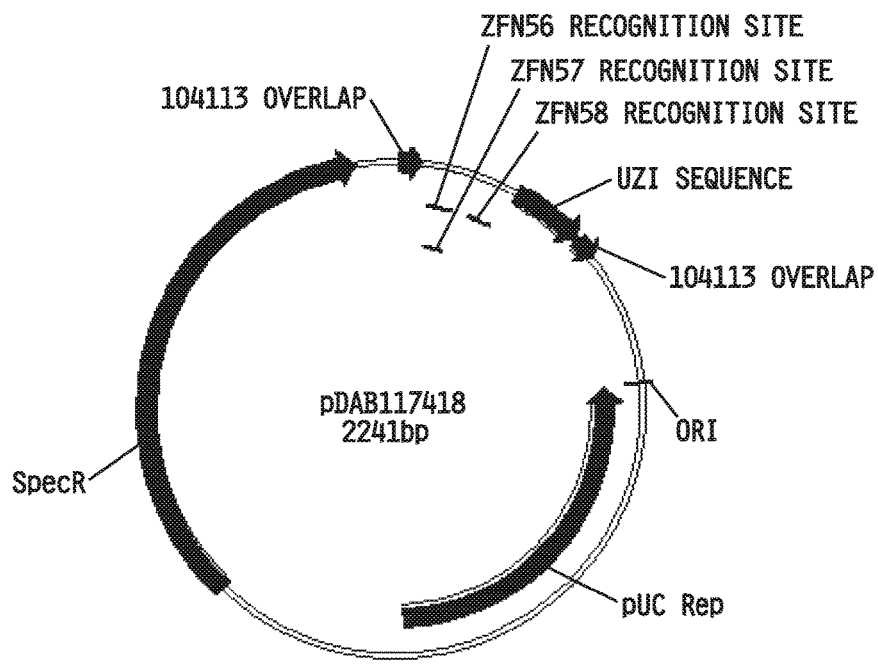
FIG. 8 illustrates a plasmid map of pDAB117418. The numbered elements (i.e., ZFN56, ZFN57, and ZFN58) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 9:
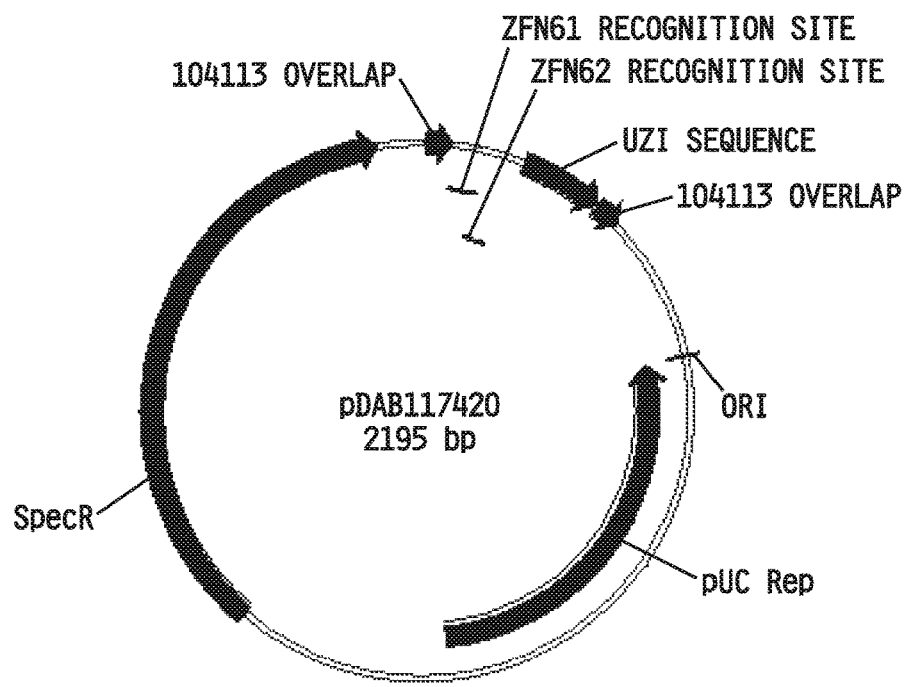
FIG. 9 illustrates a plasmid map of pDAB117420. The numbered elements (i.e., ZFN61 and ZFN62) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).
Figure 10:
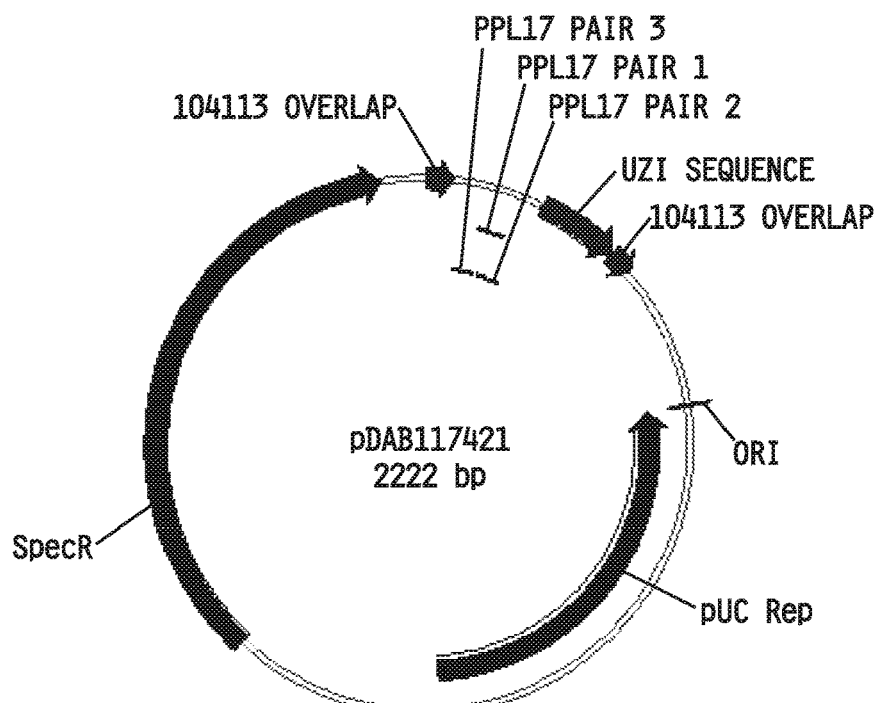
FIG. 10 illustrates a plasmid map of pDAB117421. The numbered elements (i.e., PPL17 Pair 3, PPL17 Pair 1, and PPL17 Pair2) correspond with zinc finger nuclease binding sequences of about 20 to 35 base pairs in length that are recognized and cleaved by corresponding zinc finger nuclease proteins. These zinc finger binding sequences and the annotated "UZI Sequence" (which is a 100-150 bp template region containing restriction sites and DNA sequences for primer design or coding sequences) comprise the universal donor cassette. Further included in this plasmid design is the "104113 Overlap" which are sequences that share homology to the plasmid vector for high throughput assembly of the universal donor cassettes within a plasmid vector (i.e., via Gibson assembly).

As an embodiment, an example plasmid comprising a universal polynucleotide donor cassette sequence is provided as SEQ ID NO:132 and FIG. 1. In an additional embodiment, a polynucleotide donor cassette sequence is provided as: pDAB111846, SEQ ID NO:133, FIG. 2; pDAB117415, SEQ ID NO:134, FIG. 3; pDAB117416, SEQ ID NO:135, FIG. 4; pDAB117417, SEQ ID NO:136, FIG. 5; pDAB117419, SEQ ID NO:137, FIG. 6; pDAB117434 SEQ ID NO:138, FIG. 7; pDAB117418, SEQ ID NO:139, FIG. 8; pDAB117420, SEQ ID NO:140, FIG. 9; and, pDAB117421, SEQ ID NO:141, FIG. 10. In another embodiment, additional sequences comprising the universal donor polynucleotide sequence with functionally expressing coding sequence or nonfunctional (promoterless) expressing coding sequences can be constructed. The various domains (a non-variable ZFN binding domain, an analytical and user defined features domain, and a simple plasmid backbone) that make up the universal donor system are annotated for the constructs, as described above, in Table 3.

TABLE 3

Annotation of universal donor system vectors to identify the non-variable ZFN binding domains, analytical and user defined features domain, and plasmid backbone.

| Vector Name | ZFN binding domain | Analytical domain | Homology Arm Regions | Plasmid backbone |
|---|---|---|---|---|
| pDAB111845 | 2244-144 Bp | 145-254 Bp | — | 255-2243 Bp |
| pDAB111846 | 2243-143 Bp | 144-253 Bp | — | 254-2242 Bp |
| pDAB117415 | 1961-2069 Bp | 2081-2190 Bp | 1920-1954 Bp, 2191-2225 Bp | 2226-1919 Bp |
| pDAB117416 | 51-155 Bp | 171-280 Bp | 1-35 Bp, 281-315 Bp | 316-2234 Bp |
| pDAB117417 | 51-86 Bp | 102-211 Bp | 1-35 Bp, 212-246 Bp | 247-2165 Bp |
| pDAB117419 | 51-119 Bp | 201-310 Bp | 1-35 Bp, 311-345 Bp | 345-2264 Bp |

TABLE 3-continued

Annotation of universal donor system vectors to identify the non-variable ZFN binding domains, analytical and user defined features domain, and plasmid backbone.

| Vector Name | ZFN binding domain | Analytical domain | Homology Arm Regions | Plasmid backbone |
|---|---|---|---|---|
| pDAB117434 | 1970-2213 Bp | 2229-2338 Bp | 1920-1954 Bp, 2339-2373 Bp | 1-1919 Bp |
| pDAB117418 | 51-162 Bp | 178-287 Bp | 1-35 Bp, 288-322 Bp | 323-2241 Bp |
| pDAB117420 | 37-116 Bp | 132-241 Bp | 1-35 Bp, 242-276 Bp | 277-2195 Bp |
| pDAB117421 | 51-143 Bp | 159-268 Bp | 1-35 Bp, 269-303 Bp | 304-2222 Bp |

Figure 11:
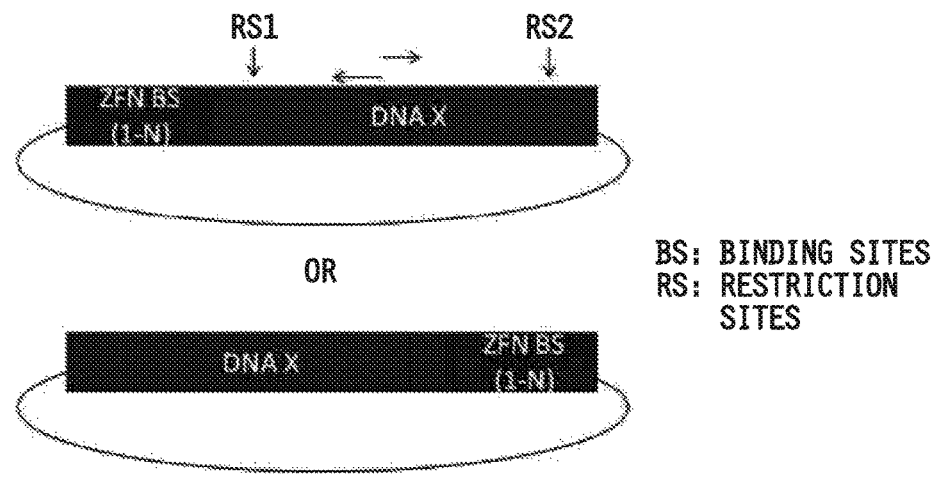
FIG. 11 Representation of the universal donor polynucleotide sequence for integration via non-homologous end joining (NHEJ). Two proposed vectors are provide wherein a DNA of interest (DNA X) comprises one or more (i.e., "1-N") zinc finger binding sites (ZFN BS) at either end of the DNA of interest. Vertical arrows show unique restriction sites and horizontal arrows represent potential PCR primer sites.

In another embodiment, the universal donor polynucleotide sequence is a small 2-3 Kb modular donor system delivered as a plasmid. This is a minimal donor, comprising any number of ZFN binding sites, a short 100-150 bp template region referred to as "DNA X" or "UZI Sequence" or "analytical domain" (SEQ ID NO:142 and SEQ ID NO:143) that carries restriction sites and DNA sequences for primer design (primers are designed at a Tm of 10° C. greater than any calculated secondary structures) or coding sequences, and a simple plasmid backbone (FIG. 11). In an embodiment, the analytical domain is designed: to contain a guanine and cytosine base pair percentage of 40 to 60%; to not contain repetitive sequences of more than 9 Bp (e.g., 5'-gtatttcatgtatttcat-3'); to not contain a series of identical base pairs greater than 9 Bp; and, is free of secondary structure, where the secondary structure is less than −18 kcal/mol of free energy as calculated by Markham, N. R. & Zuker, M. (2008) UNAFold: software for nucleic acid folding and hybridization. In Keith, J. M., editor, Bioinformatics, *Volume II. Structure, Function and Applications*, number 453 in *Methods in Molecular Biology*, chapter 1, pages 3-31. Humana Press, Totowa, N.J. ISBN 978-1-60327-428-9. See, Table 4. The entire plasmid is inserted through NHEJ following DNA double strand break at the appropriate ZFN binding site; the ZFN binding sites can be incorporated tandemly. This embodiment of a universal donor polynucleotide sequence is most suitable for rapid screening of target sites and ZFNs, and sequences that are difficult to amplify are minimized in the donor.

TABLE 4

Analysis of the analytical domain composition for ΔG free energy, number of 9 Bp runs of identical base pairs, number of repetitive sequences of more than 9 Bp, and guanine/cytosine percentage.

| SEQ ID NO: | ΔG free energy | Number of 9 Bp runs of identical base pairs | Number of repetitive Sequences of more than 9 Bp | GC % |
|---|---|---|---|---|
| SEQ ID NO: 142 | −12.42 kcal/mol | None | None | 50.9% |
| SEQ ID NO: 143 | −12.78 kcal/mol | None | None | 47.5% |

Figure 12:
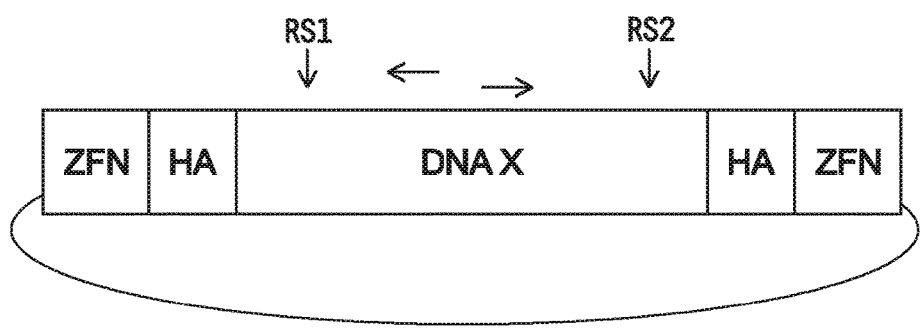
FIG. 12 Representation of the universal donor polynucleotide sequence for integration via homologous-directed repair (HDR). A DNA of interest (DNA X) comprising two regions of homologous sequences (HA) flanking the DNA of interest with zinc finger nuclease binding sites (ZFN) bracketing the DNAX and HA sequences. Vertical arrows show unique restriction sites and horizontal arrows represent potential PCR primer sites.

In a further embodiment the universal donor polynucleotide sequences is made up of at least four modules and carries partial ZFN binding sites, homology arms, DNA X with either the approximately 100 bp analytical piece or coding sequences. This embodiment of the universal donor polynucleotide sequence is suitable for interrogating NHEJ mediated gene insertion at a variety of polynucleotide target sites, with several ZFNs. (FIG. 12).

The universal donor polynucleotide sequence can be used with all targeting molecules with defined DNA binding domains, with two modes of targeted donor insertion (NHEJ/HDR). As such, when the universal donor polynucleotide sequence is co-delivered with the appropriate ZFN expression construct, the donor vector and the maize genome are both cleaved in one specific location dictated by the binding of the particular ZFN. Once linearized, the donor can be incorporated into the genome by NHEJ or HDR. The different analytical considerations in the vector design can then be exploited to determine the Zinc Finger which maximizes the efficient delivery of targeted integration. (FIG. 13).

Example 2

*Zea mays* Transformation Procedures

Before delivery to *Zea mays* c.v. Hi-II protoplasts, plasmid DNA for each ZFN construct was prepared from cultures of *E. coli* using the PURE YIELD PLASMID MAXIPREP SYSTEM® (Promega Corporation, Madison, Wis.) or PLASMID MAXI KIT® (Qiagen, Valencia, Calif.) following the instructions of the suppliers.

Protoplast Isolation

*Zea mays* c.v. Hi-II suspension cells were maintained at a 3.5 day maintenance schedule, 4 mL packed cell volume (PCV) of cells were collected and transferred to 50 mL sterile conical tubes (Fisher Scientific) containing 20 mL of enzyme solution (0.6% PECTOLYASE™, 6% CELLULASE™ ("Onozuka" R10; Yakult Pharmaceuticals, Japan), 4 mM MES (pH 5.7), 0.6 M mannitol, 15 mM $MgCl_2$). The cultures were capped and wrapped in PARAFILM™ and placed on a platform rocker (Thermo Scientific, Vari Mix platform Rocker) at speed setting 10 for incubation for 16-18 hours at room temperature until protoplasts were released. Following incubation, the cells were microscopically evaluated for quality of digestion. The digested cells were filtered through 100 μm cell strainer, rinsed with 10 mL W5 media [2 mM MES (pH5.7), 205 mM NaCl, 167 mM $CaCl_2$, 6.7 mM KCl], followed by filtering through 70 μm and 40 μm cell strainers. The 100 μm and 40 μm strainers were rinsed with 10 mL W5 media. The filtered protoplasts along with rinsed media were collected in 50 ml centrifuge tube and final volume was approximately 40 mL. Then, 8 mL of "Heavy Gradient solution" [500 mM sucrose, 1 mM $CaCl_2$, 5 mM MES (pH6.0)] was then slowly added to the bottom of the protoplast/enzyme solution, centrifuged in a centrifuge with a swing arm bucket rotor for 15 minutes at 300-350×g. Following centrifugation, about 7-8 mL of the protoplast band was removed, washed with 25 mL of W5, and centrifuged for 15 minutes at 180-200×g. The protoplasts were then resuspended in 10 mLs of MMG solution [4 mM MES (pH 5.7), 0.6 M mannitol, 15 mM $MgCl_2$]. Protoplasts were counted using a haemocytometer or flow cytometer and diluted to 1.67 million per ml using MMG.

Transformation of *Zea mays* c.v. Hi-II Suspension Culture Derived Protoplasts Using PEG Approximately 0.5 million protoplasts (300 µL in MMG solution) were transferred to 2 mL tubes, mixed with 40 µL of DNA and incubated at room temperature for 5-10 minutes. Next, 300 µL of freshly prepared PEG solution (36% PEG 4000, 0.3 M mannitol, 0.4M $CaCl_2$) was added, and the mixture was incubated at room temperature 15-20 minutes with periodic mixing by inversion. After incubation, 1 mL of W5 wash was added slowly, the cells mixed gently and protoplasts were pelleted by centrifugation at 180-200×g for 15 minutes. The pellet was resuspended in 1 ml of WI media [4 mM MES (pH 5.7), 0.6 M mannitol, 20 mM KCl] the tube wrapped with aluminum foil and incubated in room temperature overnight for about 16 hours.

Transformation of ZFN and Donor

For each of the selected genomic loci, the Zea mays protoplasts were transfected with a yfp gene expressing control, ZFN alone, donor alone and a mixture of ZFN and donor at 1:10 ratio (by weight). The total amount of DNA for transfection of 0.5 million protoplasts was 80 µg. All treatments were conducted in replicates of either three or six. The yfp gene expressing control used was pDAB8393 (FIG. 14) containing the Zea mays Ubiquitin 1 promoter—yellow fluorescent protein coding sequence—Zea mays PerS 3'UTR and the Rice Actin1 promoter—pat coding sequence—Zea mays lipase 3'UTR gene expression cassettes. In a typical targeting experiment, 4 µg of ZFN alone or with 36 µg of donor were co-transfected, 40 µg of yfp reporter gene construct was added to each treatment. Inclusion of consistent amounts of yfp gene expressing plasmid as filler allows assessment of transfection quality across multiple loci and replicate treatments. In addition, the use of consistent amounts of yfp gene expressing plasmids allows for the quick trouble shooting of any technical issues in the rapid targeting analysis of the donor insertion.

Example 3

Cleavage of Genomic Loci in Zea mays Via Zinc Finger Nuclease

ZFN transfected Zea mays c.v. Hi-II protoplasts were harvested 24 hours post-transfection, by centrifugation at 1600 rpm in 2 mL EPPENDORF™ tubes and the supernatant was removed. Genomic DNA was extracted from protoplast pellets using the QIAGEN PLANT DNA EXTRACTION KIT™ (Qiagen, Valencia, Calif.). The isolated DNA was resuspended in 50 µL of water and concentration was determined by NANODROP® (Invitrogen, Grand Island, N.Y.). The integrity of the DNA was estimated by running samples on 0.8% agarose gel electrophoresis. All samples were normalized (20-25 ng/µL) for PCR amplification to generate amplicons for sequencing (Illumina, Inc., San Diego, Calif.). Bar-coded PCR primers for amplifying regions encompassing each test ZFN recognition sequence from treated and control samples were designed and purchased from IDT (Coralville, Iowa, HPLC purified). Optimum amplification conditions were identified by gradient PCR using 0.2 µM appropriate bar-coded primers, ACCUPRIME PFX SUPERMIX™ (Invitrogen, Carlsbad, Calif.) and 100 ng of template genomic DNA in a 23.5 µL reaction. Cycling parameters were initial denaturation at 95° C. (5 min) followed by 35 cycles of denaturation (95° C., 15 sec), annealing (55-72° C., 30 sec), extension (68° C., 1 min) and a final extension (68° C., 7 min). Amplification products were analyzed on 3.5% TAE agarose gels and appropriate annealing temperature for each primer combination was determined and used to amplify amplicons from control and ZFN treated samples as described above. All amplicons were purified on 3.5% agarose gels, eluted in water and concentrations were determined by NANODROP™. For Next Generation Sequencing, approximately 100 ng of PCR amplicon from the ZFN treated and corresponding maize protoplast controls were pooled together and sequenced using Illumina Next Generation Sequencing (NGS).

Figures 15A, 15B:
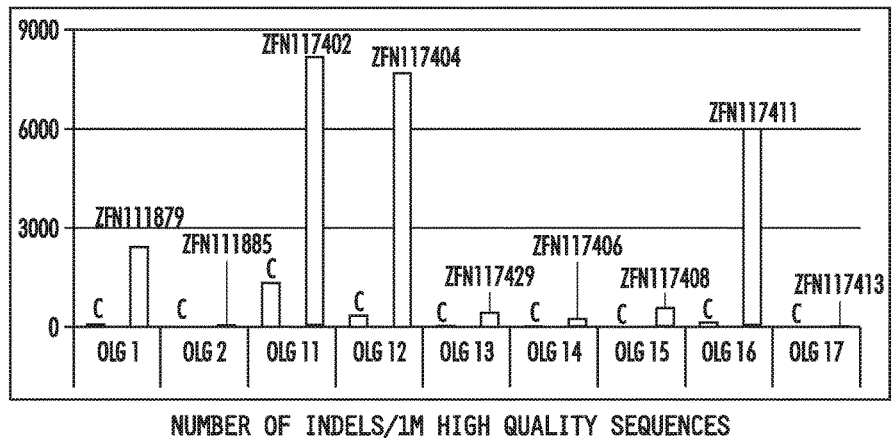
FIGS. 15A and 15B illustrate the ZFN cleavage activity at *Zea mays* selected genomic loci targets. Cleavage activity is represented as number of sequences with indels (insertions and deletions) at the ZFN cleavage site per 1 million high quality reads. Data is presented as numerical data (FIG. 15B) and in bar graph form (FIG. 15A).

The cleavage activity of appropriate ZFNs at each Zea mays selected genomic loci were assayed. Short amplicons encompassing the ZFN cleavage sites were amplified from the genomic DNA and subjected to Illumina NGS from ZFN treated and control protoplasts. The ZFN induced cleavage or DNA double strand break was resolved by the cellular NHEJ repair pathway by insertion or deletion of nucleotides (Indels) at the cleavage site and presence of Indels at the cleavage site is thus a measure of ZFN activity and was determined by NGS. Cleavage activity of the target specific ZFNs was estimated as the number of sequences with Indels per one million high quality sequences using NGS analysis software (Patent publication 2012-0173,153, data Analysis of DNA sequences) (FIGS. 15A and 15B). Activities in the range of 5-100 fold over controls were observed for Zea mays selected genomic loci targets and were further confirmed by sequence alignments that showed a diverse footprint of Indels at each ZFN cleavage site. This data suggests that the Zea mays selected genomic loci are amenable to cleavage by ZFNs. Differential activity at each target is reflective of its chromatin state and amenability to cleavage as well as the efficiency of expression of each ZFN.

Example 4

Rapid Targeting Analysis of the Integration of a Polynucleotide Donor

Sequence within the Genomic Loci in Zea mays via Zinc Finger Nuclease

Figure 16:
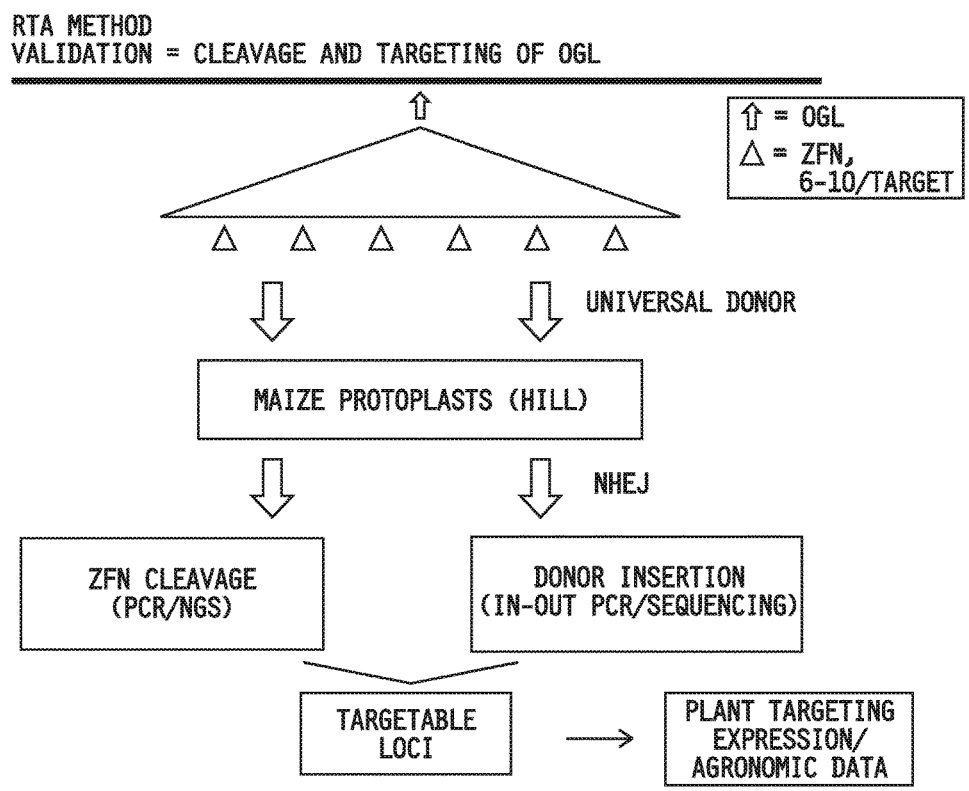
FIG. 16 illustrates the validation of *Zea mays* selected genomic loci targets using NHEJ based Rapid Targeting Analysis (RTA) method.
Figure 17:
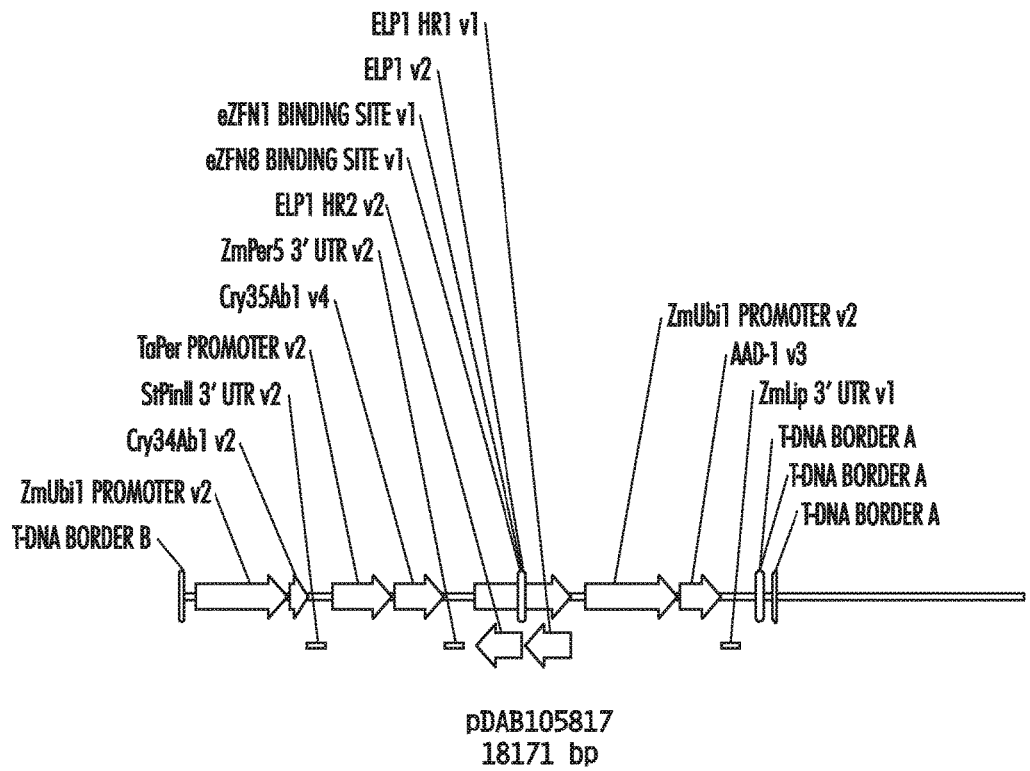
FIG. 17 illustrates plasmid constructs transformed into *Zea mays* via random integration that comprise the events used for flanking sequence analysis and transgene expression studies.
Figure 17:
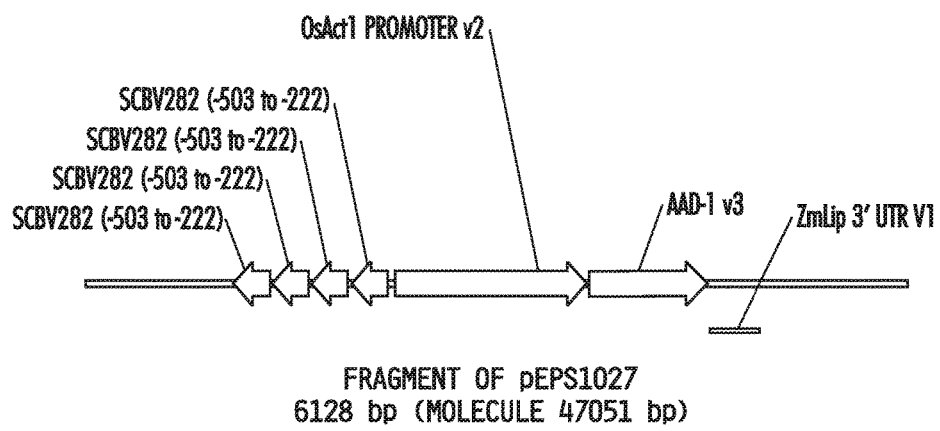

Validation of the targeting of the universal donor polynucleotide sequence within the Zea mays selected genomic loci targets via non-homologous end joining (NHEJ) mediated donor insertion, was performed using a semi-throughput protoplast based Rapid Targeting Analysis method. For each Zea mays selected genomic loci target, three to six ZFN designs were tested and targeting was assessed by measuring ZFN mediated cleavage by Next Generation Sequencing methods (FIGS. 15A and 15B) and donor insertion by junctional In-Out PCR (FIG. 16). Zea mays selected genomic loci that were positive in both assays were identified as a targetable locus.

ZFN Donor Insertion Rapid Targeting Analysis

To determine if a Zea mays selected genomic loci target can be targeted for donor insertion, a ZFN construct and universal donor polynucleotide construct were co-delivered to maize protoplasts which were incubated for 24 hours before the genomic DNA was extracted for analysis. If the expressed ZFN was able to cut the target binding site both at the Zea mays selected genomic loci target and in the donor, the linearized donor would then be inserted into the cleaved target site in the maize genome via the non-homologous end joining (NHEJ) pathway. Confirmation of targeted integration at the Zea mays selected genomic loci target was completed based on an "In-Out" PCR strategy, where an "Out" primer recognizes sequence at the native genomic loci and an "In" primer binds to sequence within the donor DNA. The primers are designed in a way that only when the donor DNA is inserted at the Zea mays selected genomic loci target, would the PCR assay produce an amplification product of an expected size. The In-Out PCR assay is performed at both the 5'- and 3'-ends of the insertion junction. The primers used for the analysis of integrated polynucleotide donor sequences are provided in Table 5.

ZFN Donor Insertion at Target Loci Using Nested "In-Out" PCR

All PCR amplifications were conducted using a TAKARA EX TAQ HS™ kit (Clonetech, Mountain View, Calif.). The first In-Out PCR was carried out in 20 µL final reaction volume that contains 1× TAKARA EX TAQ HS™ buffer, 0.2 mM dNTPs, 0.2 µM "Out" primer (Table 5), 0.05 µM "In" primer (designed from the universal donor cassette described above), 0.75 unit of TAKARA EX TAQ HS™ polymerase, and 10 ng extracted maize protoplast DNA. The reaction was then carried out using a PCR program that consisted of 94° C. for 2 min, 20 cycles of 98° C. for 12 sec and 68° C. for 2 min, followed by 72° C. for 10 min and held at 4° C. Final PCR products were run on an agarose gel along with 1 KB PLUS DNA LADDER™ (Life Technologies, Grand Island, N.Y.) for visualization.

The nested In-Out PCR was conducted in a 20 µL final reaction volume that contained 1× TAKARA EX TAQ HS™ buffer, 0.2 mM dNTPs, 0.2 µM "Out" primer (Table 5), 0.1 µM "In" primer (designed from the universal donor cassette described above, Table 6), 0.75 unit of TAKARA EX TAQ HS™ polymerase, and 1 µL of the first PCR product. The reaction was then carried out using a PCR program that consisted of 94° C. for 2 min, 31 cycles of 98° C. for 12 sec, 66° C. for 30 sec and 68° C. for 45 sec, followed by 72° C. for 10 min and held at 4° C. Final PCR products were run on an agarose gel along with 1 KB PLUS DNA LADDER™ (Life Technologies, Grand Island, N.Y.) for visualization.

TABLE 5

List of all "Out" primers for nested In-Out PCR analysis of optimal genomic loci.

| OGL1 | First PCR | 5'-APL02-end 5PriF1 | SEQ ID NO: 144 CGCCACAAATCTGAACCAGCA |
|---|---|---|---|
| | | Spec-PriR1 | SEQ ID NO: 145 CCACGATCGACATTGATCTGGCTA |
| | | 3'-APL02-end 3PriR1 | SEQ ID NO: 146 GCGACATATCAGGCCAACAGG |
| | | Uzi-PriF1 | SEQ ID NO: 147 GGGATATGTGTCCTACCGTATCAGG |
| | Nest PCR | 5'-APL02-end 5nstPriF1 | SEQ ID NO: 148 CCAGCATACAGTTAGGGCCCA |
| | | Spec-nstPriR1 | SEQ ID NO: 149 GTTGCCTTGGTAGGTCCAGC |
| | | 3'-APL02-end 3nstPriR1 | SEQ ID NO: 150 CGAAAACTCAGCATGCGGGAA |
| | | Uzi-nstPriF1 | SEQ ID NO: 151 GAGCCATCAGTCCAACACTGC |

TABLE 5-continued

List of all "Out" primers for nested In-Out PCR analysis of optimal genomic loci.

| OGL2 | First PCR | 5'-APL01-end 5PriF1 | SEQ ID NO: 152 ACAGGCGTACAGCAACACCA |
|---|---|---|---|
| | | 3'-APL01-end 3PriR1 | SEQ ID NO: 153 GACCCTATGGTGTTGGATCCCA |
| | Nest PCR | 5'-APL01-end 5nstPriF1 | SEQ ID NO: 154 CGGGAGCTAGGCAACAAATCG |
| | | 3'-APL01-end 3nstPriR1 | SEQ ID NO: 155 TCTGACTAAACGGGTGGATGCTG |
| OGL8 | First PCR | 5'-OGL08-end 5nstPriF2 | SEQ ID NO: 156 CGGATCAGTTGATTCGCTCACTTTCA |
| | | 3'-OGL08-end 3PriR | SEQ ID NO: 157 GCCGAAAAGCAGCAACTGGAA |
| | Nest PCR | 5'-OGL08-end 5nstPriF | SEQ ID NO: 158 GATTGCTACGCAGACCGCCTA |
| | | 3'-OGL08-end 3nstPriR | SEQ ID NO: 159 CACTATTCCTCCGGCATGCAG |
| OGL11 | First PCR | 5'-OGL11-end 5PriF | SEQ ID NO: 160 TGACCTATTGATCGGTCGGCTC |
| | | 3'-OGL11-end 3PriR2 | SEQ ID NO: 161 TGCCTTGAATCTCAGGGATGCA |
| | Nest PCR | 5'-OGL11-end 5nstPriF | SEQ ID NO: 162 GCCGAAGCTAACTAGCGGACA |
| | | 3'-OGL11-end 3nstPriR2 | SEQ ID NO: 163 CATGGAGTAGCAGCTGTGCTG |
| OGL12 | First PCR | 5'-OGL12-end 5PriF | SEQ ID NO: 164 GAAAAGCAGTCACCGGCTCTG |
| | | 3'-OGL12-end 3PriR | SEQ ID NO: 165 CCATGGACATGAATTCGGCACG |
| | Nest PCR | 5'-OGL12-end 5nstPriF | SEQ ID NO: 166 CTTTTGCACCACGGAGCAGAC |
| | | 3'-OGL12-end 3nstPriR | SEQ ID NO: 167 GCTAGCAAAACTTTGAAGCTCGCTC |
| OGL13 | First PCR | 5'-OGL13-end 5PriF | SEQ ID NO: 168 GAGGTCCCTTACGGGTCATCG |
| | | 3'-OGL13-end 3PriR | SEQ ID NO: 169 ACCAGGTCTATCTTGCGCAGAC |
| | Nest PCR | 5'-OGL13-end 5nstPriF | SEQ ID NO: 170 AATAGCGTGGTCGGGTCCTAG |
| | | 3'-OGL13-end 3nstPriR | SEQ ID NO: 171 ACGAACGATCCAAGGTGCAGT |
| OGL14 | First PCR | 5'-OGL14-end 5PriF | SEQ ID NO: 172 TAGAGACGAGGACTCTGGGCT |
| | | 3'-OGL14-end 3PriR | SEQ ID NO: 173 AAGTCCAACATGGGCACAACC |
| | Nest PCR | 5'-OGL14-end 5nstPriF | SEQ ID NO: 174 CCTCGTTAAGGGTGCAGGTTG |
| | | 3'-OGL14-end 3nstPriR | SEQ ID NO: 175 CCAAGTCAGCTTCTAAGCCATCAAAC |

TABLE 5-continued

List of all "Out" primers for nested In-Out PCR analysis of optimal genomic loci.

| | | | |
|---|---|---|---|
| OGL15First PCR | 5'-end | OGL15-5PriF | SEQ ID NO: 176 AACCCTAGACTTCTGCCTGGTG |
| | 3'-end | OGL15-3PriR | SEQ ID NO: 177 GCTCACTTACGAGCAGATCCCA |
| Nest PCR | 5'-end | OGL15-5nstPriF | SEQ ID NO: 178 GGTGCACGCATGTTCTCATGT |
| | 3'-end | OGL15-3nstPriR | SEQ ID NO: 179 TGTTTACCGCAGCCATGCTTG |
| OGL16First PCR | 5'-end | OGL16-5PriF | SEQ ID NO: 180 GTTGTATACGGCATCCATCCGCT |
| | 3'-end | OGL16-3PriR | SEQ ID NO: 181 GAATGAAACTGGTGGTCTGCTCC |
| Nest PCR | 5'-end | OGL16-5nstPriF | SEQ ID NO: 182 CCGACGAGGTACAAGTAGCAGG |
| | 3'-end | OGL16-3nstPriR | SEQ ID NO: 183 CCCGTAGTCCAGATTCTTGTGGT |
| OGL17First PCR | 5'-end | OGL17-5PriF | SEQ ID NO: 184 GTCGTTTGTTCGGAAGGGGAG |
| | 3'-end | OGL17-3PriR | SEQ ID NO: 185 CGTAGTTGTCCGGCATGTCCT |
| Nest PCR | 5'-end | OGL17-5nstPriF | SEQ ID NO: 186 TGTATCCCTTCGGTGAGCACG |
| | 3'-end | OGL17-3nstPriR | SEQ ID NO: 187 TGAATCGACTCGCTGACAGGTG |

TABLE 6

List of all "In" primers for nested In-Out PCR analysis of optimal genomic loci.

| | | | |
|---|---|---|---|
| All Reactions | First PCR 5'-end 3'-end | Spec-PriR1 Uzi-PriF1 | SEQ ID NO: 188 CCACGATCGACATTGATCTGGCTA SEQ ID NO: 189 GGGATATGTGTCCTACCGTATCAGG |
| | Nest PCR 5'-end 3'-end | Spec-nstPriR1 Uzi-nstPriF1 | SEQ ID NO: 190 GTTGCCTTGGTAGGTCCAGC SEQ ID NO: 191 GAGCCATCAGTCCAACACTGC |

TABLE 7

Primers for ZFN cleavage activity.

| | | |
|---|---|---|
| OGL 1 | Control/ZFN 111879 | SEQ ID NO: 192 TGGCACTAATCTCACCGGCT SEQ ID NO: 193 AGTCTTAGAAGTACGCTACCGT |
| OGL 2 | Control/ZFN 111885 | SEQ ID NO: 194 TACTTGGCTTCGGCGGCGA SEQ ID NO: 195 GGGTGACTTTTACGCGTCTCG |
| OGL 11 | Control/ZFN 117402 | SEQ ID NO: 196 GGTCACGACGCATGGCCTAA SEQ ID NO: 197 AGGATGCATGGATCACCGTC |
| OGL 12 | Control/ZFN 117404 | SEQ ID NO: 198 GCTCTGTTGTGCAGCCGTAC SEQ ID NO: 199 CGTTGCAGATACCACAGTGTAC |
| OGL 13 | Control/ZFN 117429 | SEQ ID NO: 200 GCTAGTAGCTGTTTACACGGCGTCT SEQ ID NO: 201 AGGTCGAGACAACCAAGTAGAG |
| OGL 14 | Control/ZFN 117406 | SEQ ID NO: 202 ACAGGACATCGAGCTTGCAT SEQ ID NO: 203 CAGAAGAAAGGCATCAACTCATG |
| OGL 15 | Control/ZFN 117408 | SEQ ID NO: 204 CTCTTTCACCTCTACTTTTACTTCAG SEQ ID NO: 205 ATTGAACCGTTGTCAAAGCCA |
| OGL 16 | Control/ZFN 117411 | SEQ ID NO: 206 CACAGCGTCAGGGCGGTAAC SEQ ID NO: 207 GGCACGCACCTGTCACTGAC |
| OGL 17 | Control/ZFN 117413 | SEQ ID NO: 208 GTACGCGCCCGGGAACTCCT SEQ ID NO: 209 CCTGCGGCCCACGTGCATCT |

Deployment of the In-Out PCR assay in a protoplast targeting system was particularly challenging as large amounts of the plasmid DNA was used for transfection, and the large amount of plasmid DNA remains in the protoplast targeting system and is subsequently extracted along with cellular genomic DNA. The residual plasmid DNA may dilute the relative concentration of the genomic DNA and reduce the overall sensitivity of detection and can also be a significant cause of non-specific, aberrant PCR reactions. The ZFN induced NHEJ-based donor insertion typically occurs in either a forward or a reverse orientation. In-Out PCR analysis of DNA for the forward orientation insertion often exhibited false positive bands, possibly due to shared regions of homology around the ZFN binding site in the target and donor that could result in priming and extension of unintegrated donor DNA during the amplification process. False positives were not seen in analyses that probed for reverse orientation insertion products and therefore all targeted donor integration analysis was carried out to interrogate reverse donor insertion in the Rapid Targeting Analysis. In order to further increase specificity and reduce background, a nested PCR strategy was also employed. The nested PCR strategy used a second PCR amplification reaction that amplified a shorter region within the first amplification product of the first PCR reaction. Use of asymmetric amounts of "In" and "Out" primers optimized the junctional PCR further for rapid targeting analysis at selected genomic loci.

The In-Out PCR analysis results were visualized on an agarose gel. For all *Zea mays* selected genomic loci, "ZFN+ donor treatments" produced a near expected sized band at the 5' and 3' ends. Control ZFN or donor alone treatments were negative in the PCR suggesting that the method was specifically scoring for donor integration at the target site. All treatments were conducted in replicates of three to six and presence of the anticipated PCR product in multiple replicates (≥2 at both ends) was used to confirm targeting. Donor insertion through NHEJ often produces lower intensity side products that are generated due to processing of linearized ends at the target and/or donor ZFN sites. In addition, it was observed that different ZFNs resulted in different levels of efficiency for targeted integration, with some of the ZFNs producing consistently high levels of donor integration, some ZFNs producing less consistent levels of donor integration, and other ZFNs resulting in no integration. Overall, for each of the *Zea mays* selected genomic loci targets that were tested, targeted integration was demonstrated within the *Zea mays* representative genomic loci targets by one or more ZFNs, which confirms that each of these loci were targetable. Furthermore, each of the *Zea mays* selected genomic loci targets is suitable for precision gene transformation. The validation of these *Zea mays* selected genomic loci targets was repeated multiple times with similar results every time, thus confirming the reproducibility of the validation process which includes plasmid design and construct, protoplast transformation, sample processing, and sample analysis.

CONCLUSION

The donor plasmid and one ZFN designed to specifically cleave a *Zea mays* selected genomic loci targets were transfected into *Zea mays* c.v. Hi-II protoplasts and cells were harvested 24 hours later. Analysis of the genomic DNA isolated from control, ZFN treated and ZFN with donor treated protoplasts by In-Out junctional PCR showed targeted insertion of the universal donor polynucleotide as a result of genomic DNA cleavage by the ZFNs (Table 8). These studies show that the universal donor polynucleotide system can be used to assess targeting at endogenous sites and for screening candidate ZFNs. Finally, the protoplast based Rapid Targeting Analysis and the novel universal donor polynucleotide sequence systems provide an improved system for screening genomic targets and ZFNs for precision genome engineering efforts in plants. The methods can be extended to assess site specific cleavage and donor insertion at genomic targets in any system of interest using any nuclease that introduces DNA double or single strand breaks.

TABLE 8

Results of the integration of a universal donor polynucleotide sequence within the *Zea mays* selected genomic loci targets.

| Name | ID | Location | Cluster Assignment | ZFN (pDAB#) | Donor (pDAB#) | Targetable Locus (Y/N) |
|---|---|---|---|---|---|---|
| OGL01 | optimal_loci_204637_G1 | chr5:200298202 . . . 200301414 | 16 | 111879 | 111845 | Y |
| OGL02 | optimal_loci_204726_G1 | chr5:200665730 . . . 200670667 | 03 | 111885 | 111846 | Y |
| OGL08 | optimal_loci_31710 | chr1:194939396 . . . 194943360 | 23 | 117400 | 117415 | Y |
| OGL11 | optimal_loci_64542 | chr2:72203716 . . . 72205045 | 14 | 117402 | 117416 | Y |
| OGL12 | optimal_loci_156393 | chr4:154313884 . . . 154315253 | 10 | 117404 | 117417 | Y |
| OGL15 | preffered_loci_198387 | chr5:164712378 . . . 164713567 | 25 | 117408 | 117419 | Y |
| OGL13 | optimal_loci_157315 | chr4:158710709 . . . 158711983 | 30 | 117429 | 117434 | Y |
| OGL14 | optimal_loci_197372 | chr5:158680601 . . . 158681681 | 26 | 117406 | 117418 | Y |
| OGL16 | optimal_loci_232228 | chr6:144719567 . . . 144723469 | 28 | 117411 | 117420 | Y |
| OGL17 | optimal_loci_285621 | chr8:118321357 . . . 118322528 | 06 | 117413 | 117421 | Y |

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

What is claimed is:

1. A polynucleotide donor cassette comprising a site specific nuclease binding domain, an analytical domain, and a plasmid domain, wherein said analytical domain comprises a polynucleotide sequence with at least 95% sequence identity to SEQ ID NO: 142.

2. A transgenic cell comprising the polynucleotide donor cassette of claim 1.

3. The transgenic cell of claim 2, wherein the cell is a transgenic plant cell.

4. A transgenic plant comprising the transgenic plant cell of claim 3.

5. The polynucleotide donor cassette of claim 1, wherein the polynucleotide donor cassette having the sequence of SEQ ID NO: 132.

6. The polynucleotide donor cassette of claim 1, wherein the site specific nuclease binding domain comprises two or more site specific nuclease binding sequences.

7. The polynucleotide donor cassette of claim 1, wherein the site specific nuclease binding domain is a zinc finger binding domain.

8. The polynucleotide donor cassette of claim 1, wherein the analytical domain is a polynucleotide sequence consisting of SEQ ID NO: 142.

9. The polynucleotide donor cassette of claim 1, wherein the [−] polynucleotide donor cassette having the sequence of SEQ ID NO: 133.

10. The polynucleotide donor cassette of claim 1, wherein the polynucleotide donor cassette further comprises one or more homology arm sequences.

11. The polynucleotide donor cassette of claim 1, wherein the analytical domain does not encode a peptide.

12. The polynucleotide donor cassette of claim 1, wherein the analytical domain further comprises coding sequences that encode a peptide.

13. The polynucleotide donor cassette of claim 12, wherein the analytical domain comprises a gene expression cassette comprising a transgene.

14. The polynucleotide donor cassette of claim 13, wherein the transgene comprises a reporter gene.

15. The polynucleotide donor cassette of claim 14, wherein the reporter gene is selected from the group consisting of a yfp gene, a gus gene, a rfp gene, a gfp gene, a kanamycin resistance gene, an aad-1 gene, an aad-12 gene, a pat gene, and a glyphosate tolerant gene.

* * * * *

```
                         SEQUENCE LISTING

<160> NUMBER OF SEQ ID NOS: 219

<210> SEQ ID NO 1
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 1

Gln Ser Gly Asp Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 2

Arg Lys Asp Gln Leu Val Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 3

Arg Ser Asp Asp Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 4

Thr Ser Ser Asn Arg Lys Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 5

Arg Ser Asp Thr Leu Ser Glu
1               5

<210> SEQ ID NO 6
<211> LENGTH: 7
<212> TYPE: PRT
<213> ORGANISM: Artificial Sequence
```

```
<220> FEATURE:
<223> OTHER INFORMATION: Zinc Finger Protein Recognition Helices

<400> SEQUENCE: 6

Ala Arg Ser Thr Arg Thr Asn
1               5

<210> SEQ ID NO 7
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 7

Arg Ser Asp Ser Leu Ser Val
1               5

<210> SEQ ID NO 8
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 8

Asp Arg Ser Asn Arg Lys Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 9

Gln Ser Ser His Leu Thr Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 10

Arg Ser Asp Ala Leu Ala Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 11

Arg Ser Asp Asp Leu Thr Arg
1               5

<210> SEQ ID NO 12
<211> LENGTH: 7
<212> TYPE: PRT
<213> ORGANISM: Artificial Sequence
<220> FEATURE:
```

<223> OTHER INFORMATION: Zinc Finger Protein Recognition Helices

<400> SEQUENCE: 12

Asp Pro Ser Ala Leu Arg Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 13

Arg Ser Asp Asn Leu Ser Gln
1               5

<210> SEQ ID NO 14
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 14

Ala Ser Asn Asp Arg Lys Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 15

Glu Arg Gly Thr Leu Ala Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 16

Arg Ser Asp His Leu Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 17

Glu Arg Gly Thr Leu Ala Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 18

Gln Ser Gly His Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 19

Arg Ser Ala Asn Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 20

Asp Arg Ser Asp Leu Ser Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 21

Arg Ser Asp Thr Leu Ser Gln
1               5

<210> SEQ ID NO 22
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 22

Arg Ser Ala Asp Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 23

Asp Arg Ser Asn Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Zinc Finger Protein Recognition Helices

```
<400> SEQUENCE: 24

Asn Ser Arg Asn Leu Arg Asn
1               5

<210> SEQ ID NO 25
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 25

Arg Ser Asp Ser Leu Ser Val
1               5

<210> SEQ ID NO 26
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 26

Asp Arg Ser His Leu Ala Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 27

Asp Arg Ser Asn Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 28

Arg Arg Ser Asp Leu Lys Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 29

Arg Ser Asp Thr Leu Ser Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 30
```

```
Gln Asn Ala Thr Arg Ile Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 31

Gln Ser Gly Ser Leu Thr Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 32

Gln Ser Gly Asp Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 33

Arg Ser Asp Val Leu Ser Glu
1               5

<210> SEQ ID NO 34
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 34

Thr Arg Asn Gly Leu Lys Tyr
1               5

<210> SEQ ID NO 35
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 35

Arg Ser Asp Asn Leu Ser Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 36
```

Asp Asn Ser Asn Arg Lys Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 37

Gln Asn Ala His Arg Lys Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 38

Gln Lys Ala Thr Arg Ile Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 39

Asp Arg Ser His Leu Thr Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 40

Arg Ser Asp Asp Arg Lys Lys
1               5

<210> SEQ ID NO 41
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 41

Ala Ser Lys Thr Arg Thr Asn
1               5

<210> SEQ ID NO 42
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 42

Gln Ser Gly Ser Leu Thr Arg

```
1               5

<210> SEQ ID NO 43
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 43

Leu Arg His His Leu Thr Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 44

Gln Ser Ala His Leu Lys Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 45

Gln Ser Gly Asp Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 46

Ala Ser His Asn Leu Arg Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 47

Asp Arg Ser Asn Leu Thr Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 48

Gln Ser Ser Asp Leu Ser Arg
1               5
```

<210> SEQ ID NO 49
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 49

Asp Ala Gly Asn Arg Asn Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 50

Asp Arg Ser Asp Leu Ser Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 51

Arg Ser Asp Asn Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 52

Asp Arg Ser His Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 53

Thr Ser Gly Asn Leu Thr Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 54

Gln Ser Ser Asp Leu Ser Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 55

Gln Ser Ser Asp Leu Ser Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 56

His Arg Ser Thr Arg Asn Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 57

Arg Ser Asp Asp Leu Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 58

Asp Arg Ser Asn Leu Lys Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 59

Asp Arg Ser His Leu Thr Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 60

Gln Arg Ser Thr Leu Lys Ser
1               5

```
<210> SEQ ID NO 61
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 61

Arg Ser Asp Ala Leu Ser Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 62

Arg Ser Asp Asp Leu Thr Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 63

Asp Arg Ser His Leu Thr Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 64

Thr Ser Ser Asn Arg Lys Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 65

Arg Ser Asp Thr Leu Ser Glu
1               5

<210> SEQ ID NO 66
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 66

Asp Arg Ser His Leu Ala Arg
1               5

<210> SEQ ID NO 67
```

```
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 67

Asp Arg Ser Ala Arg Thr Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 68

Gln Ser Gly His Leu Ser Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 69

Gln Ser Gly Asn Leu Ala Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 70

Arg Ser Asp Val Leu Ser Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 71

Arg Tyr Ala Tyr Leu Thr Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 72

Arg Arg Trp Thr Leu Val Gly
1               5

<210> SEQ ID NO 73
<211> LENGTH: 7
```

<212> TYPE: PRT
<213> ORGANISM: Artificial Sequence
<220> FEATURE:
<223> OTHER INFORMATION: Zinc Finger Protein Recognition Helices

<400> SEQUENCE: 73

Arg Ser Asp Asn Leu Ser Gln
1               5

<210> SEQ ID NO 74
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 74

Ala Ser Asn Asp Arg Lys Lys
1               5

<210> SEQ ID NO 75
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 75

Gln Ser Gly Asp Leu Thr Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 76

Leu Lys Asp Thr Leu Arg Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 77

Gln Ser Gly Asn Leu Ala Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 78

Gln Ser Gly Asp Leu Thr Arg
1               5

<210> SEQ ID NO 79
<211> LENGTH: 7
<212> TYPE: PRT

```
<213> ORGANISM: Artificial Sequence
<220> FEATURE:
<223> OTHER INFORMATION: Zinc Finger Protein Recognition Helices

<400> SEQUENCE: 79

Met Gln Asn Tyr Leu Ser Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 80

Arg Ser Asp His Leu Ser Glu
1               5

<210> SEQ ID NO 81
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 81

Gln Asn Ala Asn Arg Lys Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 82

Arg Ser Ala Asp Leu Thr Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 83

Arg Ser Asp Asn Leu Ser Glu
1               5

<210> SEQ ID NO 84
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 84

Gln Ser Ala Asn Arg Thr Lys
1               5

<210> SEQ ID NO 85
<211> LENGTH: 7
<212> TYPE: PRT
<213> ORGANISM: Artificial Sequence
```

```
<220> FEATURE:
<223> OTHER INFORMATION: Zinc Finger Protein Recognition Helices

<400> SEQUENCE: 85

Arg Ser Asp Ala Leu Ser Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 86

Asp Arg Ser Ala Leu Ala Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 87

Arg Ser Asp His Leu Ser Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 88

Asp Ser Gln Asn Arg Ile Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 89

Gln Ser Gly Asp Leu Thr Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 90

Asp Lys Gly Asn Leu Thr Lys
1               5

<210> SEQ ID NO 91
<211> LENGTH: 7
<212> TYPE: PRT
<213> ORGANISM: Artificial Sequence
<220> FEATURE:
```

<223> OTHER INFORMATION: Zinc Finger Protein Recognition Helices

<400> SEQUENCE: 91

Arg Ser Ala Asp Leu Thr Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 92

Asp Arg Ser His Leu Ala Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 93

Arg Ser Asp Thr Leu Ser Glu
1               5

<210> SEQ ID NO 94
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 94

Asp Arg Ser Asn Arg Lys Thr
1               5

<210> SEQ ID NO 95
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 95

Asp Arg Ser Asn Leu Ser Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 96

Leu Arg Gln Asp Leu Lys Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 97

Arg Ser Asp His Leu Ser Glu
1               5

<210> SEQ ID NO 98
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 98

Asp Arg Ser Ala Leu Ala Arg
1               5

<210> SEQ ID NO 99
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 99

Asp Arg Ser Ala Leu Ser Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 100

Asn Arg Arg Gly Arg Trp Ser
1               5

<210> SEQ ID NO 101
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 101

Arg Pro Tyr Thr Leu Arg Leu
1               5

<210> SEQ ID NO 102
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 102

His Arg Ser Ser Leu Arg Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Zinc Finger Protein Recognition Helices

```
<400> SEQUENCE: 103

Arg Ser Asp Ser Leu Leu Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 104

Trp Leu Ser Ser Leu Ser Ala
1               5

<210> SEQ ID NO 105
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 105

Gln Ser Gly Asp Leu Thr Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 106

Asp Arg Ser His Leu Ala Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 107

Asp Arg Ser Asn Leu Ser Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 108

Leu Lys Gln His Leu Asn Glu
1               5

<210> SEQ ID NO 109
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 109
```

```
Leu Arg His His Leu Thr Arg
1               5

<210> SEQ ID NO 110
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 110

Gln Ser Gly Asn Leu His Val
1               5

<210> SEQ ID NO 111
<211> LENGTH: 7
<212> TYPE: PRT
<213> ORGANISM: Artificial Sequence
<220> FEATURE:
<223> OTHER INFORMATION: Zinc Finger Protein Recognition Helices

<400> SEQUENCE: 111

Thr Ser Gly His Leu Ser Arg
1               5

<210> SEQ ID NO 112
<211> LENGTH: 22
<212> TYPE: DNA
<213> ORGANISM: Artificial Sequence
<220> FEATURE:
<223> OTHER INFORMATION: Zinc Finger Binding Sequences

<400> SEQUENCE: 112
ctactccgta tgcgaaggca cg                                          22

<210> SEQ ID NO 113
<211> LENGTH: 22
<212> TYPE: DNA
<213> ORGANISM: Artificial Sequence
<220> FEATURE:
<223> OTHER INFORMATION: Zinc Finger Binding Sequences

<400> SEQUENCE: 113
tattcgcggt gggacacttg at                                          22

<210> SEQ ID NO 114
<211> LENGTH: 22
<212> TYPE: DNA
<213> ORGANISM: Artificial Sequence
<220> FEATURE:
<223> OTHER INFORMATION: Zinc Finger Binding Sequences

<400> SEQUENCE: 114
ccggagccgg ggcctcccag gc                                          22

<210> SEQ ID NO 115
<211> LENGTH: 23
<212> TYPE: DNA
<213> ORGANISM: Artificial Sequence
<220> FEATURE:
<223> OTHER INFORMATION: Zinc Finger Binding Sequences

<400> SEQUENCE: 115
atcgcgacgc gacgcgacga gac                                         23
```

```
<210> SEQ ID NO 116
<211> LENGTH: 13
<212> TYPE: DNA
<213> ORGANISM: Artificial Sequence
<220> FEATURE:
<223> OTHER INFORMATION: Zinc Finger Binding Sequences

<400> SEQUENCE: 116
tgcatgcgca gta                                                          13

<210> SEQ ID NO 117
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 117
acaccggcgc acggcacg                                                     18

<210> SEQ ID NO 118
<211> LENGTH: 12
<212> TYPE: DNA
<213> ORGANISM: Artificial Sequence
<220> FEATURE:
<223> OTHER INFORMATION: Zinc Finger Binding Sequences

<400> SEQUENCE: 118
agaggtgtaa cc                                                           12

<210> SEQ ID NO 119
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 119
tcgggcacaa gaaacgag                                                     18

<210> SEQ ID NO 120
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 120
tacgctgaca atgca                                                        15

<210> SEQ ID NO 121
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 121
ccagctgatg gagaggac                                                     18

<210> SEQ ID NO 122
<211> LENGTH: 12
<212> TYPE: DNA
<213> ORGANISM: Artificial Sequence
<220> FEATURE:
<223> OTHER INFORMATION: Zinc Finger Binding Sequences
```

<400> SEQUENCE: 122
agagcaggcg ag                                          12

<210> SEQ ID NO 123
<211> LENGTH: 16
<212> TYPE: DNA
<213> ORGANISM: Artificial Sequence
<220> FEATURE:
<223> OTHER INFORMATION: Zinc Finger Binding Sequences

<400> SEQUENCE: 123
agcaaagtga gtagtt                                      16

<210> SEQ ID NO 124
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 124
tggatggaag gaatc                                       15

<210> SEQ ID NO 125
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 125
gaagctacat cccag                                       15

<210> SEQ ID NO 126
<211> LENGTH: 18
<212> TYPE: DNA
<213> ORGANISM: Artificial Sequence
<220> FEATURE:
<223> OTHER INFORMATION: Zinc Finger Binding Sequences

<400> SEQUENCE: 126
tacgcgcaac ggaacgca                                    18

<210> SEQ ID NO 127
<211> LENGTH: 19
<212> TYPE: DNA
<213> ORGANISM: Artificial Sequence
<220> FEATURE:
<223> OTHER INFORMATION: Zinc Finger Binding Sequences

<400> SEQUENCE: 127
caccggtgtc gtgtaacag                                   19

<210> SEQ ID NO 128
<211> LENGTH: 16
<212> TYPE: DNA
<213> ORGANISM: Artificial Sequence
<220> FEATURE:
<223> OTHER INFORMATION: Zinc Finger Binding Sequences

<400> SEQUENCE: 128
cccggacgac gccgag                                      16

<210> SEQ ID NO 129
<211> LENGTH: 20

```
<212> TYPE: DNA
<213> ORGANISM: Artificial Sequence
<220> FEATURE:
<223> OTHER INFORMATION: Zinc Finger Binding Sequences

<400> SEQUENCE: 129
gacatggcac gcgcatcgag                                                  20

<210> SEQ ID NO 130
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 130
gcatgtgtgg ttttg                                                       15

<210> SEQ ID NO 131
<211> LENGTH: 15
<212> TYPE: DNA
<213> ORGANISM: Artificial Sequence
<220> FEATURE:
<223> OTHER INFORMATION: Zinc Finger Binding Sequences

<400> SEQUENCE: 131
ggtcaaggta gtgac                                                       15

<210> SEQ ID NO 132
<211> LENGTH: 2378
<212> TYPE: DNA
<213> ORGANISM: Artificial Sequence
<220> FEATURE:
<223> OTHER INFORMATION: universal polynucleotide donor cassette
      sequence: pDAB111845

<400> SEQUENCE: 132
aagttggtga tacatgaacc aacacgaaga acccgccagt cctactacca ctctccttcg      60
tttgacctag ctggctggtt aagaaactga tgttgatacc agccactact ccgagctagt     120
agtaaaagat ttttacagcc aggggagcca caggttagta gagtggtagg agcagtgttg     180
gactgatggc tcgcttacat aagcagttct gtcccatgga gccaatgtcc tgatacggta     240
ggacacatat cccttaatga atcggccaac gcgcggggag aggcggtttg cgtattgggc     300
gctcttccgc ttcctcgctc actgactcgc tgcgctcggt cgttcggctg cggcgagcgg     360
tatcagctca ctcaaaggcg gtaatacggt tatccacaga atcaggggat aacgcaggaa     420
agaacatgtg agcaaaaggc cagcaaaagg ccaggaaccg taaaaaggcc gcgttgctgg     480 cgttttttcca taggctccgc cccccctgacg agcatcacaa aaatcgacgc tcaagtcaga     540
ggtggcgaaa cccgacagga ctataaagat accaggcgtt tccccctgga agctccctcg     600
tgcgctctcc tgttccgacc ctgccgctta ccggatacct gtccgccttt ctcccttcgg     660
gaagcgtggc gctttctcat agctcacgct gtaggtatct cagttcggtg taggtcgttc     720
gctccaagct gggctgtgtg cacgaacccc ccgttcagcc cgaccgctgc gccttatccg     780
gtaactatcg tcttgagtcc aacccggtaa gacacgactt atcgccactg gcagcagcca     840
ctggtaacag gattagcaga gcgaggtatg taggcggtgc tacagagttc ttgaagtggt     900
ggcctaacta cggctacact agaagaacag tatttggtat ctgcgctctg ctgaagccag     960
ttaccttcgg aaaaagagtt ggtagctctt gatccggcaa acaaaccacc gctggtagcg    1020
gtggtttttt tgtttgcaag cagcagatta cgcgcagaaa aaaaggatct caagaagatc    1080
```

```
ctttgatctt ttctacgggg tctgacgctc agtggaacga aaactcacgt taagggattt    1140
tggtcatggc gttcggaacc gtgctgaccc gcaagtggca acctcccgtg cctctgctca    1200
cctttaccgc ctggcaactg gcggccacct gcagggcgat cgcaccgagc gcttagtggg    1260
aatttgtacc cctatcgaa ccgggagcac aggatgacgc ctaacaattc attcaagccg    1320
acaccgcttc gcggcgcggc ttaattcagg agttaaacat catgagggaa gcggtgatcg    1380
ccgaagtatc gactcaacta tcagaggtag ttggcgtcat cgagcgccat ctcgaaccga    1440
cgttgctggc cgtacatttg tacggctccg cagtggatgg cggcctgaag ccacacagtg    1500
atattgattt gctggttacg gtgaccgtaa ggcttgatga acaacgcgg cgagctttga     1560 tcaacgacct tttggaaact tcggcttccc ctggagagag cgagattctc cgcgctgtag    1620
aagtcaccat tgttgtgcac gacgacatca ttccgtggcg ttatccagct aagcgcgaac    1680
tgcaatttgg agaatggcag cgcaatgaca ttcttgcagg tatcttcgag ccagccacga    1740
tcgacattga tctggctatc ttgctgacaa aagcaagaga acatagcgtt gccttggtag    1800
gtccagcggc ggaggaactc tttgatccgg ttcctgaaca ggatctattt gaggcgctaa    1860
atgaaacctt aacgctatgg aactcgccgc ccgactgggc tggcgatgag cgaaatgtag    1920
tgcttacgtt gtcccgcatt tggtacagcg cagtaaccgg caaaatcgcg ccgaaggatg    1980
tcgctgccga ctgggcaatg gagcgcctgc cggcccagta tcagcccgtc atacttgaag    2040
ctaggcaggc ttatcttgga caagaagatc gcttggcctc gcgcgcagat cagttggaag    2100
aatttgttca ctacgtgaaa ggcgagatca ccaaggtagt cggcaaataa tgtctaacaa    2160
ttcgttcaag ccgacgccgc ttcgcggcgc ggcttaactc aagcgttaga gagctgggga    2220
agactatgcg cgatcgcctg cagctacgtg ccttcgcata cggagtagtt tattcgcggt    2280
gggacacttg atagaaaggt taagaggaca cgcctaaaca gttgtgaata catacataca    2340
caccgataca cagatgctaa agcactaaag cccctaaa                           2378

<210> SEQ ID NO 133
<211> LENGTH: 2424
<212> TYPE: DNA
<213> ORGANISM: Artificial Sequence
<220> FEATURE:
<223> OTHER INFORMATION: universal polynucleotide donor cassette
      sequence: pDAB111846

<400> SEQUENCE: 133
tttgcgggat ctggatgggc tgttttcgcg cgcggcgtca ctttccctta acttctcgcg      60
ctggaagagg cagctgcctg cttttgcttg gccgctgacc atgacacctg ccccgctttt     120
gcagcccgtg gaggactctt ggcgagccac aggttagtag agtggtagga gcagtgttgg    180
actgatggct cgcttacata agcagttctg tcccatggag ccaatgtcct gatacggtag    240
gacacatatc ccttaatgaa tcggccaacg cgcggggaga ggcggtttgc gtattgggcg    300
ctcttccgct tcctcgctca ctgactcgct gcgctcggtc gttcggctgc ggcgagcggt    360
atcagctcac tcaaaggcgg taatacggtt atccacagaa tcagggata acgcaggaaa    420 gaacatgtga gcaaaaggcc agcaaaaggc caggaaccgt aaaaaggccg cgttgctggc    480 gttttccat aggctccgcc cccctgacga gcatcacaaa aatcgacgct caagtcagag    540
gtggcgaaac ccgacaggac tataaagata ccaggcgttt ccccctggaa gctccctcgt    600
gcgctctcct gttccgaccc tgccgcttac cggatacctg tccgcctttc tcccttcggg    660
aagcgtggcg ctttctcata gctcacgctg taggtatctc agttcggtgt aggtcgttcg    720
```

```
ctccaagctg ggctgtgtgc acgaaccccc cgttcagccc gaccgctgcg ccttatccgg       780
taactatcgt cttgagtcca acccggtaag acacgactta tcgccactgg cagcagccac       840
tggtaacagg attagcagag cgaggtatgt aggcggtgct acagagttct gaagtggtg        900 gcctaactac ggctacacta agaacagt atttggtatc tgcgctctgc tgaagccagt         960
taccttcgga aaagagttg gtagctcttg atccggcaaa caaaccaccg ctggtagcgg        1020
tggttttttt gtttgcaagc agcagattac gcgcagaaaa aaaggatctc aagaagatcc      1080
tttgatcttt tctacggggt ctgacgctca gtggaacgaa aactcacgtt aagggatttt      1140
ggtcatggct tcggaaccg tgctgacccg caagtggcaa cctcccgtgc ctctgctcac        1200
ctttaccgcc tggcaactgg cggccacctg cagggcgatc gcaccgagcg cttagtggga      1260
atttgtaccc cttatcgaac cgggagcaca ggatgacgcc taacaattca ttcaagccga      1320
caccgcttcg cggcgcggct taattcagga gttaaacatc atgagggaag cggtgatcgc      1380
cgaagtatcg actcaactat cagaggtagt tggcgtcatc gagcgccatc tcgaaccgac      1440
gttgctggcc gtacatttgt acggctccgc agtggatggc ggcctgaagc cacacagtga      1500
tattgatttg ctggttacgg tgaccgtaag gcttgatgaa acaacgcggc gagctttgat      1560
caacgacctt ttggaaactt cggcttcccc tggagagagc gagattctcc gcgctgtaga      1620
agtcaccatt gttgtgcacg acgacatcat tccgtggcgt tatccagcta agcgcgaact      1680
gcaatttgga gaatggcagc gcaatgacat tcttgcaggt atcttcgagc cagccacgat      1740
cgacattgat ctggctatct tgctgacaaa agcaagagaa catagcgttg ccttggtagg      1800
tccagcggcg gaggaactct ttgatccggt tcctgaacag gatctatttg aggcgctaaa      1860
tgaaacctta acgctatgga actcgccgcc cgactgggct ggcgatgagc gaaatgtagt      1920
gcttacgttg tcccgcattt ggtacagcgc agtaaccggc aaaatcgcgc cgaaggatgt      1980
cgctgccgac tggcaatgg agcgcctgcc ggcccagtat cagcccgtca tacttgaagc       2040
taggcaggct tatcttggac aagaagatcg cttggcctcg cgcgcagatc agttggaaga      2100
atttgttcac tacgtgaaag gcgagatcac caaggtagtc ggcaaataat gtctaacaat      2160
tcgttcaagc cgacgccgct tcgcggcgcg gcttaactca agcgttagag agctggggaa      2220
gactatgcgc gatcgcctgc aggtggttgc ctgggaggcc ccggctccgg catcgcgac       2280 gcgacgcgac gagacgcgta aaagtcaccc gtcgcggtct cgcatgcgcg agggaggcag      2340
gcaggcagcg aacaaaatcg cacgcgcgtc gtcgactgcc tggcctggcc tggtccagct      2400
gaaaaccgcc ccggtttgcc tccg                                             2424
```

<210> SEQ ID NO 134
<211> LENGTH: 2225
<212> TYPE: DNA
<213> ORGANISM: Artificial Sequence
<220> FEATURE:
<223> OTHER INFORMATION: universal polynucleotide donor cassette
      sequence: pDAB117415

<400> SEQUENCE: 134

```
gcgtattggg cgctcttccg cttcctcgct cactgactcg ctgcgctcgg tcgttcggct        60
gcggcgagcg gtatcagctc actcaaaggc ggtaatacgg ttatccacag aatcagggga      120
taacgcagga agaacatgt gagcaaaagg ccagcaaaag gccaggaacc gtaaaaaggc       180
cgcgttgctg gcgtttttcc ataggctccg ccccccctgac gagcatcaca aaaatcgacg      240
ctcaagtcag aggtggcgaa acccgacagg actataaaga taccaggcgt ttccccctgg      300
```

```
aagctccctc gtgcgctctc ctgttccgac cctgccgctt accggatacc tgtccgcctt      360
tctcccttcg ggaagcgtgg cgctttctca tagctcacgc tgtaggtatc tcagttcggt      420
gtaggtcgtt cgctccaagc tgggctgtgt gcacgaaccc ccgttcagc ccgaccgctg       480 cgccttatcc ggtaactatc gtcttgagtc caacccggta agacacgact tatcgccact      540
ggcagcagcc actggtaaca ggattagcag agcgaggtat gtaggcggtg ctacagagtt      600
cttgaagtgg tggcctaact acggctacac tagaagaaca gtatttggta tctgcgctct      660
gctgaagcca gttaccttcg gaaaagagt tggtagctct tgatccggca aacaaaccac        720
cgctggtagc ggtggttttt ttgtttgcaa gcagcagatt acgcgcagaa aaaaaggatc      780
tcaagaagat cctttgatct tttctacggg gtctgacgct cagtggaacg aaaactcacg      840
ttaagggatt ttggtcatgg cgttcggaac cgtgctgacc cgcaagtggc aacctcccgt      900
gcctctgctc acctttaccg cctggcaact ggcggccacc tgcagggcga tcgcaccgag      960
cgcttagtgg gaatttgtac cccttatcga accgggagca caggatgacg cctaacaatt     1020
cattcaagcc gacaccgctt cgcggcgcgg cttaattcag gagttaaaca tcatgaggga     1080
agcggtgatc gccgaagtat cgactcaact atcagaggta gttggcgtca tcgagcgcca     1140
tctcgaaccg acgttgctgg ccgtacattt gtacggctcc gcagtggatg gcggcctgaa     1200
gccacacagt gatattgatt tgctggttac ggtgaccgta aggcttgatg aaacaacgcg     1260
gcgagctttg atcaacgacc ttttggaaac ttcggcttcc cctggagaga gcgagattct     1320
ccgcgctgta gaagtcacca ttgttgtgca cgacgacatc attccgtggc gttatccagc     1380
taagcgcgaa ctgcaatttg gagaatggca gcgcaatgac attcttgcag gtatcttcga     1440
gccagccacg atcgacattg atctggctat cttgctgaca aaagcaagag aacatagcgt     1500
tgccttggta ggtccagcgg cggaggaact ctttgatccg gttcctgaac aggatctatt     1560
tgaggcgcta aatgaaacct aacgctatg gaactcgccg cccgactggg ctggcgatga     1620
gcgaaatgta gtgcttacgt tgtcccgcat ttggtacagc gcagtaaccg gcaaaatcgc     1680
gccgaaggat gtcgctgccg actgggcaat ggagcgcctg ccggcccagt atcagcccgt     1740
catacttgaa gctaggcagg cttatcttgg acaagaagat cgcttggcct cgcgcgcaga     1800
tcagttggaa gaatttgttc actacgtgaa aggcgagatc accaaggtag tcggcaaata     1860
atgtctaaca attcgttcaa gccgacgccg cttcgcggcg cggcttaact caagcgttag     1920
agagctgggg aagactatgc gcgatcgcct gcagtccgca gttaccttcc ccatcatgaa     1980
cttggagacc gaaaggtgtg gtgcctagtt accccgaaga aatgaaacat ctgcattgtc     2040
agcgtagtat cccagctgat ggagaggaca tacccatgag gagccacagg ttagtagagt     2100
ggtaggagca gtgttggact gatggctcgc ttacataagc agttctgtcc catggagcca     2160
atgtcctgat acggtaggac acatatccct taatgaatcg gccaacgcgc ggggagaggc     2220
ggttt                                                                2225
```

<210> SEQ ID NO 135
<211> LENGTH: 2234
<212> TYPE: DNA
<213> ORGANISM: Artificial Sequence
<220> FEATURE:
<223> OTHER INFORMATION: universal polynucleotide donor cassette
      sequence: pDAB117416

<400> SEQUENCE: 135

```
gagagctggg gaagactatg cgcgatcgcc tgcagtgtcg cgaggcaggg agcagccgcg       60
```

```
tgtccgcctg ctgctgctgg aatggcgcgg tggccgcgcg cggtgacgtc ggcaaggctg      120
gtctcgcctg ctcttggcaa gcaaagtgag tagttacacg gcgctggctg gagccacagg      180
ttagtagagt ggtaggagca gtgttggact gatggctcgc ttacataagc agttctgtcc      240
catggagcca atgtcctgat acggtaggac acatatccct taatgaatcg gccaacgcgc      300
ggggagaggc ggtttgcgta ttgggcgctc ttccgcttcc tcgctcactg actcgctgcg      360
ctcggtcgtt cggctgcggc gagcggtatc agctcactca aaggcggtaa tacggttatc      420
cacagaatca ggggataacg caggaaagaa catgtgagca aaaggccagc aaaaggccag      480
gaaccgtaaa aaggccgcgt tgctggcgtt tttccatagg ctccgccccc ctgacgagca      540
tcacaaaaat cgacgctcaa gtcagaggtg gcgaaaccco acaggactat aaagatacca      600
ggcgtttccc cctggaagct ccctcgtgcg ctctcctgtt ccgaccctgc cgcttaccgg      660
atacctgtcc gcctttctcc cttcgggaag cgtggcgctt tctcatagct cacgctgtag      720
gtatctcagt tcggtgtagg tcgttcgctc caagctgggc tgtgtgcacg aaccccccgt      780
tcagcccgac cgctgcgcct tatccggtaa ctatcgtctt gagtccaacc cggtaagaca      840
cgacttatcg ccactggcag cagccactgg taacaggatt agcagagcga ggtatgtagg      900
cggtgctaca gagttcttga agtggtggcc taactacggc tacactagaa gaacagtatt      960
tggtatctgc gctctgctga agccagttac cttcggaaaa agagttggta gctcttgatc     1020
cggcaaacaa accaccgctg gtagcggtgg tttttttgtt tgcaagcagc agattacgcg     1080
cagaaaaaaa ggatctcaag aagatccttt gatcttttct acggggtctg acgctcagtg     1140
gaacgaaaac tcacgttaag ggattttggt catggcgttc ggaaccgtgc tgacccgcaa     1200
gtggcaacct cccgtgcctc tgctcacctt taccgcctgg caactggcgg ccacctgcag     1260
ggcgatcgca ccgagcgctt agtgggaatt tgtaccccct atcgaaccgg gagcacagga     1320
tgacgcctaa caattcattc aagccgacac cgcttcgcgg cgcggcttaa ttcaggagtt     1380
aaacatcatg agggaagcgg tgatcgccga agtatcgact caactatcag aggtagttgg     1440
cgtcatcgag cgccatctcg aaccgacgtt gctggccgta catttgtacg gctccgcagt     1500
ggatggcggc ctgaagccac acagtgatat tgatttgctg gttacggtga ccgtaaggct     1560
tgatgaaaca acgcggcgag cttttgatcaa cgaccttttg gaaacttcgg cttcccctgg     1620
agagagcgag attctccgcg ctgtagaagt caccattgtt gtgcacgacg acatcattcc     1680
gtggcgttat ccagctaagc gcgaactgca atttggagaa tggcagcgca atgacattct     1740
tgcaggtatc ttcgagccag ccacgatcga cattgatctg ctatcttgc tgacaaaagc     1800 aagagaacat agcgttgcct tggtaggtcc agcggcggag gaactctttg atccggttcc     1860
tgaacaggat ctatttgagg cgctaaatga aaccttaacg ctatggaact cgccgcccga     1920
ctgggctggc gatgagcgaa atgtagtgct tacgttgtcc cgcatttggt acagcgcagt     1980
aaccggcaaa atcgcgccga aggatgtcgc tgccgactgg gcaatggagc gcctgccggc     2040
ccagtatcag cccgtcatac ttgaagctag gcaggcttat cttggacaag aagatcgctt     2100
ggcctcgcgc gcagatcagt tggaagaatt tgttcactac gtgaaaggcg agatcaccaa     2160
ggtagtcggc aaataatgtc taacaattcg ttcaagccga cgccgcttcg cggcgcggct     2220
taactcaagc gtta                                                       2234
```

<210> SEQ ID NO 136
<211> LENGTH: 2165
<212> TYPE: DNA

<213> ORGANISM: Artificial Sequence
<220> FEATURE:
<223> OTHER INFORMATION: universal polynucleotide donor cassette sequence: pDAB117417

<400> SEQUENCE: 136

```
gagagctggg gaagactatg cgcgatcgcc tgcagtgttg tgcagccgta cgtgccgtgc      60
gccggtgtat gtctgcatgc gcagtactta ttttctgaag cgagccacag gttagtagag     120
tggtaggagc agtgttggac tgatggctcg cttacataag cagttctgtc ccatggagcc     180
aatgtcctga tacggtagga cacatatccc ttaatgaatc ggccaacgcg cggggagagg     240
cggtttgcgt attgggcgct cttccgcttc ctcgctcact gactcgctgc gctcggtcgt     300
tcggctgcgg cgagcggtat cagctcactc aaaggcggta atacggttat ccacagaatc     360
aggggataac gcaggaaaga acatgtgagc aaaaggccag caaaaggcca ggaaccgtaa     420
aaaggccgcg ttgctggcgt ttttccatag gctccgcccc cctgacgagc atcacaaaaa     480
tcgacgctca gtcagaggt ggcgaaaccc gacaggacta taaagatacc aggcgtttcc     540
ccctggaagc tccctcgtgc gctctcctgt tccgaccctg ccgcttaccg gatacctgtc     600
cgcctttctc ccttcgggaa gcgtggcgct ttctcatagc tcacgctgta ggtatctcag     660
ttcggtgtag gtcgttcgct ccaagctggg ctgtgtgcac gaaccccccg ttcagcccga     720
ccgctgcgcc ttatccggta actatcgtct tgagtccaac ccggtaagac acgacttatc     780
gccactggca gcagccactg gtaacaggat tagcagagcg aggtatgtag gcggtgctac     840
agagttcttg aagtggtggc ctaactacgg ctacactaga agaacagtat ttggtatctg     900
cgctctgctg aagccagtta ccttcggaaa aagagttggt agctcttgat ccggcaaaca     960
aaccaccgct ggtagcggtg gtttttttgt ttgcaagcag cagattacgc gcagaaaaaa    1020
aggatctcaa gaagatcctt tgatctttc tacggggtct gacgctcagt ggaacgaaaa    1080
ctcacgttaa gggattttgg tcatggcgtt cggaaccgtg ctgacccgca agtggcaacc    1140
tcccgtgcct ctgctcacct ttaccgcctg gcaactggcg gccacctgca gggcgatcgc    1200
accgagcgct tagtgggaat tgtaccccct tatcgaaccg ggagcacagg atgacgccta    1260
acaattcatt caagccgaca ccgcttcgcg gcgcggctta attcaggagt taaacatcat    1320
gagggaagcg gtgatcgccg aagtatcgac tcaactatca gaggtagttg gcgtcatcga    1380
gcgccatctc gaaccgacgt tgctggccgt acatttgtac ggctccgcag tggatggcgg    1440
cctgaagcca cacagtgata ttgatttgct ggttacggtg accgtaaggc ttgatgaaac    1500
aacgcggcga gctttgatca acgacctttt ggaaacttcg gcttccctg gagagagcga    1560
gattctccgc gctgtagaag tcaccattgt tgtgcacgac gacatcattc cgtggcgtta    1620
tccagctaag cgcgaactgc aatttggaga atggcagcgc aatgacattc ttgcaggtat    1680
cttcgagcca gccacgatcg acattgatct ggctatcttg ctgacaaaag caagagaaca    1740
tagcgttgcc ttggtaggtc cagcggcgga ggaactcttt gatccggttc ctgaacagga    1800
tctatttgag gcgctaaatg aaaccttaac gctatggaac tcgccgcccg actgggctgg    1860
cgatgagcga aatgtagtgc ttacgttgtc ccgcatttgg tacagcgcag taaccggcaa    1920
aatcgcgccg aaggatgtcg ctgccgactg gcaatggagc gcctgccgg cccagtatca    1980
gcccgtcata cttgaagcta ggcaggctta tcttggacaa gaagatcgct tggcctcgcg    2040
cgcagatcag ttggaagaat ttgttcacta cgtgaaaggc gagatcacca aggtagtcgg    2100
caaataatgt ctaacaattc gttcaagccg acgccgcttc gcggcgcggc ttaactcaag    2160
``` cgtta 2165

<210> SEQ ID NO 137
<211> LENGTH: 2264
<212> TYPE: DNA
<213> ORGANISM: Artificial Sequence
<220> FEATURE:
<223> OTHER INFORMATION: universal polynucleotide donor cassette
sequence: pDAB117419

<400> SEQUENCE: 137

```
gagagctggg gaagactatg cgcgatcgcc tgcagtaacg atttattttc ctcgtttctt    60
gtgcccgaaa gagagaggtg taacccatcc tctataacag tgtggctttg acaacggttc   120
aatatgtatg tttggcaaat gtagatttgt gccaattctt ggtcataatc agcgcggaca   180
aaccggctac ccaaatttgg gagccacagg ttagtagagt ggtaggagca gtgttggact   240
gatggctcgc ttacataagc agttctgtcc catggagcca atgtcctgat acggtaggac   300
acatatccct taatgaatcg gccaacgcgc ggggagaggc ggtttgcgta ttgggcgctc   360
ttccgcttcc tcgctcactg actcgctgcg ctcggtcgtt cggctgcggc gagcggtatc   420
agctcactca aaggcggtaa tacggttatc cacagaatca ggggataacg caggaaagaa   480
catgtgagca aaaggccagc aaaaggccag gaaccgtaaa aaggccgcgt tgctggcgtt   540
ttccatagg ctccgccccc ctgacgagca tcacaaaaat cgacgctcaa gtcagaggtg   600
gcgaaacccg acaggactat aaagatacca ggcgtttccc cctggaagct ccctcgtgcg   660
ctctcctgtt ccgaccctgc cgcttaccgg atacctgtcc gcctttctcc cttcgggaag   720
cgtggcgctt tctcatagct cacgctgtag gtatctcagt tcggtgtagg tcgttcgctc   780
caagctgggc tgtgtgcacg aaccccccgt tcagcccgac cgctgcgcct tatccggtaa   840
ctatcgtctt gagtccaacc cggtaagaca cgacttatcg ccactggcag cagccactgg   900
taacaggatt agcagagcga ggtatgtagg cggtgctaca gagttcttga agtggtggcc   960
taactacggc tacactagaa gaacagtatt tggtatctgc gctctgctga agccagttac  1020
cttcggaaaa agagttggta gctcttgatc cggcaaacaa accaccgctg gtagcggtgg  1080
tttttttgtt tgcaagcagc agattacgcg cagaaaaaaa ggatctcaag aagatccttt  1140
gatcttttct acgggtgtctg acgctcagtg gaacgaaaac tcacgttaag ggattttggt  1200
catgcgttc ggaaccgtgc tgacccgcaa gtggcaacct cccgtgcctc tgctcacctt  1260
taccgcctgg caactggcgg ccacctgcag ggcgatcgca ccgagcgctt agtgggaatt  1320
tgtacccctt atcgaaccgg gagcacagga tgacgcctaa caattcattc aagccgacac  1380
cgcttcgcgg cgcggcttaa ttcaggagtt aaacatcatg agggaagcgg tgatcgccga  1440
agtatcgact caactatcag aggtagttgg cgtcatcgag cgccatctcg aaccgacgtt  1500
gctggccgta catttgtacg gctccgcagt ggatggcggc ctgaagccac acagtgatat  1560
tgatttgctg gttacggtga ccgtaaggct tgatgaaaca acgcggcgag ctttgatcaa  1620
cgacctttg gaaacttcgg cttcccctgg agagagcgag attctccgcg ctgtagaagt  1680
caccattgtt gtgcacgacg acatcattcc gtggcgttat ccagctaagc gcgaactgca  1740
atttggagaa tggcagcgca atgacattct tgcaggtatc ttcgagccag ccacgatcga  1800
cattgatctg gctatcttgc tgacaaaagc aagagaacat agcgttgcct tggtaggtcc  1860
agcggcggag gaactctttg atccggttcc tgaacaggat ctatttgagg cgctaaatga  1920
aaccttaacg ctatggaact cgccgcccga ctgggctggc gatgagcgaa atgtagtgct  1980
```

| tacgttgtcc cgcatttggt acagcgcagt aaccggcaaa atcgcgccga aggatgtcgc | 2040 |
| tgccgactgg gcaatggagc gcctgccggc ccagtatcag cccgtcatac ttgaagctag | 2100 |
| gcaggcttat cttggacaag aagatcgctt ggcctcgcgc gcagatcagt tggaagaatt | 2160 |
| tgttcactac gtgaaaggcg agatcaccaa ggtagtcggc aaataatgtc taacaattcg | 2220 |
| ttcaagccga cgccgcttcg cggcgcggct taactcaagc gtta | 2264 |

<210> SEQ ID NO 138
<211> LENGTH: 2373
<212> TYPE: DNA
<213> ORGANISM: Artificial Sequence
<220> FEATURE:
<223> OTHER INFORMATION: universal polynucleotide donor cassette
    sequence: pDAB117434

<400> SEQUENCE: 138

| gcgtattggg cgctcttccg cttcctcgct cactgactcg ctgcgctcgg tcgttcggct | 60 |
| gcggcgagcg gtatcagctc actcaaaggc ggtaatacgg ttatccacag aatcagggga | 120 |
| taacgcagga agaacatgt gagcaaaagg ccagcaaaag gccaggaacc gtaaaaaggc | 180 |
| cgcgttgctg gcgtttttcc ataggctccg cccccctgac gagcatcaca aaaatcgacg | 240 |
| ctcaagtcag aggtggcgaa acccgacagg actataaaga taccaggcgt ttccccctgg | 300 |
| aagctccctc gtgcgctctc ctgttccgac cctgccgctt accggatacc tgtccgcctt | 360 |
| tctcccttcg ggaagcgtgg cgctttctca tagctcacgc tgtaggtatc tcagttcggt | 420 |
| gtaggtcgtt cgctccaagc tgggctgtgt gcacgaaccc cccgttcagc ccgaccgctg | 480 |
| cgccttatcc ggtaactatc gtcttgagtc aacccggta agacacgact tatcgccact | 540 |
| ggcagcagcc actggtaaca ggattagcag agcgaggtat gtaggcggtg ctacagagtt | 600 |
| cttgaagtgg tggcctaact acggctacac tagaagaaca gtatttggta tctgcgctct | 660 |
| gctgaagcca gttaccttcg gaaaaagagt tggtagctct tgatccggca acaaaccac | 720 |
| cgctggtagc ggtggttttt tgtttgcaa gcagcagatt acgcgcagaa aaaaaggatc | 780 |
| tcaagaagat cctttgatct tttctacggg gtctgacgct cagtggaacg aaaactcacg | 840 |
| ttaagggatt ttggtcatgg cgttcggaac cgtgctgacc cgcaagtggc aacctcccgt | 900 |
| gcctctgctc acctttaccg cctggcaact ggcggccacc tgcagggcga tcgcaccgag | 960 |
| cgcttagtgg gaatttgtac cccttatcga accgggagca caggatgacg cctaacaatt | 1020 |
| cattcaagcc gacaccgctt cgcggcgcgg cttaattcag gagttaaaca tcatgaggga | 1080 |
| agcggtgatc gccgaagtat cgactcaact atcagaggta gttggcgtca tcgagcgcca | 1140 |
| tctcgaaccg acgttgctgg ccgtacattt gtacggctcc gcagtggatg gcggcctgaa | 1200 |
| gccacacagt gatattgatt tgctggttac ggtgaccgta aggcttgatg aaacaacgcg | 1260 |
| gcgagctttg atcaacgacc ttttggaaac ttcggcttcc cctggagaga gcgagattct | 1320 |
| ccgcgctgta gaagtcacca ttgttgtgca cgacgcatc attccgtggc gttatccagc | 1380 |
| taagcgcgaa ctgcaatttg gagaatggca gcgcaatgac attcttgcag gtatcttcga | 1440 |
| gccagccacg atcgacattg atctggctat cttgctgaca aaagcaagag aacatagcgt | 1500 |
| tgccttggta ggtccagcgg cggaggaact ctttgatccg gttcctgaac aggatctatt | 1560 |
| tgaggcgcta aatgaaacct aacgctatg gaactcgccg cccgactggg ctggcgatga | 1620 |
| gcgaaatgta gtgcttacgt tgtcccgcat ttggtacagc gcagtaaccg gcaaaatcgc | 1680 |
| gccgaaggat gtcgctgccg actgggcaat ggagcgcctg ccggcccagt atcagcccgt | 1740 |

| | |
|---|---|
| catacttgaa gctaggcagg cttatcttgg acaagaagat cgcttggcct cgcgcgcaga | 1800 |
| tcagttggaa gaatttgttc actacgtgaa aggcgagatc accaaggtag tcggcaaata | 1860 |
| atgtctaaca attcgttcaa gccgacgccg cttcgcggcg cggcttaact caagcgttag | 1920 |
| agagctgggg aagactatgc gcgatcgcct gcagataagg aactatatac aaaaccacac | 1980 |
| atgcacacgt ggtcaaggta gtgactaatc tcgcctaata cacggcgctg gctgatgcat | 2040 |
| gcgtgacacg gtggctagct agctgttgat cccggccggc ccgtgatgac agcgctcggc | 2100 |
| gtcttcaggc ttcagaaccg ttgatcaagg acgatgagct tgagagctga atccgcggtt | 2160 |
| cgtggtgttc atctcagcgt gtctcgtcgt cggcccggtc ggcagcggca gaatttcatt | 2220 |
| tcagactgga gccacaggtt agtagagtgg taggagcagt gttggactga tggctcgctt | 2280 |
| acataagcag ttctgtccca tggagccaat gtcctgatac ggtaggacac atatccctta | 2340 |
| atgaatcggc caacgcgcgg ggagaggcgg ttt | 2373 |

<210> SEQ ID NO 139
<211> LENGTH: 2241
<212> TYPE: DNA
<213> ORGANISM: Artificial Sequence
<220> FEATURE:
<223> OTHER INFORMATION: universal polynucleotide donor cassette
  sequence: pDAB117418

<400> SEQUENCE: 139

| | |
|---|---|
| gagagctggg gaagactatg cgcgatcgcc tgcaggagct tgcattaact agcaaagtga | 60 |
| ttccttccat ccatgcaaga agctacatcc cagtgggtgc ggcaaaagct gtatgaaaag | 120 |
| gttggagact tccatacaac tgttgtgtgt cgagtagtag aaaccaacaa caaagtcgag | 180 |
| ccacaggtta gtagagtggt aggagcagtg ttggactgat ggctcgctta cataagcagt | 240 |
| tctgtcccat ggagccaatg tcctgatacg gtaggacaca tatcccttaa tgaatcggcc | 300 |
| aacgcgcggg gagaggcggt ttgcgtattg ggcgctcttc cgcttcctcg ctcactgact | 360 |
| cgctgcgctc ggtcgttcgg ctgcggcgag cggtatcagc tcactcaaag gcggtaatac | 420 |
| ggttatccac agaatcaggg gataacgcag gaaagaacat gtgagcaaaa ggccagcaaa | 480 |
| aggccaggaa ccgtaaaaag gccgcgttgc tggcgttttt ccataggctc cgcccccctg | 540 |
| acgagcatca caaaaatcga cgctcaagtc agaggtggcg aaacccgaca ggactataaa | 600 |
| gataccaggc gtttccccct ggaagctccc tcgtgcgctc tcctgttccg accctgccgc | 660 |
| ttaccggata cctgtccgcc tttctccctt cgggaagcgt ggcgctttct catagctcac | 720 |
| gctgtaggta tctcagttcg gtgtaggtcg ttcgctccaa gctgggctgt gtgcacgaac | 780 |
| cccccgttca gcccgaccgc tgcgccttat ccggtaacta tcgtcttgag tccaacccgg | 840 |
| taagacacga cttatcgcca ctggcagcag ccactggtaa caggattagc agagcgaggt | 900 |
| atgtaggcgg tgctacagag ttcttgaagt ggtggcctaa ctacggctac actagaagaa | 960 |
| cagtatttgg tatctgcgct ctgctgaagc cagttacctt cggaaaaaga gttggtagct | 1020 |
| cttgatccgg caaacaaacc accgctggta gcggtggttt ttttgtttgc aagcagcaga | 1080 |
| ttacgcgcag aaaaaaagga tctcaagaag atcctttgat cttttctacg ggtctgacg | 1140 |
| ctcagtggaa cgaaaactca cgttaaggga ttttggtcat ggcgttcgga accgtgctga | 1200 |
| cccgcaagtg gcaacctccc gtgcctctgc tcacctttac cgcctggcaa ctggcggcca | 1260 |
| cctgcagggc gatcgcaccg agcgcttagt gggaatttgt acccttatc gaaccggag | 1320 |
| cacaggatga cgcctaacaa ttcattcaag ccgacaccgc ttcgcggcgc ggcttaattc | 1380 |

| aggagttaaa catcatgagg gaagcggtga tcgccgaagt atcgactcaa ctatcagagg | 1440 |
| tagttggcgt catcgagcgc catctcgaac cgacgttgct ggccgtacat ttgtacggct | 1500 |
| ccgcagtgga tggcggcctg aagccacaca gtgatattga tttgctggtt acggtgaccg | 1560 |
| taaggcttga tgaaacaacg cggcgagctt tgatcaacga ccttttggaa acttcggctt | 1620 |
| cccctggaga gagcgagatt ctccgcgctg tagaagtcac cattgttgtg cacgacgaca | 1680 |
| tcattccgtg gcgttatcca gctaagcgcg aactgcaatt tggagaatgg cagcgcaatg | 1740 |
| acattcttgc aggtatcttc gagccagcca cgatcgacat tgatctggct atcttgctga | 1800 |
| caaaagcaag agaacatagc gttgccttgg taggtccagc ggcggaggaa ctctttgatc | 1860 |
| cggttcctga acaggatcta tttgaggcgc taaatgaaac cttaacgcta tggaactcgc | 1920 |
| cgcccgactg gctggcgat gagcgaaatg tagtgcttac gttgtcccgc atttggtaca | 1980 |
| gcgcagtaac cggcaaaatc gcgccgaagg atgtcgctgc cgactgggca atggagcgcc | 2040 |
| tgccggccca gtatcagccc gtcatacttg aagctaggca ggcttatctt ggacaagaag | 2100 |
| atcgcttggc ctcgcgcgca gatcagttgg aagaatttgt tcactacgtg aaaggcgaga | 2160 |
| tcaccaaggt agtcggcaaa taatgtctaa caattcgttc aagccgacgc cgcttcgcgg | 2220 |
| cgcggcttaa ctcaagcgtt a | 2241 |

<210> SEQ ID NO 140
<211> LENGTH: 2195
<212> TYPE: DNA
<213> ORGANISM: Artificial Sequence
<220> FEATURE:
<223> OTHER INFORMATION: universal polynucleotide donor cassette
      sequence: pDAB117420

<400> SEQUENCE: 140

| gagagctggg gaagactatg cgcgatcgcc tgcagggacc ccgtcgccgt cggcacagcg | 60 |
| tcagggcggt aacatgcgtt ccgttgcgcg tacggaccac cggtgtcgtg taacaggaag | 120 |
| agctgtcagt ggagccacag gttagtagag tggtaggagc agtgttggac tgatggctcg | 180 |
| cttacataag cagttctgtc ccatggagcc aatgtcctga tacggtagga cacatatccc | 240 |
| ttaatgaatc ggccaacgcg cggggagagg cggtttgcgt attgggcgct cttccgcttc | 300 |
| ctcgctcact gactcgctgc gctcggtcgt tcggctgcgg cgagcggtat cagctcactc | 360 |
| aaaggcggta atacggttat ccacagaatc aggggataac gcaggaaaga acatgtgagc | 420 |
| aaaaggccag caaaaggcca ggaaccgtaa aaaggccgcg ttgctggcgt ttttccatag | 480 |
| gctccgcccc cctgacgagc atcacaaaaa tcgacgctca gtcagaggt ggcgaaaccc | 540 |
| gacaggacta taaagatacc aggcgtttcc ccctggaagc tccctcgtgc gctctcctgt | 600 |
| tccgaccctg ccgcttaccg gatacctgtc cgcctttctc ccttcgggaa gcgtggcgct | 660 |
| ttctcatagc tcacgctgta ggtatctcag ttcggtgtag tcgttcgct ccaagctggg | 720 |
| ctgtgtgcac gaaccccccg ttcagcccga ccgctgcgcc ttatccggta actatcgtct | 780 |
| tgagtccaac ccggtaagac acgacttatc gccactggca gcagccactg gtaacaggat | 840 |
| tagcagagcg aggtatgtag gcggtgctac agagttcttg aagtggtggc ctaactacgg | 900 |
| ctacactaga agaacagtat ttggtatctg cgctctgctg aagccagtta ccttcggaaa | 960 |
| aagagttggt agctcttgat ccggcaaaca aaccaccgct ggtagcggtg ttttttgt | 1020 |
| ttgcaagcag cagattacgc gcagaaaaaa aggatctcaa gaagatcctt tgatcttttc | 1080 |
| tacggggtct gacgctcagt ggaacgaaaa ctcacgttaa gggattttgg tcatggcgtt | 1140 |

```
cggaaccgtg ctgacccgca agtggcaacc tcccgtgcct ctgctcacct ttaccgcctg     1200
gcaactggcg gccacctgca gggcgatcgc accgagcgct tagtgggaat ttgtacccct     1260
tatcgaaccg ggagcacagg atgacgccta acaattcatt caagccgaca ccgcttcgcg     1320
gcgcggctta attcaggagt taaacatcat gagggaagcg gtgatcgccg aagtatcgac     1380
tcaactatca gaggtagttg cgtcatcga cgccatctc gaaccgacgt tgctggccgt     1440
acatttgtac ggctccgcag tggatggcgg cctgaagcca cacagtgata ttgatttgct     1500
ggttacggtg accgtaaggc ttgatgaaac aacgcggcga gctttgatca acgacctttt     1560
ggaaacttcg gcttcccctg agagagcga gattctccgc gctgtagaag tcaccattgt     1620
tgtgcacgac gacatcattc cgtggcgtta ccagctaag cgcgaactgc aatttggaga     1680
atggcagcgc aatgcattc ttgcaggtat cttcgagcca gccacgatcg acattgatct     1740
ggctatcttg ctgacaaaag caagagaaca tagcgttgcc ttggtaggtc cagcggcgga     1800
ggaactcttt gatccggttc ctgaacagga tctatttgag gcgctaaatg aaaccttaac     1860
gctatggaac tcgccgcccg actgggctgg cgatgagcga aatgtagtgc ttacgttgtc     1920
ccgcatttgg tacagcgcag taaccggcaa atcgcgccg aaggatgtcg ctgccgactg     1980
ggcaatggag cgcctgccgg cccagtatca gcccgtcata cttgaagcta ggcaggctta     2040
tcttggacaa gaagatcgct tggcctcgcg cgcagatcag ttggaagaat tgttcacta     2100 cgtgaaaggc gagatcacca aggtagtcgg caaataatgt ctaacaattc gttcaagccg     2160
acgccgcttc gcggcgcggc ttaactcaag cgtta                               2195

<210> SEQ ID NO 141
<211> LENGTH: 2222
<212> TYPE: DNA
<213> ORGANISM: Artificial Sequence
<220> FEATURE:
<223> OTHER INFORMATION: universal polynucleotide donor cassette
      sequence: pDAB117421

<400> SEQUENCE: 141
gagagctggg gaagactatg cgcgatcgcc tgcaggctcg tcgctgatca ccagtatcta       60
ctcgtacagt actccatgga tgcgtacgcg cccgggaact cctcggcgtc gtccgggctg      120
accgacatgg cacgcgcatc gaggatgtag atgcacgtga gccacaggtt agtagagtgg      180
taggagcagt gttggactga tggctcgctt acataagcag ttctgtccca tggagccaat      240
gtcctgatac ggtaggacac atatcccttc atgaatcggc caacgcgcgg ggagaggcgg      300
tttgcgtatt gggcgctctt ccgcttcctc gctcactgac tcgctgcgct cggtcgttcg      360
gctgcggcga gcggtatcag ctcactcaaa ggcggtaata cggttatcca cagaatcagg      420
ggataacgca ggaaagaaca tgtgagcaaa aggccagcaa aaggccagga accgtaaaaa      480
ggccgcgttg ctggcgtttt tccataggct ccgcccccct gacgagcatc acaaaaatcg      540
acgctcaagt cagaggtggc gaaacccgac aggactataa agataccagg cgtttccccc      600
tggaagctcc ctcgtgcgct ctcctgttcc gaccctgccg cttaccggat acctgtccgc      660
ctttctccct tcgggaagcg tggcgctttc tcatagctca cgctgtaggt atctcagttc      720
ggtgtaggtc gttcgctcca agctgggctg tgtgcacgaa ccccccgttc agcccgaccg      780
ctgcgcctta tccggtaact atcgtcttga gtccaacccg gtaagacacg acttatcgcc      840
actggcagca gccactggta acaggattag cagagcgagg tatgtaggcg gtgctacaga      900
gttcttgaag tggtggccta actacggcta cactagaaga acagtatttg gtatctgcgc      960
```

```
tctgctgaag ccagttacct tcggaaaaag agttggtagc tcttgatccg gcaaacaaac  1020
caccgctggt agcggtggtt tttttgtttg caagcagcag attacgcgca gaaaaaaagg  1080
atctcaagaa gatcctttga tctttttctac ggggtctgac gctcagtgga acgaaaactc  1140
acgttaaggg attttggtca tggcgttcgg aaccgtgctg acccgcaagt ggcaacctcc  1200
cgtgcctctg ctcacccttta ccgcctggca actgcggcc acctgcaggg cgatcgcacc  1260
gagcgcttag tgggaatttg taccccttat cgaaccggga gcacaggatg acgcctaaca  1320
attcattcaa gccgacaccg cttcgcggcg cggcttaatt caggagttaa acatcatgag  1380
ggaagcggtg atcgccgaag tatcgactca actatcagag gtagttggcg tcatcgagcg  1440
ccatctcgaa ccgacgttgc tggccgtaca tttgtacggc tccgcagtgg atggcggcct  1500
gaagccacac agtgatattg atttgctggt tacggtgacc gtaaggcttg atgaaacaac  1560
gcggcgagct ttgatcaacg accttttgga aacttcggct tcccctggag agagcgagat  1620
tctccgcgct gtagaagtca ccattgttgt gcacgacgac atcattccgt ggcgttatcc  1680
agctaagcgc gaactgcaat ttggagaatg gcagcgcaat gacattcttg caggtatctt  1740
cgagccagcc acgatcgaca ttgatctggc tatcttgctg acaaaagcaa gagaacatag  1800
cgttgccttg gtaggtccag cggcggagga actctttgat ccggttcctg aacaggatct  1860
atttgaggcg ctaaatgaaa ccttaacgct atggaactcg ccgcccgact gggctggcga  1920
tgagcgaaat gtagtgctta cgttgtcccg catttggtac agcgcagtaa ccggcaaaat  1980
cgcgccgaag gatgtcgctg ccgactgggc aatggagcgc ctgccggccc agtatcagcc  2040
cgtcatactt gaagctaggc aggcttatct tggacaagaa gatcgcttgg cctcgcgcgc  2100
agatcagttg gaagaatttg ttcactacgt gaaaggcgag atcaccaagg tagtcggcaa  2160
ataatgtcta acaattcgtt caagccgacg ccgcttcgcg gcgcggctta actcaagcgt  2220
ta                                                                2222
```

<210> SEQ ID NO 142
<211> LENGTH: 110
<212> TYPE: DNA
<213> ORGANISM: Artificial Sequence
<220> FEATURE:
<223> OTHER INFORMATION: Analytical Domain

<400> SEQUENCE: 142

```
gagccacagg ttagtagagt ggtaggagca gtgttggact gatggctcgc ttacataagc   60
agttctgtcc catggagcca atgtcctgat acggtaggac acatatccct              110
```

<210> SEQ ID NO 143
<211> LENGTH: 118
<212> TYPE: DNA
<213> ORGANISM: Artificial Sequence
<220> FEATURE:
<223> OTHER INFORMATION: Analytical Domain

<400> SEQUENCE: 143

```
actagttttc atagggatat gtgaggacta accttggcca aaggagctgg aactgcctgc   60
agttatgtaa gggccttagt ccaaattgct ccaccctctg ggaagctaat ggactagt     118
```

<210> SEQ ID NO 144
<211> LENGTH: 21
<212> TYPE: DNA
<213> ORGANISM: Artificial Sequence
<220> FEATURE:
<223> OTHER INFORMATION: Primer

<400> SEQUENCE: 144
cgccacaaat ctgaaccagc a   21

<210> SEQ ID NO 145
<211> LENGTH: 24
<212> TYPE: DNA
<213> ORGANISM: Artificial Sequence
<220> FEATURE:
<223> OTHER INFORMATION: Primer

<400> SEQUENCE: 145
ccacgatcga cattgatctg gcta   24

<210> SEQ ID NO 146
<211> LENGTH: 21
<212> TYPE: DNA
<213> ORGANISM: Artificial Sequence
<220> FEATURE:
<223> OTHER INFORMATION: Primer

<400> SEQUENCE: 146
gcgacatatc aggccaacag g   21

<210> SEQ ID NO 147
<211> LENGTH: 25
<212> TYPE: DNA
<213> ORGANISM: Artificial Sequence
<220> FEATURE:
<223> OTHER INFORMATION: Primer

<400> SEQUENCE: 147
gggatatgtg tcctaccgta tcagg   25

<210> SEQ ID NO 148
<211> LENGTH: 21
<212> TYPE: DNA
<213> ORGANISM: Artificial Sequence
<220> FEATURE:
<223> OTHER INFORMATION: Primer

<400> SEQUENCE: 148
ccagcataca gttagggccc a   21

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
gttgccttgg taggtccagc   20

<210> SEQ ID NO 150
<211> LENGTH: 21
<212> TYPE: DNA
<213> ORGANISM: Artificial Sequence
<220> FEATURE:
<223> OTHER INFORMATION: Primer

<400> SEQUENCE: 150
cgaaaactca gcatgcggga a   21

<210> SEQ ID NO 151

```
<211> LENGTH: 21
<212> TYPE: DNA
<213> ORGANISM: Artificial Sequence
<220> FEATURE:
<223> OTHER INFORMATION: Primer

<400> SEQUENCE: 151
gagccatcag tccaacactg c                                              21

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
acaggcgtac agcaacacca                                                20

<210> SEQ ID NO 153
<211> LENGTH: 22
<212> TYPE: DNA
<213> ORGANISM: Artificial Sequence
<220> FEATURE:
<223> OTHER INFORMATION: Primer

<400> SEQUENCE: 153
gaccctatgg tgttggatcc ca                                             22

<210> SEQ ID NO 154
<211> LENGTH: 21
<212> TYPE: DNA
<213> ORGANISM: Artificial Sequence
<220> FEATURE:
<223> OTHER INFORMATION: Primer

<400> SEQUENCE: 154
cgggagctag gcaacaaatc g                                              21

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
tctgactaaa cgggtggatg ctg                                            23

<210> SEQ ID NO 156
<211> LENGTH: 26
<212> TYPE: DNA
<213> ORGANISM: Artificial Sequence
<220> FEATURE:
<223> OTHER INFORMATION: Primer

<400> SEQUENCE: 156
cggatcagtt gattcgctca ctttca                                         26

<210> SEQ ID NO 157
<211> LENGTH: 21
<212> TYPE: DNA
<213> ORGANISM: Artificial Sequence
<220> FEATURE:
<223> OTHER INFORMATION: Primer

<400> SEQUENCE: 157
```
gccgaaaagc agcaactgga a                                              21

<210> SEQ ID NO 158
<211> LENGTH: 21
<212> TYPE: DNA
<213> ORGANISM: Artificial Sequence
<220> FEATURE:
<223> OTHER INFORMATION: Primer

<400> SEQUENCE: 158
gattgctacg cagaccgcct a                                              21

<210> SEQ ID NO 159
<211> LENGTH: 21
<212> TYPE: DNA
<213> ORGANISM: Artificial Sequence
<220> FEATURE:
<223> OTHER INFORMATION: Primer

<400> SEQUENCE: 159
cactattcct ccggcatgca g                                              21

<210> SEQ ID NO 160
<211> LENGTH: 22
<212> TYPE: DNA
<213> ORGANISM: Artificial Sequence
<220> FEATURE:
<223> OTHER INFORMATION: Primer

<400> SEQUENCE: 160
tgacctattg atcggtcggc tc                                             22

<210> SEQ ID NO 161
<211> LENGTH: 22
<212> TYPE: DNA
<213> ORGANISM: Artificial Sequence
<220> FEATURE:
<223> OTHER INFORMATION: Primer

<400> SEQUENCE: 161
tgccttgaat ctcagggatg ca                                             22

<210> SEQ ID NO 162
<211> LENGTH: 21
<212> TYPE: DNA
<213> ORGANISM: Artificial Sequence
<220> FEATURE:
<223> OTHER INFORMATION: Primer

<400> SEQUENCE: 162
gccgaagcta actagcggac a                                              21

<210> SEQ ID NO 163
<211> LENGTH: 21
<212> TYPE: DNA
<213> ORGANISM: Artificial Sequence
<220> FEATURE:
<223> OTHER INFORMATION: Primer

<400> SEQUENCE: 163
catggagtag cagctgtgct g                                              21

<210> SEQ ID NO 164
<211> LENGTH: 21
<212> TYPE: DNA

```
<213> ORGANISM: Artificial Sequence
<220> FEATURE:
<223> OTHER INFORMATION: Primer

<400> SEQUENCE: 164
gaaaagcagt caccggctct g                                              21

<210> SEQ ID NO 165
<211> LENGTH: 22
<212> TYPE: DNA
<213> ORGANISM: Artificial Sequence
<220> FEATURE:
<223> OTHER INFORMATION: Primer

<400> SEQUENCE: 165
ccatggacat gaattcggca cg                                             22

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
cttttgcacc acggagcaga c                                              21

<210> SEQ ID NO 167
<211> LENGTH: 25
<212> TYPE: DNA
<213> ORGANISM: Artificial Sequence
<220> FEATURE:
<223> OTHER INFORMATION: Primer

<400> SEQUENCE: 167
gctagcaaaa ctttgaagct cgctc                                          25

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
gaggtccctt acgggtcatc g                                              21

<210> SEQ ID NO 169
<211> LENGTH: 22
<212> TYPE: DNA
<213> ORGANISM: Artificial Sequence
<220> FEATURE:
<223> OTHER INFORMATION: Primer

<400> SEQUENCE: 169
accaggtcta tcttgcgcag ac                                             22

<210> SEQ ID NO 170
<211> LENGTH: 21
<212> TYPE: DNA
<213> ORGANISM: Artificial Sequence
<220> FEATURE:
<223> OTHER INFORMATION: Primer

<400> SEQUENCE: 170
aatagcgtgg tcgggtccta g                                              21
```

<210> SEQ ID NO 171
<211> LENGTH: 21
<212> TYPE: DNA
<213> ORGANISM: Artificial Sequence
<220> FEATURE:
<223> OTHER INFORMATION: Primer

<400> SEQUENCE: 171
acgaacgatc caaggtgcag t                                               21

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
tagagacgag gactctgggc t                                               21

<210> SEQ ID NO 173
<211> LENGTH: 21
<212> TYPE: DNA
<213> ORGANISM: Artificial Sequence
<220> FEATURE:
<223> OTHER INFORMATION: Primer

<400> SEQUENCE: 173
aagtccaaca tgggcacaac c                                               21

<210> SEQ ID NO 174
<211> LENGTH: 21
<212> TYPE: DNA
<213> ORGANISM: Artificial Sequence
<220> FEATURE:
<223> OTHER INFORMATION: Primer

<400> SEQUENCE: 174
cctcgttaag ggtgcaggtt g                                               21

<210> SEQ ID NO 175
<211> LENGTH: 26
<212> TYPE: DNA
<213> ORGANISM: Artificial Sequence
<220> FEATURE:
<223> OTHER INFORMATION: Primer

<400> SEQUENCE: 175
ccaagtcagc ttctaagcca tcaaac                                          26

<210> SEQ ID NO 176
<211> LENGTH: 22
<212> TYPE: DNA
<213> ORGANISM: Artificial Sequence
<220> FEATURE:
<223> OTHER INFORMATION: Primer

<400> SEQUENCE: 176
aaccctagac ttctgcctgg tg                                              22

<210> SEQ ID NO 177
<211> LENGTH: 22
<212> TYPE: DNA
<213> ORGANISM: Artificial Sequence
<220> FEATURE:

<223> OTHER INFORMATION: Primer

<400> SEQUENCE: 177
gctcacttac gagcagatcc ca                                    22

<210> SEQ ID NO 178
<211> LENGTH: 21
<212> TYPE: DNA
<213> ORGANISM: Artificial Sequence
<220> FEATURE:
<223> OTHER INFORMATION: Primer

<400> SEQUENCE: 178
ggtgcacgca tgttctcatg t                                     21

<210> SEQ ID NO 179
<211> LENGTH: 21
<212> TYPE: DNA
<213> ORGANISM: Artificial Sequence
<220> FEATURE:
<223> OTHER INFORMATION: Primer

<400> SEQUENCE: 179
tgtttaccgc agccatgctt g                                     21

<210> SEQ ID NO 180
<211> LENGTH: 23
<212> TYPE: DNA
<213> ORGANISM: Artificial Sequence
<220> FEATURE:
<223> OTHER INFORMATION: Primer

<400> SEQUENCE: 180
gttgtatacg gcatccatcc gct                                   23

<210> SEQ ID NO 181
<211> LENGTH: 23
<212> TYPE: DNA
<213> ORGANISM: Artificial Sequence
<220> FEATURE:
<223> OTHER INFORMATION: Primer

<400> SEQUENCE: 181
gaatgaaact ggtggtctgc tcc                                   23

<210> SEQ ID NO 182
<211> LENGTH: 22
<212> TYPE: DNA
<213> ORGANISM: Artificial Sequence
<220> FEATURE:
<223> OTHER INFORMATION: Primer

<400> SEQUENCE: 182
ccgacgaggt acaagtagca gg                                    22

<210> SEQ ID NO 183
<211> LENGTH: 23
<212> TYPE: DNA
<213> ORGANISM: Artificial Sequence
<220> FEATURE:
<223> OTHER INFORMATION: Primer

<400> SEQUENCE: 183
cccgtagtcc agattcttgt ggt                                   23

<210> SEQ ID NO 184
<211> LENGTH: 21
<212> TYPE: DNA
<213> ORGANISM: Artificial Sequence
<220> FEATURE:
<223> OTHER INFORMATION: Primer

<400> SEQUENCE: 184
gtcgtttgtt cggaagggga g                                              21

<210> SEQ ID NO 185
<211> LENGTH: 21
<212> TYPE: DNA
<213> ORGANISM: Artificial Sequence
<220> FEATURE:
<223> OTHER INFORMATION: Primer

<400> SEQUENCE: 185
cgtagttgtc cggcatgtcc t                                              21

<210> SEQ ID NO 186
<211> LENGTH: 21
<212> TYPE: DNA
<213> ORGANISM: Artificial Sequence
<220> FEATURE:
<223> OTHER INFORMATION: Primer

<400> SEQUENCE: 186
tgtatccctt cggtgagcac g                                              21

<210> SEQ ID NO 187
<211> LENGTH: 22
<212> TYPE: DNA
<213> ORGANISM: Artificial Sequence
<220> FEATURE:
<223> OTHER INFORMATION: Primer

<400> SEQUENCE: 187
tgaatcgact cgctgacagg tg                                             22

<210> SEQ ID NO 188
<211> LENGTH: 24
<212> TYPE: DNA
<213> ORGANISM: Artificial Sequence
<220> FEATURE:
<223> OTHER INFORMATION: Primer

<400> SEQUENCE: 188
ccacgatcga cattgatctg gcta                                           24

<210> SEQ ID NO 189
<211> LENGTH: 25
<212> TYPE: DNA
<213> ORGANISM: Artificial Sequence
<220> FEATURE:
<223> OTHER INFORMATION: Primer

<400> SEQUENCE: 189
gggatatgtg tcctaccgta tcagg                                          25

<210> SEQ ID NO 190
<211> LENGTH: 20
<212> TYPE: DNA
<213> ORGANISM: Artificial Sequence
<220> FEATURE:
<223> OTHER INFORMATION: Primer

<400> SEQUENCE: 190
gttgccttgg taggtccagc                                            20

<210> SEQ ID NO 191
<211> LENGTH: 21
<212> TYPE: DNA
<213> ORGANISM: Artificial Sequence
<220> FEATURE:
<223> OTHER INFORMATION: Primer

<400> SEQUENCE: 191
gagccatcag tccaacactg c                                          21

<210> SEQ ID NO 192
<211> LENGTH: 20
<212> TYPE: DNA
<213> ORGANISM: Artificial Sequence
<220> FEATURE:
<223> OTHER INFORMATION: Primer

<400> SEQUENCE: 192
tggcactaat ctcaccggct                                            20

<210> SEQ ID NO 193
<211> LENGTH: 22
<212> TYPE: DNA
<213> ORGANISM: Artificial Sequence
<220> FEATURE:
<223> OTHER INFORMATION: Primer

<400> SEQUENCE: 193
agtcttagaa gtacgctacc gt                                         22

<210> SEQ ID NO 194
<211> LENGTH: 19
<212> TYPE: DNA
<213> ORGANISM: Artificial Sequence
<220> FEATURE:
<223> OTHER INFORMATION: Primer

<400> SEQUENCE: 194
tacttggctt cggcggcga                                             19

<210> SEQ ID NO 195
<211> LENGTH: 21
<212> TYPE: DNA
<213> ORGANISM: Artificial Sequence
<220> FEATURE:
<223> OTHER INFORMATION: Primer

<400> SEQUENCE: 195
gggtgacttt tacgcgtctc g                                          21

<210> SEQ ID NO 196
<211> LENGTH: 20
<212> TYPE: DNA
<213> ORGANISM: Artificial Sequence
<220> FEATURE:
<223> OTHER INFORMATION: Primer

<400> SEQUENCE: 196
ggtcacgacg catggcctaa                                            20

<210> SEQ ID NO 197
<211> LENGTH: 20

```
<212> TYPE: DNA
<213> ORGANISM: Artificial Sequence
<220> FEATURE:
<223> OTHER INFORMATION: Primer

<400> SEQUENCE: 197
aggatgcatg gatcaccgtc                                                    20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
gctctgttgt gcagccgtac                                                    20

<210> SEQ ID NO 199
<211> LENGTH: 22
<212> TYPE: DNA
<213> ORGANISM: Artificial Sequence
<220> FEATURE:
<223> OTHER INFORMATION: Primer

<400> SEQUENCE: 199
cgttgcagat accacagtgt ac                                                 22

<210> SEQ ID NO 200
<211> LENGTH: 25
<212> TYPE: DNA
<213> ORGANISM: Artificial Sequence
<220> FEATURE:
<223> OTHER INFORMATION: Primer

<400> SEQUENCE: 200
gctagtagct gtttacacgg cgtct                                              25

<210> SEQ ID NO 201
<211> LENGTH: 22
<212> TYPE: DNA
<213> ORGANISM: Artificial Sequence
<220> FEATURE:
<223> OTHER INFORMATION: Primer

<400> SEQUENCE: 201
aggtcgagac aaccaagtag ag                                                 22

<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202
acaggacatc gagcttgcat                                                    20

<210> SEQ ID NO 203
<211> LENGTH: 23
<212> TYPE: DNA
<213> ORGANISM: Artificial Sequence
<220> FEATURE:
<223> OTHER INFORMATION: Primer

<400> SEQUENCE: 203
```
cagaagaaag gcatcaactc atg                                            23

<210> SEQ ID NO 204
<211> LENGTH: 26
<212> TYPE: DNA
<213> ORGANISM: Artificial Sequence
<220> FEATURE:
<223> OTHER INFORMATION: Primer

<400> SEQUENCE: 204
ctctttcacc tctacttta cttcag                                          26

<210> SEQ ID NO 205
<211> LENGTH: 21
<212> TYPE: DNA
<213> ORGANISM: Artificial Sequence
<220> FEATURE:
<223> OTHER INFORMATION: Primer

<400> SEQUENCE: 205
attgaaccgt tgtcaaagcc a                                              21

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
cacagcgtca gggcggtaac                                                20

<210> SEQ ID NO 207
<211> LENGTH: 20
<212> TYPE: DNA
<213> ORGANISM: Artificial Sequence
<220> FEATURE:
<223> OTHER INFORMATION: Primer

<400> SEQUENCE: 207
ggcacgcacc tgtcactgac                                                20

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
gtacgcgccc gggaactcct                                                20

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
cctgcggccc acgtgcatct                                                20

<210> SEQ ID NO 210
<211> LENGTH: 3213
<212> TYPE: DNA
<213> ORGANISM: artificial sequence
<220> FEATURE:
<223> OTHER INFORMATION: optimal loci_ 204637

<400> SEQUENCE: 210

```
ggaaacgaga gtgggataaa caagcgtaaa aaatgaacgg gaacgagagt attaagcgga      60
aacttataat ttaatacaaa acacacgtga tattgatggc gagctagcag tacaacaaca     120
tggaacaaac agatacagag agacaattaa tactacattg ttatttgctt gtttgtggtg     180
tatatatata gctacgacca gcgttgttta agtctttagg acatttgtca ttaaggggag     240
gcaattaata ctacattgtt atttgcttgt ttgtggtgta catatagcta ggtagaataa     300
cctttatgc tataatttgc atatataatg ctttagctaa tgcattaatg catcttgggc     360
cgatcccggg tttctaaaat atataataaa taccggttca acctggctaa aaacgagtgg     420
gatagaccct atcatgtttt agaatttttt cacaaataca aaaacagacg gatcaaatat     480
agaaaaatga tattggtcgg gacgtcctct ttcaaccttg catgcgggtc ggtcgtcgag     540
ccaattttca gctttgcggg tgaagtaaaa gaagcgaagc caagtagcaa gcacgcatgg     600
gcatggccgc atgggccgtg cgggcgtgca tggcacatgg cagcgcgcag cacatcgatg     660
gatcctcggc tccagccggc gtcaggcgac acagatgtct tccgtgcaaa cggccgctga     720
aagagacgag acgaccgcgt tcttgtggaa gaaaagaagc gagatcgagg ctcggcgggg     780
cgccccttg gcagcaggc aaggcatcgg tacggatcca attccatgcg tgggaatctc     840
ccggagctag gccggaggga agggagcctg gggagagccg aaggggaaac agtgcggtcg     900
gcagcggtcc gcggtaggaa gggtgatgac aggagcggga gtaaatgcct gtagcccgta     960
ggggcacggt cgtctcccgt caaccggctg gccgccgcgc ccgcctcggt cgccatgcca    1020
cctgcagcag cagcagcatc gagccctgc atgcattgca tgccatgcat gcagcagcag    1080
cagcaggcca ggtcaggcca ggtagcgtag cgcccgtagc gcgggctccg tccgtccatg    1140
tccctgtccc tggccgcagc tactaggagt actatagtgt gtagtactgc tcagcagccg    1200
tgcagtgcgg tgcgcggcgg aggggcgggc gagctggcaa agtggcaact ggcttggcta    1260
ggctagcttt ccgttggcgt ggttgggctt tgcaggacag ctggtgcacg tgacggggcg    1320
ggaggggca tgcttcccta tatcagccac agctaccgcc gtactagccc cccgcaccta    1380
gctttagcta gggccagccg gccgcccgtc tcccggctgc gttgtggttg tggtggagtg    1440
gatgggagat gagatggatg atgccattgt cacatcacgc acctgccgct gccgcgcgcg    1500
caaggcgcac ttgcctgccc tgggccctcc tcccaccggg ggtctcgtct ggcaccgtca    1560
cttcatgggg aggggaagca tgggcatggc tgcatggtgc gtgcaccacg cttcattcgt    1620
atatacagct gttagccggg atggatcggc tgatgctctc aactgaagtg atcgataaaa    1680
agcggtcgct tggtattagc tggcctcgtg ccgtccggcg ggacgcgttg gaagcttttt    1740
cgactccggg gagacttttt ttttagactt gcaatccact ctcactgatc cactgctttt    1800
ctgctcgtgt gctaaactgc taactcggca atatagcatc actcatttgc ggtgcaactg    1860
cagtgcgcag cctacagatc caaagctacg tactgtactc taaattcctt gctgtagtac    1920
gtgaaacgtc atgcgtatcc ggccggctcc cgcgagacag gaagagacag cgactcgcag    1980
acttgcagct gcccagcagg cagtagcttg ccctttttaa tcgcagcact tggggttgac    2040
agtcacacac acactggtcg cggcgcggca gatgaggcgc cacaaatctg aaccagcata    2100
cagttagggc ccatgatttc cccccttcct ctatggtttt tatatataaa aaactgatt    2160
tatatgaaac ttttgtatga ttcctcctaa attcctgcat ttcaaataag acatcgagct    2220
```

| | |
|---|---|
| agtgtaagcg taggcctgca aagctgcagc tgcctgttcc ctgtactact tggcactaat | 2280 |
| ctcaccggct acgtgccttc gcatacggag tagtttattc gcggtgggac acttgataga | 2340 |
| aaggctacgg tagcgtactt ctaagactat ggtcatttaa aacactattt tatactatag | 2400 |
| tctatactgt tactacacta gagttaaaat ataaagatga atatagataa attactgaag | 2460 |
| atagtctaaa catcttttcc attttttaag aggacacgcc taaacagttg tgaatacata | 2520 |
| catacacacc gatacacaga tgctaaagca ctaaagcccc taaaaagttg gtgatacatg | 2580 |
| aaccaacacg aaatcgatca cctttgaacc cgccagtcct actaccactc tccttcgttt | 2640 |
| gacctagctg gctggttaag aaaaaaagtt cgttttccgt aaaagcgatc caagtgacaa | 2700 |
| cgacgagacg tgattttccg tacctgactg atgttgatac cagccactac tccgagctag | 2760 |
| tagtaaaaga ttttttacagc caggggagag acggcgttcg tctgctagtg gctagaccgc | 2820 |
| gcgtgttgcg cgacgccggg ccggggcgcg cggtcggcca cggactggca gccggtgcga | 2880 |
| ggcacgccgc gtggtccagc tagatcgccg accgggcacg gcagacgacg gccggtccag | 2940 |
| cggctggaca cgggcacacg agagtacgag actgcgcgcg tttaggttgg taccactacc | 3000 |
| accatgcatg tcgcgactcg ctcgtccgat tatggagcaa aaacacctgt cgtcatgcga | 3060 |
| atcattgtac ggcatagcga taagaaaaaa aaacttaccg cttctagcat gcccgtcgta | 3120 |
| tgcgacgacg aagttgagaa atcatgccca agcaagcttc ccgcatgctg agttttcgct | 3180 |
| gaccctgttg gcctgatatg tcgctgaccc tga | 3213 |

<210> SEQ ID NO 211
<211> LENGTH: 4938
<212> TYPE: DNA
<213> ORGANISM: artificial sequence
<220> FEATURE:
<223> OTHER INFORMATION: optimal_loci_204726

<400> SEQUENCE: 211

| | |
|---|---|
| ctcaatcgcc aaagtagaga atgatgtttt tcagcctaca ggccccaggt agcagctgtg | 60 |
| tgttgcaaag caacttgtat aatacaattg acaagttcg agcttcaaat aactcatata | 120 |
| ccatgcaaag caaattggat ggttttcagc ccacgtaatt aaatggaaat caagttttcc | 180 |
| aacctgtcaa gcactacatg attaattgaa accttcagtt ctgcatgggt gccaatctgg | 240 |
| ccaatagaag tgttattgct tatgcagttt gcacatgatt taaatagatg aaaacaaata | 300 |
| acaaagtaga gttagtgctt gcagtcagct tgtcccactc ccatacttcc tttgcacttt | 360 |
| tcctcccagc aaattagtac cagcttttac gtgtcctcat cataacaagt attgaccatg | 420 |
| aatcaaaata cagacatcac tcacagctca cagttccagg ccatggttac aacctagcac | 480 |
| taagttgacc aaggcttcta aatttagaac ttttaatagc agaagtgcct tgaagatgta | 540 |
| aagcctgcaa atatacagga gggacaatga tcagattctc caccaacata actcactagt | 600 |
| gctttgggtt aacaataatc atataaagga accaagttat gctgacagaa aattatttgg | 660 |
| aataatacca gcaatcaaat aaaagaacca agttgtgctg acaaaagcaa cataaagacc | 720 |
| aagaaactat atgacaaaaa ttttgtgaat acatcattct tttgtgggcg aagagtatac | 780 |
| gtagatatta gtttatttaa aaaattaaaa aattggttta aaatttagtt aaagctcatt | 840 |
| ttttgcctga gtcaaggtaa tacaacacat cagtatcata tatccaaatc tgtggattca | 900 |
| ccagctcaaa ggaagatagc aaagataaca acaggttagc gttgctgaat tgtaaagtac | 960 |
| agaactagct agtgttgctg aattgtaaag tccacaagca aattgttgca gctcgccttc | 1020 |
| atgctaagaa attgacatgc tgaattgttg agcatgcagc tgaaacacac ttagataaac | 1080 |

| | | |
|---|---|---|
| taaggtatat atacatgcag cctaattaaa gtactagaac tactaattac ttggtaatgc | 1140 |
| actacatatg tgtagaatgt tcagaggaac agctagcgtt gttccaacat gtgcatgaac | 1200 |
| ttttaactga aagggcatgt tttatcaatc tctttagacc tcagtagagt ttaggcagtg | 1260 |
| gaaagctact aactaggaga gatgtcattt attttttaac tatcacttaa caggcagaat | 1320 |
| tagccaaaca aaaaaggac catgcttttta catagacaac ctgtaaagtc catgtgacag | 1380 |
| aaaatatatt ggatgcaaac tgacttagga actaaaaaag cttgaatctt tttgtattta | 1440 |
| gatccaaaga acccctgacc attttttcaaa atggctgtta agaaaacctt gaaaattctt | 1500 |
| gtccattata tcctattgtt acttgatttc tgaaaccgat gtataaataa tcagagcaaa | 1560 |
| ctttactgaa aagtggtggc acatcgagga ggagaggaag caaccaggga aggcacggca | 1620 |
| taggaacgtg cgctgtgcac atgcgggctt attgtcttag ctagaaaagt ggtgtgagtc | 1680 |
| aggtcaggtc aggtcagagg gggatcgatg gaccgatccg attcggcagg cggaacaagt | 1740 |
| gaaggttcag tgcacggcga ggcgagtcca ccggagcgac tgagggaaac aaagcaaagc | 1800 |
| aaaagggaca gagggatccc agaacggggc gggggtgcgg acgacggaaa gcgaaagcga | 1860 |
| cggcacggag gggtgggcac cattagatta ctggtatctg gacggccgac caggtacagg | 1920 |
| cgtacagcaa caccagccac acacaccgac ccagccagca aaaccgctcc tccgcctttc | 1980 |
| ggcttccagc caggttttcg tttcgcgtgg ttttcccctc cctccgcgcg gcctactaaa | 2040 |
| tcaatcactc acccgccgtc gtcggggtgg ctggcacgcg tgcgctccag gggtgggctg | 2100 |
| ggtgcatgca cccgcgcggt taagctagct ctggcgcata gccgtccgcg tcaccgggag | 2160 |
| ctaggcaaca aatcggaggc ctctcgggcg cgcgcgtcgc tgtctgccgc agccgcagcc | 2220 |
| tgctgtactg tacttggctt cggcggcgac ccccgcgtcc aagtggttgc ctgggaggcc | 2280 |
| ccggctccgg gcatcgcgac gcgacgcgac gagacgcgta aaagtcaccc gtcgcggtct | 2340 |
| cgcatgcgcg agggaggcag gcaggcagcg aacaaaatcg cacgcgcgtc gtcgactgcc | 2400 |
| tggcctggcc tggtccagct gaaaaccgcc ccggtttgcc tccgtttgcg ggatctggat | 2460 |
| gggctgtttt cgcgctggcg ggggtcaatg caaaacgggc gatgtgccgt gtggtgtgcg | 2520 |
| cggcgcggcg tcactttccc ttaacttctc gcgctggaag aggcagctgc ctgcttttgc | 2580 |
| cgcagctgaa aaggaggagg aagaaaatga tcggccggat tggatggcga cggcgggcgg | 2640 |
| aagcggaacc ttcttgcttg gccgctgacc atgacacctg gccccgcttt gcagcccgtg | 2700 |
| gaggactctt ggcagctttt acgcgtgccg ccggtgtgcg tgcgttgtct aggcaaggca | 2760 |
| cggcaagcag agcacgcgag ggcggatgag gaattttgac actgcaaaaa tcccaaatcc | 2820 |
| gcaagtatgc acactcaccc gcacgaccag tagcgtgact gcgtgagtac tgtttagttg | 2880 |
| gtcacccata ggagtagcgt tctatatatg aacaggagaa acaaaaatat atgcccttgt | 2940 |
| tagtcgttcc gaatttcaaa aaaattggaa atcagtcgca cggcctacta tgctatatgc | 3000 |
| ccttggtagt cggcacgacg ggtatatacg ggatggaacc gagccggtgc gtgatttccg | 3060 |
| tggacgtgac attgattgga gtggtcatac agactgctgg gactggagtc ttgcatacaa | 3120 |
| acatccaaga cagcatccac ccgtttagtc agagtcagac tcgagtacga cgaatatcga | 3180 |
| tcagacaaga gccaaatcca tttgggatcc aacaccatag ggtcattatt gttttgggac | 3240 |
| catgggaccg gatcatgcgt atatactatg tgtctattat tagcatgccg acgcgcgcat | 3300 |
| tcggccgcta gataggccct ctgacagtaa ttaatatatg aggaggagag gaaatacttt | 3360 |
| ccacctattt ttttctcgct atagaggatc gttgtcaaaa aaacaacctt tttggttagg | 3420 |

```
gtttgacctc tgtttatcca attcaatttg agtgaattaa tttttagtga caaatgatac    3480
atcaataaga catttatgat aacttcaatt ttcaagattt atgaacctag ccagttggat    3540
acctagataa aggtagagtg tactttcatt aaggatggac atgtgttagg tgtggaccca    3600
cataataata tgtatttgaa aagtacttaa agtaggaact tgtatcctaa tatgtatttg    3660
acatgcacgc gtgacttggt ggcctcggcg accgagcgcg gaggcaaggc atgtggcacc    3720
gatcgaagca ggcacatata actgtcgccg cgccgtatag agtcggcact gacccaccca    3780
cccctgcgtc ctagctagct agttgctact agctccgatc gcgatcggta gggtagggac    3840
gacgatacga tgcatggatt gaccaccgtg caaggtctgc agatgatgcc atcggtctct    3900
gacgatcatc tcgacacgga catccggaat tgtattgggt ctggtagctt ctggctgccg    3960
gccggctgct acttgtacgg ccaataatgc gtggtgagtg gtctgctgca ctggatctgc    4020
aggcgaggcg tctgatcatg cagcatatgc gtggtgcccc ggccgccacc cgcgtacgtt    4080
gttgcgaagc cgggaggaca gcacattgta cgtgcaccgg ccccatacta cttatggacg    4140
acagaatatg cgtggcagca gaaccccatg acgcgggtgt ccgctggcga gcacggggcc    4200
ggagagacgg ccgcgacgtg acgagggaac aaccacccca acccaaccaa cgcgcgtagg    4260
ctcagcccgg cggcggcccc tgcccaggag ccgggcgggc tccacgtaca tcgatcagtt    4320
ggattcgatc actgtgcaga tccacgatcc atgccccatc tccatgcgtg tcttgtcctc    4380
ttgcttgcta tcaacctgac atccaagtgg tgcacagcgt gaggagatcg gagcggagat    4440
ccgggctgtg tctgtgcgcg gcatgtccgt acgcgcagtg tacgccgcag tcctgctcct    4500
gcacgcggtc acgggacggg actgagccaa ctcgatctga ggatgattgt ttttctgggc    4560
ccgcgctgcg cgccttgtgt ttgttcgacg tgttttgtg catctacggc gccgatcgta    4620
tagtagcatg tctgaaatct gaatgcctgg tgatagctca gctgcctgcc tgcgccctgc    4680
ggcattgcag ttgcagccct gttgattctc gatttgggaa caccaagaca ggcgcagatg    4740
aattgcatgt gtccgtaata tgcctgcact gcacccctgca taggttgcag taacaaacta    4800
acaatccctg acaacgtac gcgtgacaac gtcttgacca ggagaagagc aacgcgcgcc    4860
acaggcatcc ggccagagat gccgcaaggc ctgactagcc cagcggccag cgccactgca    4920
tgcattgcat ccaggacc                                                 4938
```

<210> SEQ ID NO 212
<211> LENGTH: 1370
<212> TYPE: DNA
<213> ORGANISM: artificial sequence
<220> FEATURE:
<223> OTHER INFORMATION: optimal_loci_156393

<400> SEQUENCE: 212

```
acggaagttg gcgccgcgag agcaggacgt ggtttggacc agaccagatc agagcgtcgg      60
tcggttcctg ttcctggtgg tatggcaccc atggaggccg ataaactaac tagtcaaggc     120
attggatccc gcgggcctgg aaaagcagtc accggctctg gacctgggac tgggaggcaa     180
gccctccggc tttttgcacca cggagcagac acgggctcca ggaatcgatt cagtgcagcg     240
gcacgccgag gcgcctcaca tgattcctca gcacatgcct gcctgcactg cacagccggg     300
aagtctgttc acttgtactg cgtcgtccct ggcgcgagg atgatagcta aggctcgctt      360
cccgcgacac acgtacccac gcacgcacgg aaccagaacg ttttgccgac ttcgtgtgat     420
caaggaccgt tgatcacgcc gcgctgctac taaaggatat ataaaaaaaa tgacagcgct     480
cggcgtcttc aggcttcaga accgttgatc aaggacgatg agcttgagag ctgaatccgg     540
```

```
acggatcgga ctgcgtcgac gacgataaac agcagtgcct gcatgctctg ttgtgcagcc      600
gtacgtgccg tgcgccggtg tatgtctgca tgcgcagtac ttattttctg aagcaggtat      660
atacaatata ctagctagta cactgtggta tctgcaacgt agtactgatc tggattctcc      720
atgttggcgt gtatactctc tttcttcac aggatcaagt tcatgcactg agcaccagat      780
cagattcagc caccgatcga gggagaggga gtgccggagc cggagcagga caggggcgg      840 cgacgtccca cgtgcacggc gatctcaatt atattctcat gcatgcagcg acaccggat      900 cgaggaagcg cggcaaagcc tcgtgatttc gatcggacgc cccgatcgca tcgcatcgca      960
tcgcatcgca tcgcagcagt gcgcaagggc agaaccgcag ggcatggcgc ccgaacggag     1020
cccatcagcg cccagtcgat cggcaagccc agagcgagct tcaaagtttt gctagcttcg     1080
tgccgaattc atgtccatgg atatcggaat gtgcatgcag cagttgttgc cgggcaattg     1140
atgcagacaa ctcttttttt tttttcaaat atccgggttt atttatatat atacgagata     1200
caatagatag ctttggccac aagcgattaa atgacgctgg tcggtaggga agcttctggt     1260
ggagaccaga cttgagaaaa aaaataaacc caagacctat aaaggcaaga caatcatgcg     1320
tgctctgtcc tccgggaaga taaatggctg catgaagcag ttgaataaaa                1370
```

<210> SEQ ID NO 213
<211> LENGTH: 1190
<212> TYPE: DNA
<213> ORGANISM: artificial sequence
<220> FEATURE:
<223> OTHER INFORMATION: optimal_loci_198387

<400> SEQUENCE: 213

```
gaacatcctg catgcatata gcctggctgg tggcagcatt cttttcttca tgcgagccag       60 accctttta tcaggaaacc aatcaaaccc tagacttctg cctggtgcac gcatgttctc      120
atgtcattta agaaatgcac ataattttgc cggttctgta cgattaggac ttttcattta      180
atttcgtaca tttttaccaa aagttagtca gattagttca aaataaataa aaaactagtt      240
tttccccaaa aatcataaga ccatttgtgg taaagcatta ttatatgata acaaagaaa       300 actaaggtct tgtttggttg accttgtgag ttgtgaagct gcttttgttt tggtcaaaac      360
caaaagtcaa taagaggag aaaagaaata gctacttttg ctctagtaca taatttatga      420
ctctttcacc tctactttta cttcagttgt gaaaaataac gatttatttt cctcgtttct      480
tgtgcccgaa agagagaggt gtaacccatc ctctataaca gtgtggcttt gacaacggtt      540
caatatgtat gttggatgc aggcccaagg tcgcttggcc aaatattggc cttgacaaac       600
caatttggcc catgtttagt tggaggccaa atgttggcca tgaccaggaa attttggtcg      660
tgcaaatgta gatttgtgcc aattcttggt cataatcagc gcggacaaac cggctaccca      720
aatttggctt ggtcgtattg cattttaacc ataaaccaaa catccaaact tgaacccaat      780
tttggcttga tccaactttg gccagctacc taattttagc attttctctgg tccacaacac     840 aacaggccct agtgcgagcg tggccctggc acgctaccct gccttgacgc gtgtgaagcc      900
ttagtggcag cctcaaccgc aggtgtggat ccggcggcgg tcatggcgtg tgcggccctg      960
acaatggcca tggtgcaggc gcttccaaca tggtcatggc gtgggacagc atgcggtcct     1020
gtccccagcg catgtgttgc cccaacacaa gcatggctgc ggtaaacaac tttggcgaga     1080
ggaagatgga aatgtgagtc taacaagtgg gtctgcttat aagtgtgtga gagagaaagt     1140
tgagtggatg acatgtggga tctgctcgta agtgagctac aataaacacg                1190
```

<210> SEQ ID NO 214
<211> LENGTH: 3965
<212> TYPE: DNA
<213> ORGANISM: artificial sequence
<220> FEATURE:
<223> OTHER INFORMATION: optimal_loci_31710

<400> SEQUENCE: 214

```
gtttgtttca atttcataat ttaccattgc aacagctgct cttcgacgca gaaacatttg      60
tcgtggttgg agaaatatgt atatgtgcaa ccaacaaagt tcagattgat tacgacgaag     120
atcggcgcta gcttgtttca agagaaaaca aatgcatctc ttgaggcaac atcggagaga     180
caaaaatggc atgtagttt cttacacaca acggaattgc tgatgaaggt tttagtgatt     240
gatggatgat atttgtagta actagtttta ttcatcaagg gaagtttgtt ccaatggaaa     300
tgtgcacaac tactaaaaat atcttatcgt ctcagaagga agaattggtg aatatattta     360
gcctcatttc ctagacgcat acatatattc catactaagt caataaatcc atggacacca     420
aaatgctgca taattagcga atgcaaggat gcctcgccgg ttttaagaaa ttctggtagt     480
agcttgcaag ccaacgccaa gacgacgaac tagtcttaag ttgaaaagat cctgatggta     540
aaactctatc atctttcctt tgcctcattg tcttgcatga caattttttg gttttctgt      600
gttctgattt aattggttga atgttgtaag acagaaactg ggttacttca ttatcttaat     660
gaaataaaat cccttcataa aaaaaagct tgaatgtctt agtgatctag ctcgtatttc      720
tctcttttga agcttccttg tccgttgcag tatcgtccaa ttgcagaaaa aatggtgtgg     780
aaatttgatg ttttcttgtg ccaagatggc tcatcaggtg ttgtatttgt atatattctc     840
tcccttttaa aattaggcaa tatcgggtgg ttagtgactt ggttctctca ccatgatgcc     900
actatcaacc tccatttgtt cagaagatat tcgcaaaaat atacagccat tctaattaag     960
ttcgtgttgt ggaagatgta aatctgttgt cctaacctgt ctaaatatga acaaagataa    1020
ctagattgtt tgcacgtata gacacagcac caaattcgac caaatctggc ctcattgcag    1080
aagtgtaaaa tgttaacaac tactacgcac agctcctgct gtatttgtgt aaaactgaca    1140
aagaaacttg tgggcggcgg attcggtgag ctttatctct acgtgttgca ctttagatgt    1200
ttatatataa attctgttga caaaagatta ctggagtttc tagttccacc cagttaaggc    1260
cgtacgccaa ccctttgaag agttgggatc ttctacgtgg catgattcat ttctgacagg    1320
gattattatt aatggagaag tttccttaag ttcgaagcat ggctaaacaa gcaacaccta    1380
actaacctcc tgcatagggt aaaacagtcc ccgaatattg tattaagaag aagacaggtg    1440
aagtaaactc gtaaagcggc accatatata gggcattgtg agaacggtcg cagttaggat    1500
tgggtcttag acatgtgctt ttggcgtgag attcagaaga tctaaggatt gctacgcaga    1560
ccgcctaatc atataaatta tgaaccaatg catggattaa ctaataatat cgatagatgt    1620
gtcttttttt tctctctatt ctgtgggatc ggatcagttg attcgctcac tttcactcac    1680
ttttctttg cgccgatgtg tccgcagtta ccttccccat catgaacttg agaccgaaa     1740
ggtgtggtgc ctagttaccc cgtactgcaa tttaccaatg gcgctggggt ggaaataaag    1800
ggcaggcgca caacacagaa aggaccagca gcagcaccac caccaccggg cactagctag    1860
ctagctctct ggtcaatgga gcatgcagct tagctgggat tcagacactg ttgctggctt    1920
gctgctgctg caattgcttg ttcaaggcga acacaagaga gatccgaagc atggttgagt    1980
ctctgggcgt agaaaacagt gccggtttcc atcggttaga caagaacgca agagagagat    2040
cgtccatacg acgtgcatga ggaccagatg gagattcaga gacgaccca tcttctttgc    2100
```

| | |
|---|---|
| ataaagaaac tagatgaagc ttgtgtcgtc gcctataaga aatgaaacat ctgcattgtc | 2160 |
| agcgtagtat cccagctgat ggagaggaca tacccatgag gcaataaatc aaacgacctt | 2220 |
| ttaattttta cagccaatgc attgcatgct gcattatcaa actggcgaaa agtgcttttt | 2280 |
| tttaaggggg ggaaggctac catgggttgc attgaccgag tgcccctct cgtagggcct | 2340 |
| atgccacatt actttcttga aaggcaacca caggctgatc tggaagtcca ttccacggtg | 2400 |
| gcatgcatgg gcggcgccac acgtcagtca tccgctcgag ggcaagcttc ggtcgatcga | 2460 |
| tgacgctgcc cggctgcatg ccggaggaat agtggagaag ggtgcagagc agagggatgg | 2520 |
| tcagatcatt ccagttgctg cttttcggca cttgcatatg tgatatatgg agcaaacagc | 2580 |
| accgctggct ggatggatcg gatcgcatac accatatatg atcgaagatg agcctagcca | 2640 |
| tgcatgttgc aatatggact actatgtaca tctgtcgcac gtactagctt gatattaatt | 2700 |
| cagtgtacat ccaattacac acatgcatat gcagtaactg gacgtttatt tgcacacttg | 2760 |
| cactatatac acatcgatca gacgtcgctc cagagtacat tcagcactgg gttttctttt | 2820 |
| tctttgggac tgactgctat gctagcaagt cactaactca ctatagctag ctagctagct | 2880 |
| ttgtcttgtg tttttttttcc ctgtggatgg atcgtcctgg cagtggagga gattgttggt | 2940 |
| ggggtggtgg agctgagatg cagcattatt tgaaagagat gcgcgtcaaa tgattaagtc | 3000 |
| agggacgcct ttccacatat tcgtgattca gttgggcata ttgcactgca ggcaggctag | 3060 |
| ctagttgacc agaaaagtga gttgttgttg cattgcattg catgcatgag atccaagtac | 3120 |
| gtgttaacct gggtaggatg tttcctaaca tgatcacaca cttccccatc atcatatcac | 3180 |
| tagtaagcta gcccttgctg gaatgtacag gacccaacaa aaagaccatg catgcatgca | 3240 |
| tgactaaagt ccataatgta acactgcacag acagaggata tagatagaac agccgcgccg | 3300 |
| gcctgaagaa acatcagcag gtcatcaacc acttagtggc tgcatgctcc tactagtctc | 3360 |
| ggcaggccat ttctttctag aggacaaaaa cgcttgcaag ggtactctag cttagacggg | 3420 |
| cagagatcga gatgggtagc tagtgggagg tgtggtaatg ctgtgcccat ttgctggagg | 3480 |
| ctagctgctt gttggagagc tagctaaggc gtgggagagg ccaggggggg ataagagatg | 3540 |
| atgctcgggc aaggcaactt gggtggtcgg gccgagacct gcaaaaggca agtagtagct | 3600 |
| gagctgggac gacggcattg gaggcctctt ttttccgatc ccgctttacc acttctttct | 3660 |
| atcgcatctc atcgatcccc caatcccagc cgatcctcgc tcatcgtggc cccataatgc | 3720 |
| gtgctgcccg ctagcttagc tgccattgcc attggaagca ccagtccata gcagcgcgtt | 3780 |
| gctgcatccg gcggctgcct gttggggagg agacgatgca tgcacgcgtc caatccggtt | 3840 |
| gttcgttctc aataatatca ccccggcccg gcccgtattt agagatattc gcccgagcgc | 3900 |
| agtccagcta gcacagcaac gcagtcgcag tgcatgcaat gcaagttgga gtctgtcagc | 3960 |
| gttac | 3965 |

<210> SEQ ID NO 215
<211> LENGTH: 1330
<212> TYPE: DNA
<213> ORGANISM: Artificial Sequence
<220> FEATURE:
<223> OTHER INFORMATION: optimal_loci_64542

<400> SEQUENCE: 215

| | |
|---|---|
| tatatatatc cggttggcgc ttaaaaaaaa tccaagctac gcggtgtgtg tcatcgatcg | 60 |
| gttgttgctt ggagagcatg gaaaggctgg gcatcactgg gactggtaga gcattgcatg | 120 |

```
ggtgccctac tcgactagcc gactccttcc ttgattgctc gccggtcgcg cgcgcggcgc      180
gcgggcccat gcaacatgca tgcatgatga atggggccg ccgggacagg gcgcccatgc       240
tggggtgctt gacctattga tcggtcggct cctcggccgc ggcgcgcgcg attccaccac      300
caccgtcgcc ggtcacccgc cgaagctaac tagcggacac ccggcgcgcg gctccggcgc     360 tttttccccca tggccccatc cctctcccaa agtggaaaag gggggaaaag ggataagaag    420
ggacaaaacc acgaaggta cgtggaacgt gggtgagggt ctggaagcca agatagggtc      480
acgacgcatg gcctaaaaag tgtcgcgagg cagggagcag ccgcgtgtcc gcctgctgct    540
gctggaatgg cgcggtggcc gcgcgcggtg acggtgatcc atgcatcctc ctgtcctatg    600
tacaacctca aagctactac gactactact gtggttttta tactccgtat atatgagaac    660
tacaagtcgg caaggctggt ctcgcctgct cttgccaagc aaagtgagta gttacacggc     720
gctggctgat gcatgcgtga cacggtggct agctagctgt tgatcccggc cggcccgtgg    780
acgaacccgt acgcgtacgt gtgtttgcgt tgcatcccaa acaagtgctc ggttgctgtt     840
gccgtggacg atcgatcgat cggcccacgc atcacatcat cattcattcc ggccggatcg     900
atcgggcact gtggaagcaa cgaaaccgcg cgcagccgcc actgtggctt ggccttggtg     960
gcagcaggag gacgcagctg cggccggtgg gcaggggcg gaggcggagg cggaggcgcg    1020
gagcaagcag cacagctgct actccatgca tgcatccctg agattcaagg catcaagcaa    1080
gcgtctgcgt ctctgagact ctgactctct gtagcgacta gtggtgggcg agggtcgagt    1140
ggtcgacgca gtaagctcag gtcagggcca ctgggccagc atcgatttta tggcaagaca    1200
tgggcgcgcg cgagatgggc acccacagtc gactgcccct ctgcatgtgg ccctggcacc    1260
ccgcctgcag gcctacacaa cacaacagcg ggagcagtcg gctgcagagg atcccgtccc    1320
cagaaggcca                                                            1330
```

<210> SEQ ID NO 216
<211> LENGTH: 1081
<212> TYPE: DNA
<213> ORGANISM: artificial sequence
<220> FEATURE:
<223> OTHER INFORMATION: optimal_loci_197372

<400> SEQUENCE: 216

```
agaacgggtc ggtatcgagg agcggcgaga taatagaggc aatgtgacaa tgtgtaaaca      60
cttagggtcc tagcatcctt gaagtatgtg tatgtgctaa agaaatagca cttggctcct     120
tggaaggtcc tagagacgag gactctgggc tcctcgttaa gggtgcaggt tgaagtggag     180
acccagagct actagcaatt acaggccatg aggagatagt atccctcatc caacattgag    240
tatccatggt ataggtactt atttataacc aactgctctt gttgtcttct ttgttgtatg    300
aactatagta actcaagcat atatctagat cagtagtgat ggtgaaatcc ctagtggaag    360
tcgatgccac acgtaaattc tttgtttggc tactcaatag aagaagattt atatacccac   420
accccaagaa acttgccccc cagccatcca tcaatccaaa gataacccaa attgtagcac    480
tagatgttga aacgagtcgt gttgagcaag gaacaatgtc tacactgaag atggtggcag   540
gacaggacat cgagcttgca ttaactagca aagtgattcc ttccatccat gcaagaagct    600
acatcccagt gggtgcggca aaagccacac taacacttca tgagttgatg cctttcttct    660
gaatgttcaa ttcaaatctt gcatgggcga gggagctcta gtctaagctg tatgaaaagg   720
ttggagactt ccatcaaact gttgtgtgtc gagtagtaga aaccaacaac aaagtcattg    780
tatggtactt agagtagata gggacaacat gctattgtgt gccaagtagc aagaaacaac   840
```

-continued

```
aatggagcca ctatatgcta cttagattag ttggactagc ttagaccata gttttccaat      900
ggcttagagc tgaattggaa gatctggtca tgtctgagtt ggacttgtac tcttgtcaaa      960
ctaggtttgg accatggttg tttgatggct tagaagctga cttggaatac ttggttgtgc     1020
ccatgttgga cttgtactct tagttgaatt gggtttggaa catagttgtc ccttagctta     1080
g                                                                      1081
```

<210> SEQ ID NO 217
<211> LENGTH: 3903
<212> TYPE: DNA
<213> ORGANISM: artificial sequence
<220> FEATURE:
<223> OTHER INFORMATION: optimal_loci_232228
<220> FEATURE:
<221> NAME/KEY: misc_feature
<222> LOCATION: (2818)..(2917)
<223> OTHER INFORMATION: n is a, c, g, or t

<400> SEQUENCE: 217

```
ccgtgtgtca gcatcacgtg cgcggcgaga ggaaggatga cgatggcttg gttgctcgta       60
gttgtagaga gatagaatga aagcttcttt cagttctttg tatatgtaaa ttcttgctaa      120 taatttttttg tttttaaatat acatatatat taacgttttc gtggatggtt attgttgtag    180
tacttaacat gagaatgagt gcatggccgg aatgggatgg catgatgaac catttcaatt      240
tagtatcagc cttcggtggg aagcaaacca taagcgcgcg tacacatacc acaccacacc      300
ggcatgagtg caaggcatta acgactcgca atggatgtcc tgtcgaagcg agagggacgg      360
ggtgggtggc ctgggtccgg cattatccct ttgccgagct cgagcagatc aggcgaaaaa      420
aaatcggatg aggctgctcc ggcgcggagt cggccaccga agcgagtgca ggcgcaggca      480
gccagccgtc gtggatcccg cgatccgggc cccgggatct ccgctgccca catggcccgg      540
tggccgccag ggtggtggcc gcacggagag gcgtccggat cgggcaccgc ggctgccgct      600
gggaggacgt gggacccacc tctggacatc aggacgtcag gcgcatgttc tcgtaggcca      660
cgcgctgaca cgatcaactg ttgcggaaca aaaatggcgc tgtgtcacgt ccatcatcca      720
tgccgtcagt ataagcaagt actactaatc gagcgcgatg cacgctgatt ggcgaccgag      780
gtggtgctaa ttattggtgc ctgtactacc taaatggcta ctgcatggaa cggaatcacc      840
ggaggcaggc aggcaggcag cgatgacgag tcttaggcca gagtcgctgc gggcacctgt      900
cgcctcacgg gcgcctggtt gccgtcacgg gctgtgcctg ctcggcttcg gcttcggctt      960
cggctccgcc tgccgccccg cgcgcgctcg gatcggttgg tttggctgct cctatccgga     1020
acgggatgga ttccgatagg tggatgagta aaactaactg gagcgagccg ggaccggcag     1080
gcagaggcgc cgcgcgctcc acgtcgacca accagctcct ccagtcccac tagccgggga     1140
cggggaggac agcatccgat gtggccacac ccgcttcacc agccggccgg tgaccacttc     1200
gaccagcgag cgagccgttg tgtggctgct ggttggacag ccgacgcgcg cgccgggggg     1260
gccccgcttg ttgtatacgg catccatccg ctgccgctgc ggcgggcggg cggcgggtg      1320 ccgacgaggt acaagtagca ggacaggagt gcaggatggc tgcgcggcta cctgaccgtg     1380
acccgcgacg gggacggggg gaccccgtc gccgtcggca cagcgtcagg gcggtaacat      1440
gcgttccgtt gcgcgtacgg accaccggtg tcgtctaaca ggaagagctg tcagtgacag     1500
gtgcgtgccg ccgagtgacg gccgcgcaac ccatccgcgc gctcctgctc cggctagcct     1560
atccagtgcg gttcgtggtg ttcctctcag cgtgtctcgt cgtcggcccg gtcggcagcg     1620
```

```
gcagaatttc atttcagact gttgcctcgc cgaggattgt gcagattttt ttttgtgtgc    1680
cggccgatgg agagtttccc gtacaaaagt tgtggatgca ggttacacca tatccagtga    1740
atactcattc ttagccttgt ttacgtacta cggttccaaa gataggctaa cttaatactt    1800
ctgcatgaac aaccctcctc ccacacacca tctcagctca ctatccaaac ttcaatacgt    1860
tcagcaaatg aaaaacaaag tacaaacaaa cgaagctaag aataaagatg ttgggacgat    1920
taagttataa tcatgcattt acggttttcc acgtagacag gggtatatga tgaaaaagaa    1980
cattaattat gccaaaactt tagtggtact gaactagtat aggtattgat ccactgaatg    2040
attaaaaaaa aatcaacatc cattgtgcct cacaaagaga taggcaaaac ttcacggcaa    2100
agtaatatga tccagggcaa atatgtatgg cacattaaat gataactcca agtggatctt    2160
tcatgttctt tatcttcagt gctaatacca caagaatctg gactacggga gcagaccacc    2220
agtttcattc atatatttt tttatgaaaa aaaattatag tacgtatcag gggtgggtct    2280
gtgggtgggg ctacttgctg cactcaaaac gtcaagtagt tgtctagatg gcacatagcc    2340
tatcaactat caagttcatt acaaaaatta tatacaaatg caacaggtca atggaaggat    2400
catatttaag ctgggttcag gagcagtagt gaacaataca cacttttcag tccactagcc    2460
taacacttca gtgcagcagt tgacctatac acaaatagca tgttttagtt caaatttacc    2520
tgaaacacag cataccactt gaactcccag actccagatt ggtggtctac cacatgtcaa    2580
ctgagttgtg ccagggttga catataaagc agtacacaaa atgtttcagt cataaatgtg    2640
gaaaaacaca tcatgcaact actaggattt tactaccaga tagatagtgg acacaaacat    2700
caccgagata cttccctgaa aaggaaagaa attgcaacat cacggtacaa gtaaaatgtg    2760
aaggacaaca acacgggcgt agaacatgga gagacgtctg tgtcgagcaa agtgtaannn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnaat atatagtcac actgcaaaag    2940
atatggacaa gttcaagtgt caactgatgt taaatggtaa ttaaacattc atattaatag    3000
gagagcaatg ttctacgatg tgggggtggg ggggggggtgc tgagctagac agtcaaagaa    3060
agccctcgac aacctaaaag aactatgcgg tttttggatg acaactagca tgactaggca    3120
gccatcctgc aatggagatt gacgttgttt cctcaaaaaa aaaatgtagg ccggtgttgc    3180
atgcatggaa ttttttttg aactgccaaa tgccccttct gcctaaaagt ttaggcttta    3240
agcacaactg gttaagctaa ttaggactac taaaatgtag acttaaacaa ttttatgcag    3300
tacctgacag atgcagcttc gtgctcagca gctagcgtta gtaaagaagc atggatactc    3360
tttaaatata gctatttata gcatctaccg tctaggtgag taggcagaca ttgttcagca    3420
tttgagccct tggaattttc tagtaaaatg tcatttttat aagaattgca aaaggttcca    3480
cccatgcagc catgctgcac tagttcgaaa gagaaatggt gtgtgctttt tttaaggaaa    3540
cattttccag tagtcttcta aacaatccct cgaagctggt agccgaccag ctacatgccc    3600
aatcccaaat ttgttttttc taacaaaatt tcaaaaatgt aactgaaaac aagatctagc    3660
agcaaatata actaaaaaac ctgctaagca gtaacaatag gactttaagc tctggttgca    3720 gtataaaatat aatcaaatg cggtggttat gtgatctgta gttcagattg caagattttt    3780
caagctagga ataacgcctt gcatcatcag attcctttgg ttcaaacata tgataaacct    3840
gagataaaat ttaaactatt cttgttcttc ccacatagca ttctgggtaa gccattaaac    3900
ttc                                                                  3903
```

<210> SEQ ID NO 218
<211> LENGTH: 1172
<212> TYPE: DNA
<213> ORGANISM: Artificial Sequence
<220> FEATURE:
<223> OTHER INFORMATION: optimal_loci_285621

<400> SEQUENCE: 218

| | | | | | |
|---|---|---|---|---|---|
| tacaacaaac | cgaattttaa | tttacaagaa | aataagaatt | tttgaacaaa | tatatttctg | 60 |
| aacttatgag | aatctctagt | tttttttata | ttttttcatg | ctttgttttt | gaattcgaaa | 120 |
| ttccaaacga | aaaaaaatca | aaaaaaagac | ggtagaattt | gtttctgtcg | tttgttcgga | 180 |
| aggggagaaa | acggcgaaac | ccggcgaatc | ccgagcggga | tttgtatccc | ttcggtgagc | 240 |
| acgcggccca | cgcacacggc | agcgatcgtg | tccacggtgt | tatccggcag | cacaaacctg | 300 |
| ctgcgcaaga | acttgcccat | ccgccgctcc | atgcgcaggt | attggcgtct | cgcgctcctc | 360 |
| tggttgccgc | tcgtcgctga | tcaccagtat | ctactcgtac | agtactccat | ggatgcgtac | 420 |
| gcgcccggga | actcctcggc | gtcgtccggg | ctgaccgaca | tggcacgcgc | atcgaggatg | 480 |
| tagatgcacg | tgggccgcag | gccaggtctg | gccgtctggg | gccgtgacgc | cgggagccgc | 540 |
| gccgctgtca | aaccgcgtca | gctcaatcct | agggtccgtt | ttctcaattc | caacgctgt | 600 |
| agacgaaagg | ggtggtgtgg | gcctgagagg | tagagggccc | cggccggggc | tactcgatcc | 660 |
| ggccatcatc | ggctcgccgg | agctcaccgt | gtgcgtgtcc | tacaccacgt | gaccactcgc | 720 |
| ctccatgaat | catcatcaat | tccacccctt | tgccaaggca | caatggccaa | ccatgtgcgt | 780 |
| gctgttaatt | aatttaattt | aacggaacct | tgagggtttc | ttttttgaaa | aaaataattg | 840 |
| accagaataa | tccgatcgca | tcaccacttc | accggcagtc | ctgcagtcca | acactggaag | 900 |
| cgaagcgacc | tctctctgtc | ttgcgtgcaa | cccggccgag | cgcgtcacgc | gtccatctgc | 960 |
| cgcttcgttc | tggcttggcg | caaatgagca | tcacatgatt | ggccgacacc | agcaggcatt | 1020 |
| gcagatcgca | caagcggggg | atgtgatgtg | acgtgaggca | tacacctgtc | agcgagtcga | 1080 |
| ttcagggcga | cacaacgaat | ggagtcgagt | agaacgagag | gacatgccgg | acaactacgc | 1140 |
| ctcgccgagc | ctgcgagctg | taccgaccgg | at | | | 1172 |

<210> SEQ ID NO 219
<211> LENGTH: 1275
<212> TYPE: DNA
<213> ORGANISM: artificial sequence
<220> FEATURE:
<223> OTHER INFORMATION: optimal_loci_157315

<400> SEQUENCE: 219

| | | | | | |
|---|---|---|---|---|---|
| ggaccctata | cactgaagat | ctgccttgac | tatggctaag | gctgaggccc | accgagcagg | 60 |
| ggttgctcct | aaggctcatt | ggagaggaga | cagttccaca | ccacgagttt | gatagaacag | 120 |
| tctagaacaa | cccggggccc | tataggcagc | tccaaccata | agcgcttcta | gatttagttc | 180 |
| tcatggacgg | ccgaggtccc | ttacgggtca | tcggatctct | aataaggtcc | tcagtcttat | 240 |
| tagagaatag | cgtggtcggg | tcctagctag | ggcctctccg | gacttaaggc | cggcctcctg | 300 |
| atgagaagat | aaatgagttc | ctgatgggaa | gcaccagcat | atcagagaac | ataacttatt | 360 |
| acgattttt | tttgtttgtg | cgaggagagc | ttattatttt | gatggctagg | tgtagtcatc | 420 |
| aaggtagaaa | acgatctttc | attagcacga | acaccttact | gtaaataata | agtagtcgtg | 480 |
| tagaaaacat | ttgaccttca | aaggctgcaa | cgagtaaatt | aaaagaaaca | tgcatgtgca | 540 |
| ttattcaatg | tttcaacgaa | aacgtggaac | ttgattttta | ttttgcgtga | gggagcttaa | 600 |

-continued

```
ttatttctgt tgatgtgtaa acacgttgga aatggggccc ccgaaccaca cgtcatactt    660
tttttaatta tttttgtagg ttgctatgct gagctagtag ctgtttacac ggcgtctgtt    720
attctgataa ggaactatat acaaaaccac acatgcacac gtggtcaagg tagtgactaa    780
tctcgcctaa taccactgac aaatcatctc tacttggttg tctcgaccta tagttgctaa    840
aatccatgtg gctaaacttt agttttctct gagttgacga ttaattatta catatacttt    900
atacttgaac tatagttacc tgcatgttgt aaaattatct aaaaattcac gtaggtcaaa    960
tgtggaagaa gtgccataga aaacaacagt cccatattgt gcatcggcaa tgaataatac   1020
cacgtgctac cgaacacggt gaggattact ggtcgttcgt cccgtgatca agctggtagg   1080
tggtatatat gcagctctta tgaagttgtt gagaagattg acgcagtgat ctatcgtcaa   1140
actgaaacgg agacgggcat cactgcacct tggatcgttc gtgcgtttcc atttccattt   1200
ctctgctgcc cgcagccagt gtgcagccgt cgtctgcgca agatagacct ggtcatccgc   1260
tagagcgagc cctgt                                                    1275
```